United States Patent [19]
Godowski et al.

[11] Patent Number: 5,891,650
[45] Date of Patent: *Apr. 6, 1999

[54] KINASE RECEPTOR ACTIVATION ASSAY

[75] Inventors: Paul J. Godowski; Melanie R. Mark, both of Burlingame; Michael D. Sadick, El Cerrito; David L. Shelton, Pacifica; Wai Lee Tan Wong, Los Altos Hills, all of Calif.

[73] Assignee: Genentech Incorporated, South San Francisco, Calif.

[*] Notice: The term of this patent shall not extend beyond the expiration date of Pat. No. 5,766,863.

[21] Appl. No.: 441,104

[22] Filed: May 15, 1995

Related U.S. Application Data

[63] Continuation of Ser. No. 286,305, Aug. 5, 1994, Pat. No. 5,766,863, which is a continuation-in-part of Ser. No. 170,558, Dec. 20, 1993, which is a continuation of Ser. No. 157,563, Nov. 23, 1993, abandoned.

[51] Int. Cl.$^6$ ...................... G01N 33/567; G01N 33/573; C12Q 1/48
[52] U.S. Cl. .................. 435/7.21; 435/7.4; 435/7.94; 435/15; 436/501; 436/518; 436/531; 436/548; 530/388.22; 530/388.26; 530/389.6
[58] Field of Search ...................................... 435/7.21, 7.4, 435/7.94, 15; 436/501, 518, 531, 548; 530/388.22, 388.26, 389.6

[56] References Cited

U.S. PATENT DOCUMENTS 4,859,609  8/1989  Dull et al. ............................... 436/501

FOREIGN PATENT DOCUMENTS 244221     4/1987  European Pat. Off. .
WO 93/15201  5/1993  WIPO .
WO 94/19463  1/1994  WIPO .

OTHER PUBLICATIONS

Pabovsky et al. Protein Engineering. vol. 3. No. 6. pp. 547–553, 1990.
Meloche et al. Molecular Biology of the Cell. vol. 3, 63–71, Jan. 1992.
Cleaveland et al., "A Microtiter–Based Assay for the Detection of Protein ATyrosine Kinase Activity" *Analtical Biochemistry* 190:249–253 (1990).
Corfas et al., "ARIA, a protein that stimulates acetylcholine receptor synthesis, also induces tyrosine phosphorylation of a 185–kDa muscle transmembrane protein" *Proc. Natl. Acad. Sci. USA* 90:1624–1628 (Feb. 1993).
Dijke et al., "Serine/Threonine Kinase Recptors" *Progress in Growth Factor Research* 5:55–72 (1994).
Donato et al., "Tumor Necrosis Factor Regulates Tyrosine Phosphorylation on Epidermal Growth Factor Receptors in A431 Carcinoma Cells: Evidence for a Distinct Mechanism" *Cell Growth and Differentiation* 3:259–267 (1992).
Fantl et al., "Signalling by Receptor Tyrosine Kinases" *Annual Review in Biochemistry* 62:453–481 (1993).
Fujimoto, "brt, A Mouse Gene Encoding a Novel Receptor–type Protein–Tyrosine Kinase, is Preferentially Expressed in the Brain" *Oncogene* 9:693–698 (1994).
GenBank, "Release 79" (along with hstyro3 and hstyro3y sequences available on GenBank) (Oct. 15, 1993).
Glenney et al., "Monoclonal antibodies to phosphotyrosine" *Journal of Immunological Methods* 109:277–285 (1988).
Hagino et al., "Enzyme–Linked Immunosorbent Assay Method for Human Autophosphorylated Insulin Receptor" *Diabetes* 43:274–280 (Feb. 1994).
Holmes et al., "Identification of heregulin, a specific activator of p185$^{erbB2}$" *Science* 256:1205–1210 (1992).
Hunter, "Protein Kinase Classification" *Methods in Enzymology* 200:3–9 (1991).
Hunter, "Synthetic Peptide Substrates for a Tyrosine Protein Kinase" *Journal of Biological Chemistry* 257(9):4843–4848 (1982).
Hunter et al., "Protein–Tyrosine Kinases" *Annual Review in Biochemistry* 54:897–930 (1985).

(List continued on next page.)

Primary Examiner—Ponnathapura Achutamurthy
Assistant Examiner—P. Ponnaluri
Attorney, Agent, or Firm—Wendy M. Lee

[57] ABSTRACT

An assay for measuring activation (i.e., autophosphorylation) of a tyrosine kinase receptor of interest is disclosed.

(a) A first solid phase is coated with a substantially homogeneous population of cells so that the cells adhere to the first solid phase. The cells have either an endogenous tyrosine kinase receptor or have been transformed with DNA encoding a receptor or "receptor construct" and the DNA has been expressed so that the receptor or receptor construct is presented in the cell membranes of the cells.

(b) A ligand is then added to the solid phase having the adhering cells, such that the tyrosine kinase receptor is exposed to the ligand.

(c) Following exposure to the ligand, the adherent cells are solubilized, thereby releasing cell lysate.

(d) A second solid phase is coated with a capture agent which binds specifically to the tyrosine kinase receptor, or, in the case of a receptor construct, to the flag polypeptide.

(e) The cell lysate obtained in step (c) is added to the wells containing the adhering capture agent so as to capture the receptor or receptor construct to the wells.

(f) A washing step is then carried out, so as to remove unbound cell lysate, leaving the captured receptor or receptor construct.

(g) The captured receptor or receptor construct is exposed to a labelled anti-phosphotyrosine antibody which identifies phosphorylated residues in the tyrosine kinase receptor.

(h) Binding of the anti-phosphotyrosine antibody to the captured receptor or receptor construct is measured.

29 Claims, 67 Drawing Sheets

OTHER PUBLICATIONS

Kamps, "Generation and Use of Anti–Phosphotyrosine Antibodies for Immunoblotting" *Methods in Enzymology* 201:101–110 (1991).

Kasuga et al., "Insulin Stimulation of Phosphorylation of the /142 Subunit of the Insulin Receptor" *Journal of Biological Chemistry* 257(17):9891–9894 (1982).

Kasuga et al., "Phosphorylation of the Insulin Receptor in Cultured Hepatoma Cells and a Solubilized System" *Methods in Enzymology* 109:609–621 (1985).

King et al., "High throughput assay for inhibitors of the epidermal growthfactor receptor–associated tyrosine kinase" *Life Sciences* 53:1465–1472 (1993).

Klein et al., "A merotiter well assay system to measure insulin activation of insulin receptor kinase in intact human mononuclear cells" *Diabetes* 42:883–890 (Jun. 1, 1993).

Knutson et al., "Comparison of insulin receptor tyrosine phosphorylation under in vitro and in situ conditiond: assessment of specific protein tyrosine phosphorylation with the use of 32P–phosphate–labeled substrates" *Archives of Biochemistry & Biophysics* 285(2):197–204, 1991.

Kozma et al., "Comparison of Three Methods for Detecting Tyrosine–Phosphorylated Proteins" *Methods in Enzymology* 201:28–436 (1991).

Lai et al., "An Extended Family of Protein–Tyrosine Kinase Genes Differentially Expressed in the Vertebrate Nervous System" *Neuron* 6:691–704 (May 1991).

Lai et al., "Structure, expression, and activity of Tyro 3, a neural adhesion–related receptor tyrosine kinase" *Oncogene* 9:2567–2578 (1994).

Lazaro et al., "Description of an Enzym–Linked Immunosorbent Assay for the Detection of Protein Tyrosine Kinase" *Analytical Biochemistry* 192:257–261 (1991).

Madden et al., "Two Nonradioactive Assays for Phosphotyrosine Phosphatases with Activity toward the Insulin Receptor" *Annual of Biochemistry* 199:210–215 (1991).

Mark et al., "rse, a Novel Receptor–type Tyrosine Kinase with Homology to Axl/Ufo, Is Expressed at High Levels in the Brain" *JOurnal of Biological Chemistry* 269(14):10720–10728 (Apr. 8, 1994).

Mathews, "Activin Receptors and Cellular Signaling by the Receptor Serine Kinase Family" *Endocrine Review* 15(3):310–325 (1994).

O'Bryan et al., "axl, a transforming gene isolated from primary human myeloid leukemia cells, encodes a novel receptor tyrosine kinase" *Molecular & Cellular Biology* 11:5016–5031 (1991).

Ohashi et al., "Cloning of the cDNA for a Novel Receptor Tyrosine Kinase, Sky, Predominantly Expressed in Brain" *Oncogene* 9:669–705 (1994).

Park et al., "Sequence of MET Protooncogene cDNA has Features Characteristic of the Tyrosine Kinase Family of Growth–Factor Receptors" *Proc. Natl. Acad. Sci. USA* 84:6379–6383 (1987).

PAzin et al., "Triggering Signaling Cascades by Receptor Tyrosine Kinases" *TIBS* 17:374–378 (1992).

Pike, "Assay of Growth Factor–Stimulated Tyrosine Kinases Using Synthetic Peptide Substrates" *Methods of Enzymology* 146:353–362 (1987).

Polvi et al., "The Human Tyro3 Gene and Pseudogene are Located in Chromosome 15q14–q25" *Gene* 134:289–293 (1993).

Sale, "Serine/threonine kinases and tyrosine phosphatases that act on the insulin receptor" *Biochemical Society Transactions* 20:664–670 (1992).

Stark et al., "FGFR–4, a new member of the fibroblast growth factor receptor family, expredded in the definitive endoderm and skeletal muscle lineages of the mouse" *Development* 113:641–651 (1991).

Ullrich and Schlessinger, "Signal Transduction by Receptors with Tyrosine Kinase Activity" *Cell* 61:203–212 (Apr. 1990).

Wang, "Isolation of Antibodies for Phosphotyrosine by Immunization with a v–abl Oncogene–Encoded Protein" *Molecular & Celluar Biology* 5(12):3640–3643 (1985).

Wang et al., "Evidence for Association of the Cloned Liver Growth Horomone Receptor with a Tyrosine Kinase" *Journal of Biological Chemistry* 267(24):17390–17396 (1992).

White et al., "Preparation and Use of Anti–Phosphotyrosine Antibodies to Study Structure and Function of Insulin Receptor" *Methods in Enzymology* 201:65–79 (1991).

Wilks et al., "The application of the polymerase chain reaction to cloning members of the protein tyrosine kinase family" *Gene* 85:67–74 (1989).

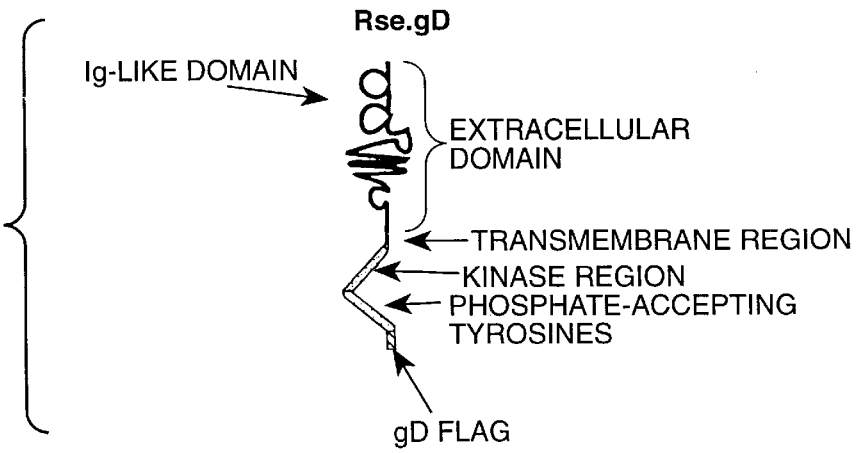
FIG._1A
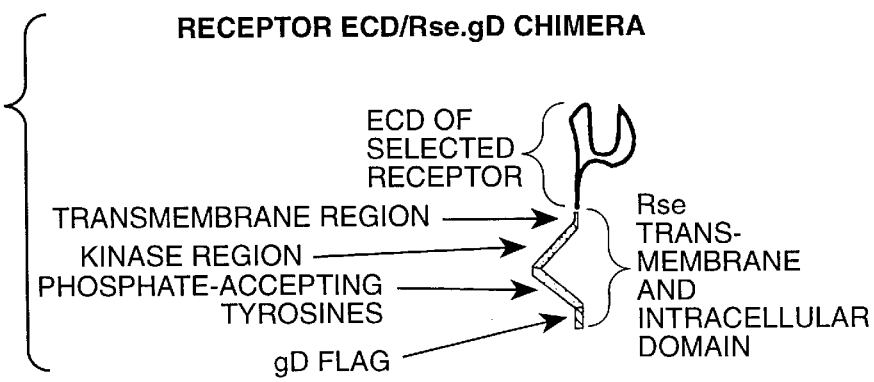
FIG._1B
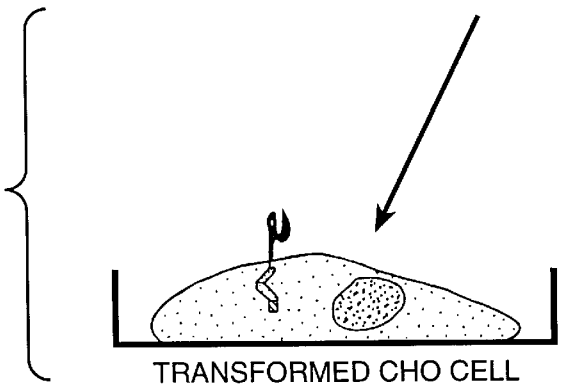
FIG._1C

FIG._2A

```
     signal sequence
     * * * * * * * * * * * * * * * * * * * * * * * * * * * * * * * * * *
     M A L R R S M G R P G L P P P P P P R L G L L L A A L L A S L L
1    ATGGCGCTGA GGCGGAGCAT GGGGCGGCCG GGGCTCCCGC CGCCGCCGCT GCCGCGGCTG GGCTGCTGCT GGCGGCTCTG GCTTCTCTGC
                                           extracellular domain
35   L P E S A A A G L K L M G A P V K L T V S Q G Q P V K L N C S V E
101  TGCTCCCGGA GTCCGCGCC GCAGGTCTGA AGCTCATGGG AGCCCCGGTG AAGCTGACAG TGTCTCAGG GCAGCCCGTG AAGCTCAACT GCAGTGTGGA 68   G M E E P D I Q W V K D G A V V Q N L D Q L Y I P V S E Q H W I G
201  GGGGATGGAG GAGCCTGACA TCCAGTGGGT GAAGGATGGG GCTGTGGTCC AGAACTTGGA CCAGTTGTAC ATCCCAGTCA GCGAGCAGCA CTGGATCGGC 101  F L S L K S V E R S D A G R Y W C Q V E D G G E T E I S Q P V W L T
301  TTCCTCAGCC TGAAGTCAGT GGAGCGCTCT GACGCCCGGC GGTACTGGTG CCAGGTGGTG GATGGGGGTG AAACCGAGAT CTCCCAGCCA GTGTGGCTCA 135  V E G V P F F T V E P K D L A V P P N A P F Q L S C E A V G P P E
401  CGGTAGAAGG TGTGCCATTT TTCACAGTGG AGCCAAAAGA TCTGGCAGTG CCACCCAATG CCCCCTTTCA GAGGCTGTGG GTCCCCCTGA 168  P V T I V W W R G T T K I G G P A P S P S V L N V T G V T Q S T M
501  ACCTGTTACC ATTGTCTGGT GGAGAGGAAC TACGAAGATC GGGGACCCG CTCCCTCTCC ATCTGTTTTA AATGTAACAG GGGTGACCCA GAGCACCATG 201  F S C E A H N L K G L A S S R T A T V H L Q A L P A A P F N I T V T
601  TTTTCCTGTG AAGCTCACAA CCTAAAAGGC CTGGCCTCTT CTCGCACAGC CACTGTTCAC CTTCAAGCAC TGCCTGCAGC CCCCTTCAAC ATCACCGTGA 235  K L S S N A S V A W M P G A D G R A L Q S C T V Q V T Q A P G
701  CAAAGCTTTC CAGCAGCAAC GCTAGTGTGG CCTGGATGCC AGGTGCTGAT GGCCGAGCTC TGCTACAGTC CTGTACAGTT CAGGTGACAC AGGCCCCAGG 268  G W E V L A V V V P P Y A D W V P P F T C L L R D L V P A T N Y S L R V R C
801  AGGCTGGGAA GTCCTGGCTG TTGTGGTCCC TGTGCCCCCC TTTACCTGCC CTGTCCGGGA CCTGGTGCCT GCCACCAACT ACAGCCTCAG GGTGCGCTGT 301  A N A L G P S P Y A D W V P F Q T K G L A P A S A P Q N L H A I R T
901  GCCAATGCCT TGGGGCCCTC TCCCTATGCT GACTGGGTGC CCTTTCAGAC CAAGGGTCTA GCCCCAGCCA GCGCTCCCCA AAACCTCCAT GCCATCCGCA 335  D S G L I L E W E E V I P E A P L E G P L G P Y K L S W V Q D N G
1001 CAGATTCAGG CCTCATCTTG GAGTGGGAAG AAGTGATCCC CGAGGCCCCT TTGGAAGGCC CCCTGGGACC CTACAAACTG TCCTGGGTTC AAGACAATGG
```

FIG._2B

```
368  T   Q   D   E   L   T   V   E   G   T   R   A   N   L   T   G   W   D   P   Q   K   D   L   I   V   R   V   C   V   S   N   A   V
1101 AACCCAGGAT GAGCTGACAG TGGAGGGGAC CAGGGCCAAT TTGACAGGCT GGGATCCCCA AAAGGACCTG ATCGTACGTG TGTGCGTCTC CAATGCAGTT
                                                                                                    transmembrane domain
401  G   C   G   P   W   S   Q   P   L   V   S   S   H   D   R   A   G   Q   Q   G   P   P   H   S   R   T   S   W   V   P   V   V   L
1201 GGCTGTGGAC CCTGGAGTCA GCCACTGGTG GTCTCTTCTC ATGACCGTGC AGCCAGCAG  GCCCCTCCTC ACAGCCGCAC ATCCTGGGTA CCTGTGGTCC 435  G   V   L   T   A   L   V   T   A   A   A   L   A   L   I   L   L   R   K   R   R   K   E   T   R   F   G   Q   A   F   D   S   V
1301 TTGGTGTGCT AACGGCCCTG GTGACGGCTG CTGCCCTGGC CCTCATCCTG CTTCGAAAGA GACGGAAAGA GACCCGGTTT GGGCAAGCCT TTGACAGTGT
                       intracellular domain 468  M   A   R   G   E   P   A   V   H   F   R   A   A   R   S   F   N   R   E   R   P   E   R   I   E   A   T   L   D   S   L   G   I
1401 CATGGCCCGG GGAGAGCCAG CCGTTCACTT CCGGGCAGCC CGGTCCTTCA ATCGAGAAAG GCCCGAGCGC ATCGAGGCCA CATTGGACAG CTTGGGCATC 501  S   D   E   L   K   E   K   L   E   D   V   L   I   P   E   Q   Q   F   T   L   G   R   M   L   G   K   G   E   F   G   S   V   R   E
1501 AGCGATGAAC TAAAGGAAAA ACTGGAGGAT GTGCTCATCC CAGAGCAGCA GTTCACCCTG GGCCGGATGT TGGGCAAAGG AGAGTTTGGT TCAGTGCGGG 535  A   Q   L   K   Q   E   D   G   S   F   V   K   V   A   V   K   M   L   K   A   D   I   I   A   S   S   D   I   E   E   F   L   R
1601 AGGCCCAGCT GAAGCAAGAG GATGGCTCCT TTGTGAAAGT GGCTGTGAAG ATGCTGAAAG CTGACATCAT TGCCTCAAGC GACATTGAAG AGTTCCTCAG 568  E   A   A   C   M   K   E   F   D   H   P   H   V   A   K   L   V   G   V   S   L   R   S   R   A   K   G   R   L   P   I   P   M
1701 GGAAGCAGCT TGCATGAAGG AGTTTGACCA TCCACACGTG GCCAAACTTG TGGGGGTAAG CCTCCGGAGC AGGGCTAAAG GCCGTCTCCC CATCCCCATG 601  V   I   L   P   F   M   K   H   G   D   L   H   A   F   L   L   A   S   R   I   G   E   N   P   F   N   L   P   L   Q   T   L   I   R
1801 GTCATCTTGC CCTTCATGAA GCATGGGGAC CTGCATGCTT TCCTGCTCGC CTCCCGGATT GGGGAGAACC CCTTTAACCT TGCCCTGCAG ACCCTGATCC 635  F   M   V   D   I   A   C   G   M   E   Y   L   S   R   N   F   I   H   R   D   L   A   A   R   N   C   M   L   A   E   D   M
1901 GGTTCATGGT GGACATTGCC TGCGGCATGG AGTACCTGAG CAGAAACTTC ATCCACCGAG ACCTGGCTGC CAGGAACTGC ATGCTGGCCG AAGATATG 668  T   V   C   V   A   D   F   G   L   S   R   K   I   Y   S   G   D   Y   Y   R   Q   G   C   A   S   K   L   P   V   K   W   L   A
2001 GACAGTGTGT GTGGCTGACT TCGGACTCTC CCGGAAGATC TACAGTGGGG ACTACTATCG TCAAGGCTGT GCCTGTCAAC TGCCTGTCAA GTGGCTGGCC
```

FIG._2C

```
701  L   E   S   L   A   D   N   L   Y   T   V   Q   S   D   V   W   A   F   G   V   T   M   W   E   I   M   T   R   G   Q   T   P   Y   A
2101 CTGGAGAGCC TGGCCGACAA CCTGTATACT GTGCAGAGTG ACGTGTGGGC GTTCGGGGTG ACCATGTGGG AGATCATGAC ACGTGGGCAG ACGCCATATG

735  G   I   E   N   A   E   I   Y   N   Y   L   I   G   N   R   L   K   Q   P   P   E   C   M   E   D   V   Y   D   L   M   Y   Q
2201 CTGGCATCGA AAACGCTGAG ATTTACAACT ACCTCATTGG CGGGAACCGC CTGAAACAGC CTCCGGAGTG TATGGAGGAC GTGTATGATC TCATGTACCA

768  C   W   S   A   D   P   K   Q   R   P   S   F   T   C   L   R   M   E   L   E   N   I   L   G   Q   L   S   V   L   S   A   S   Q
2301 GTGCTGGAGT GCTGACCCCA AGCAGCGCCC GAGCTTTACT TGTCTGCGAA TGGAACTGGA GAACATCTTG GGCCAGCTGT CTGTGCTATC TGCCAGCCAG

801  D   P   L   Y   I   N   I   E   R   A   E   E   P   T   A   G   G   S   L   E   L   P   G   R   D   Q   P   Y   S   G   A   G   D   G
2401 GACCCCTTAT ACATCAACAT CGAGAGAGCT GAGGAGCCCA CTGCCCTGGA CTACCTGGCA GGGATCAGCC CTACAGTGGG GCTGGGGATG

835  S   G   M   G   A   V   G   G   T   P   S   D   C   R   Y   I   L   T   P   G   G   L   A   E   Q   P   G   Q   A   E   H   Q   P
2501 GCAGTGGCAT GGGGCAGTG GGTGGCACTC CCAGTGACTG TCGGTACATA CTCACCCCCG GAGGGCTGGC TGAGCAGCCA GGGCAGGCAG AGCACCAGCC gD flag polypeptide
868  E   S   P   L   N   E   T   Q   R   L   L   L   Q   Q   G   L   P   H   S   S   C   A   D   A   S   L   K   M   A   D   P
2601 AGAGAGTCCC CTCAATGAGA CACAGAGGCT TTTGCTGCTG CAGCAAGGGC TACTGCCACA CTCGAGCTGC GCAGATGCTA GCCTCAAGAT GGCTGATCCA 901  N   R   F   R   G   K   D   L   P   V   L   O
2701 AATCGATTCC GCGGCAAAGA TCTTCCGGTC CTGTAGAAGC TT
```

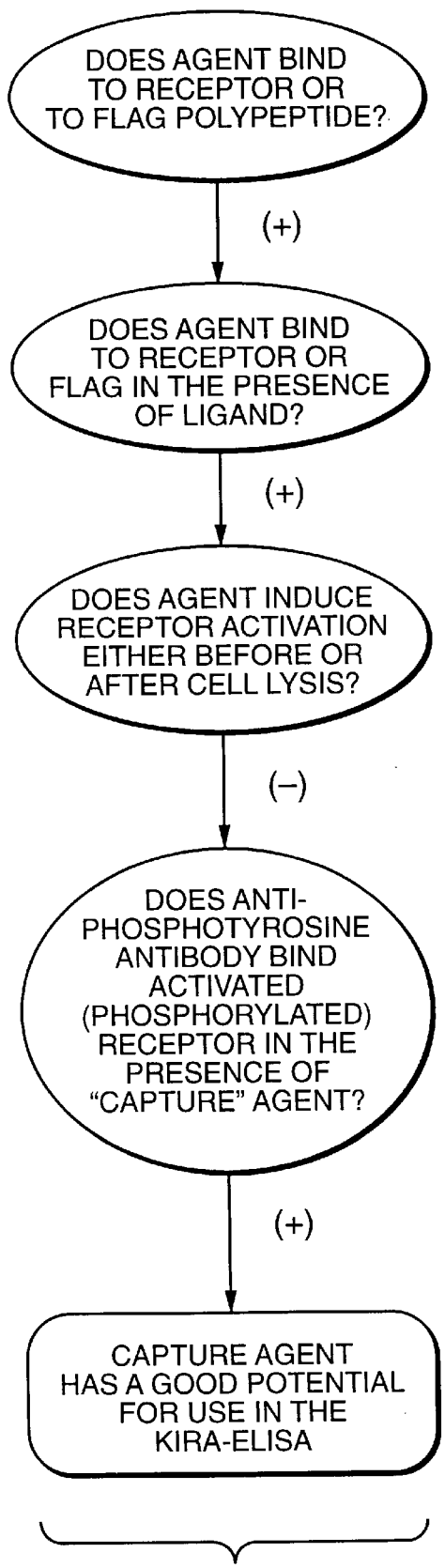
FIG._3

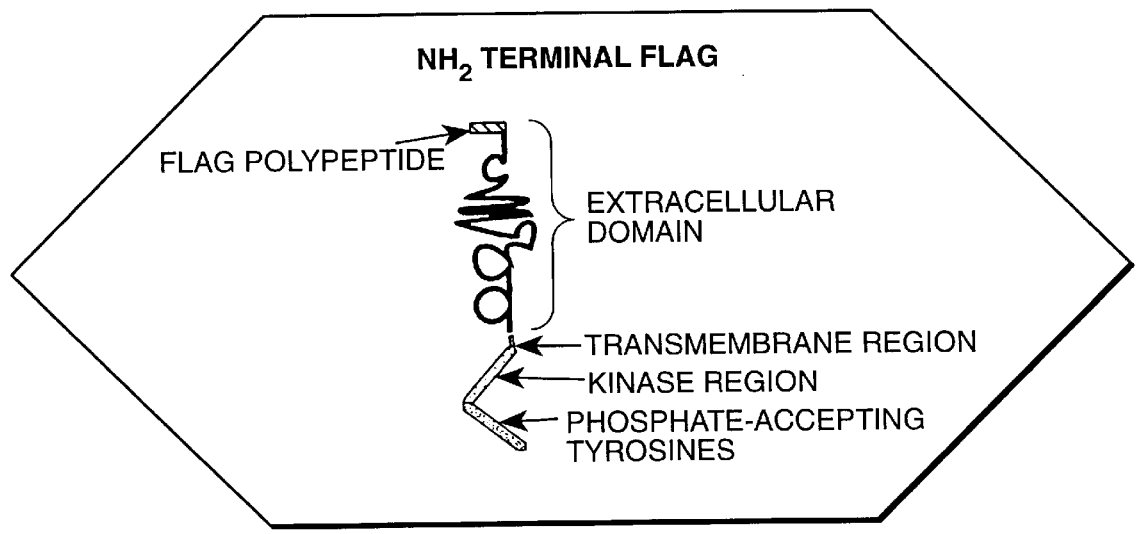
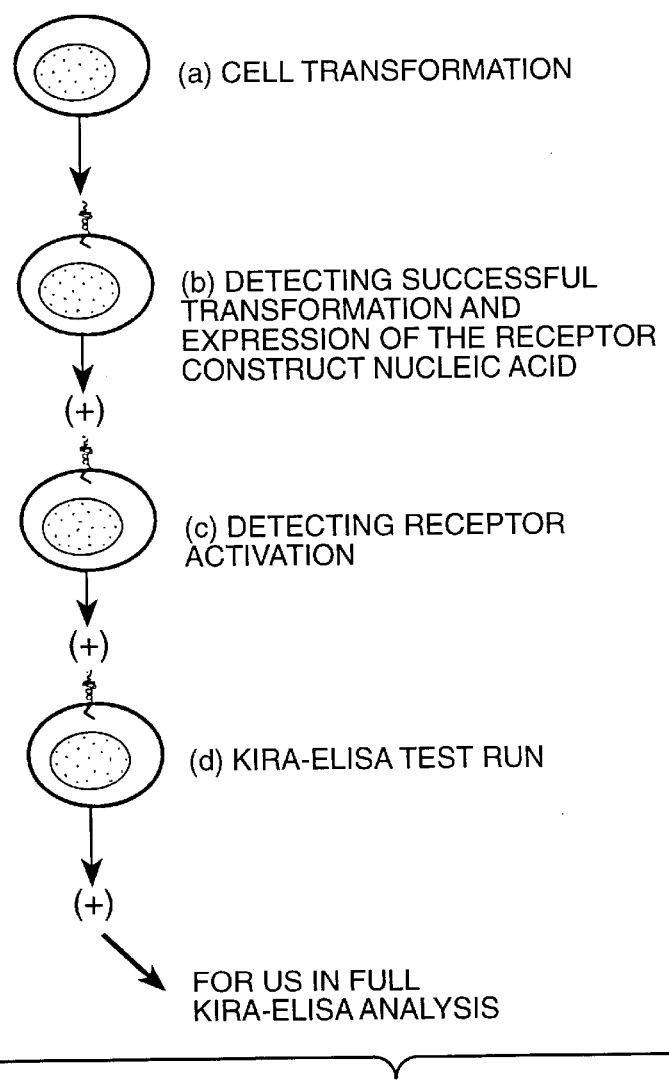
FIG._4

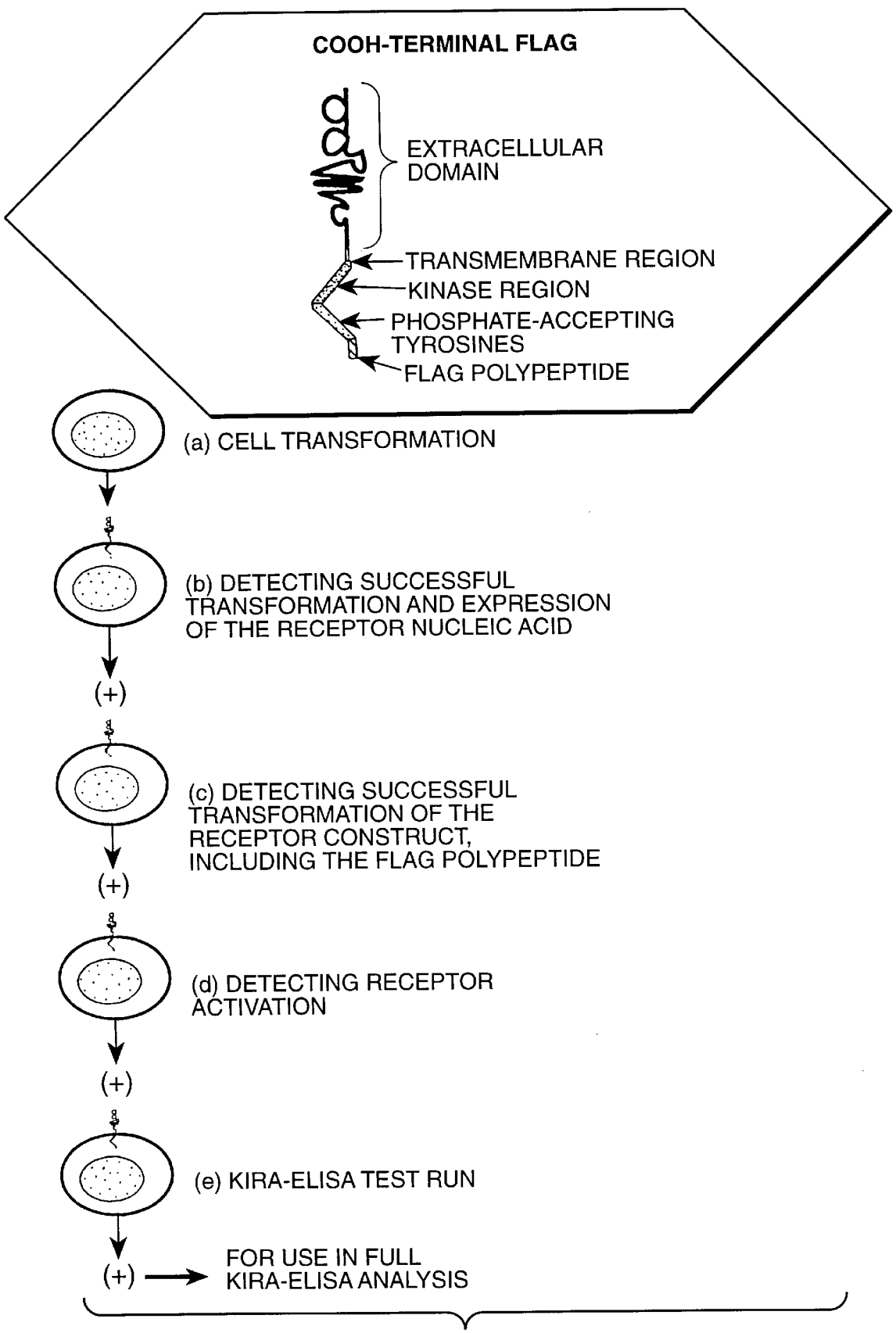
FIG._5

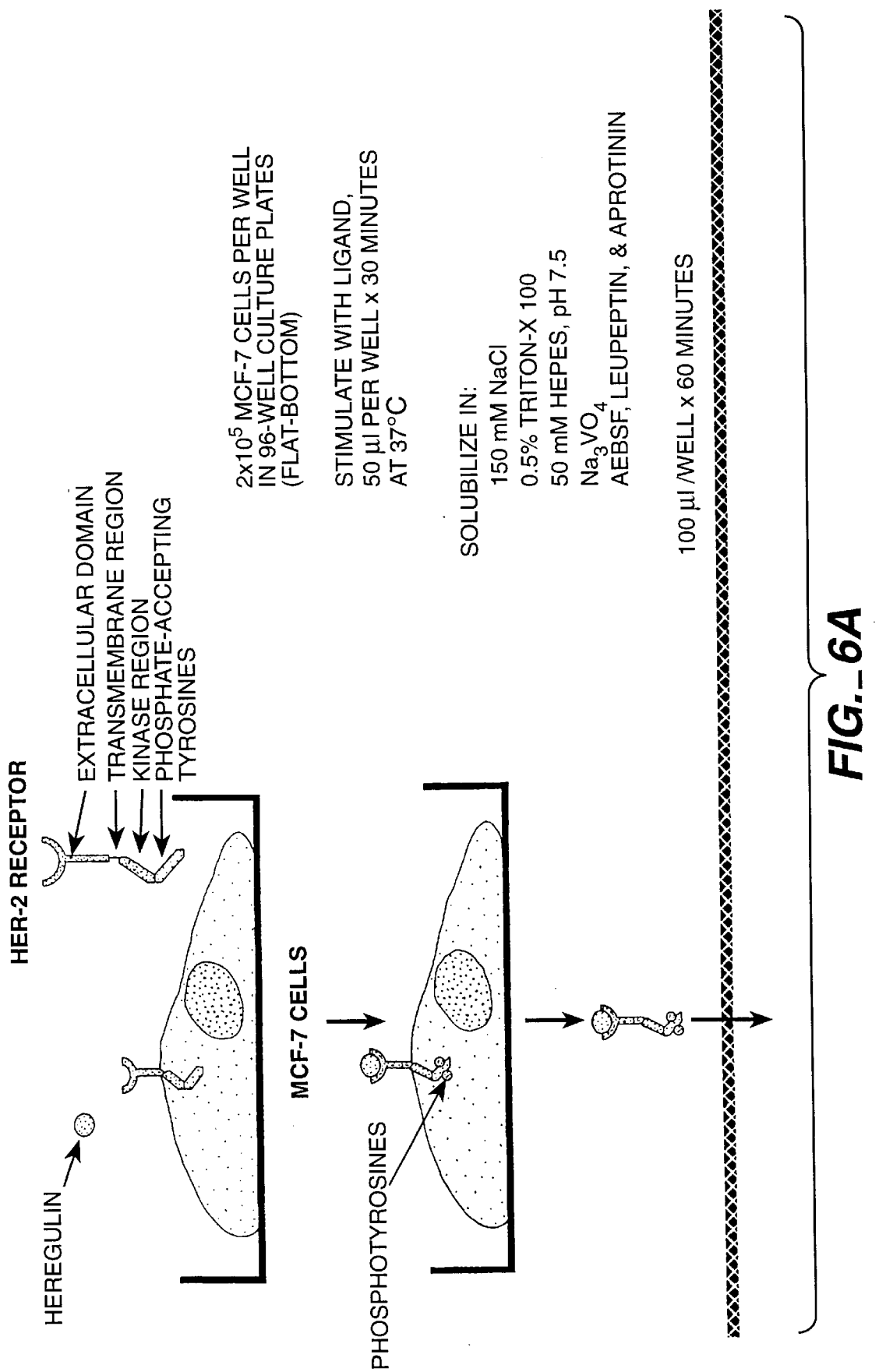
FIG._6A

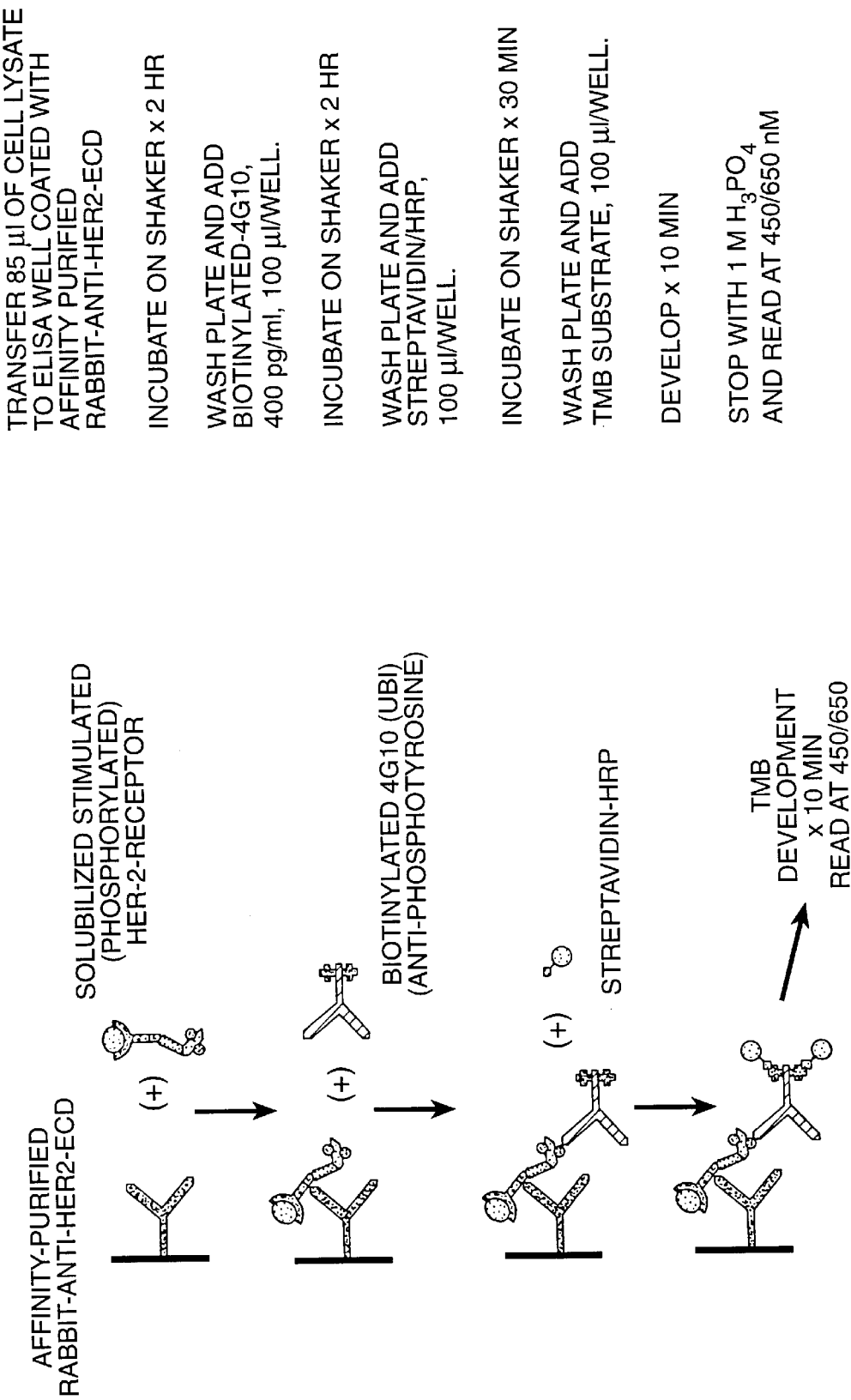
FIG._6B

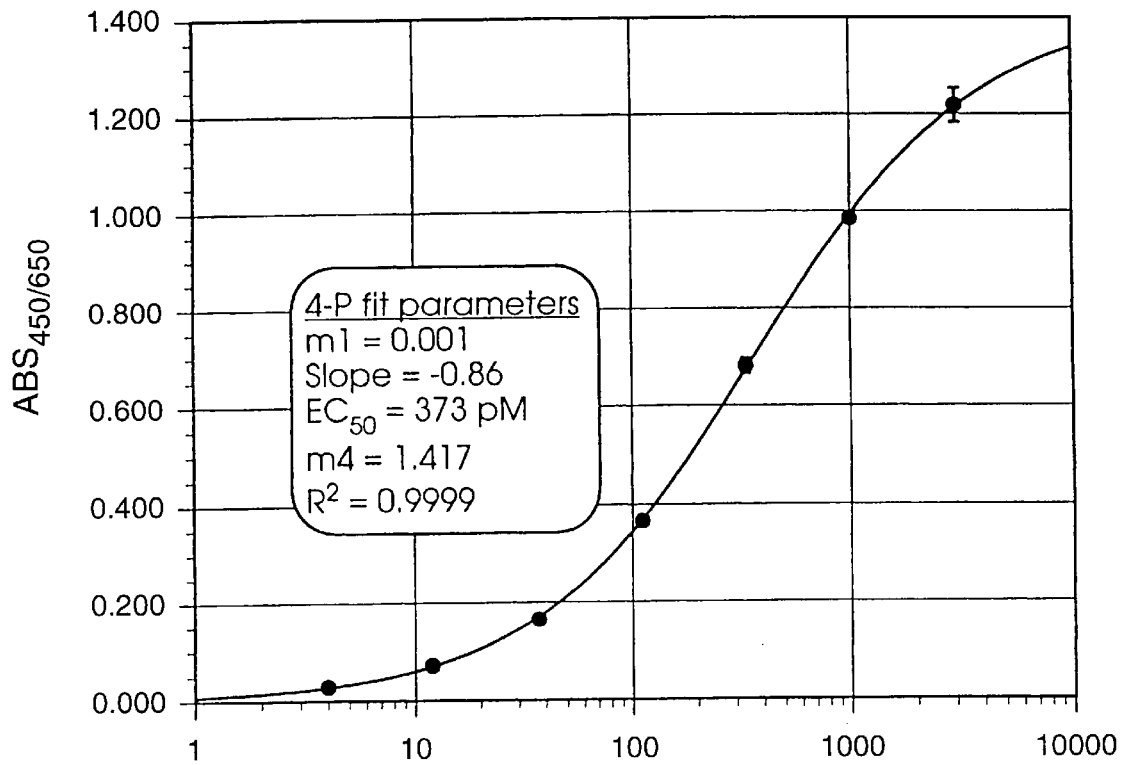
FIG._7
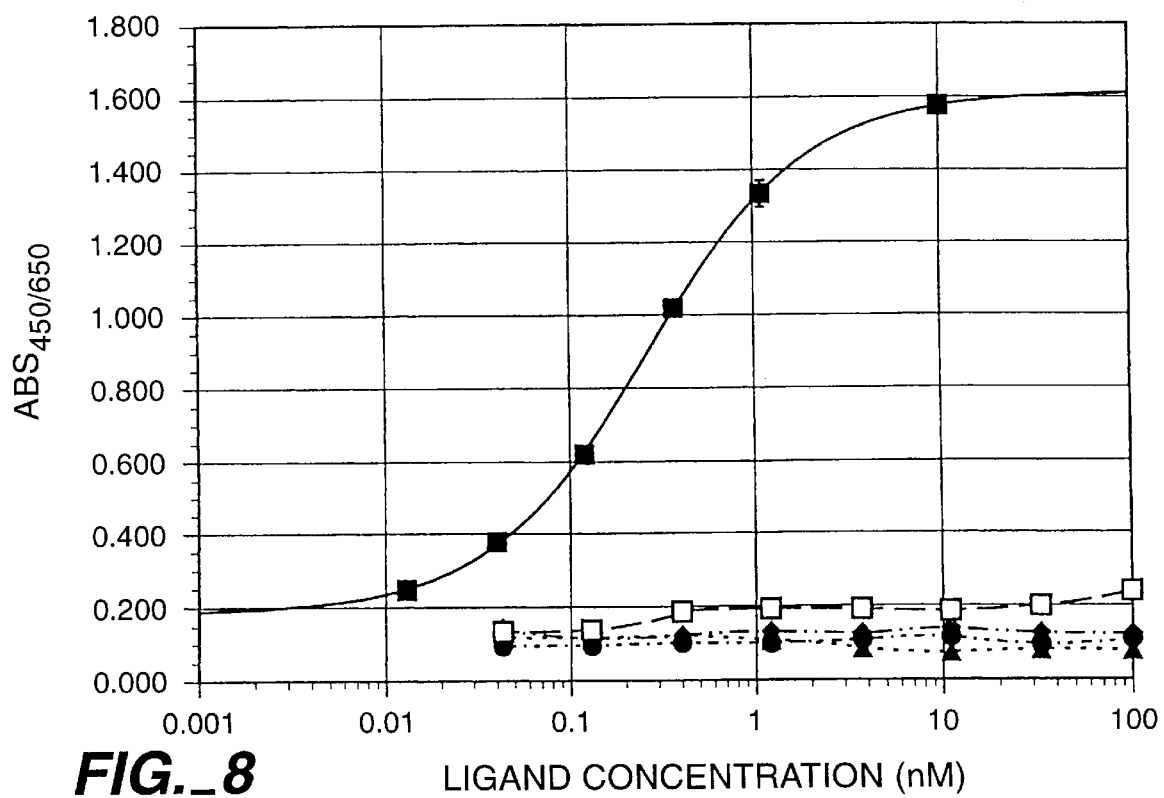
FIG._8

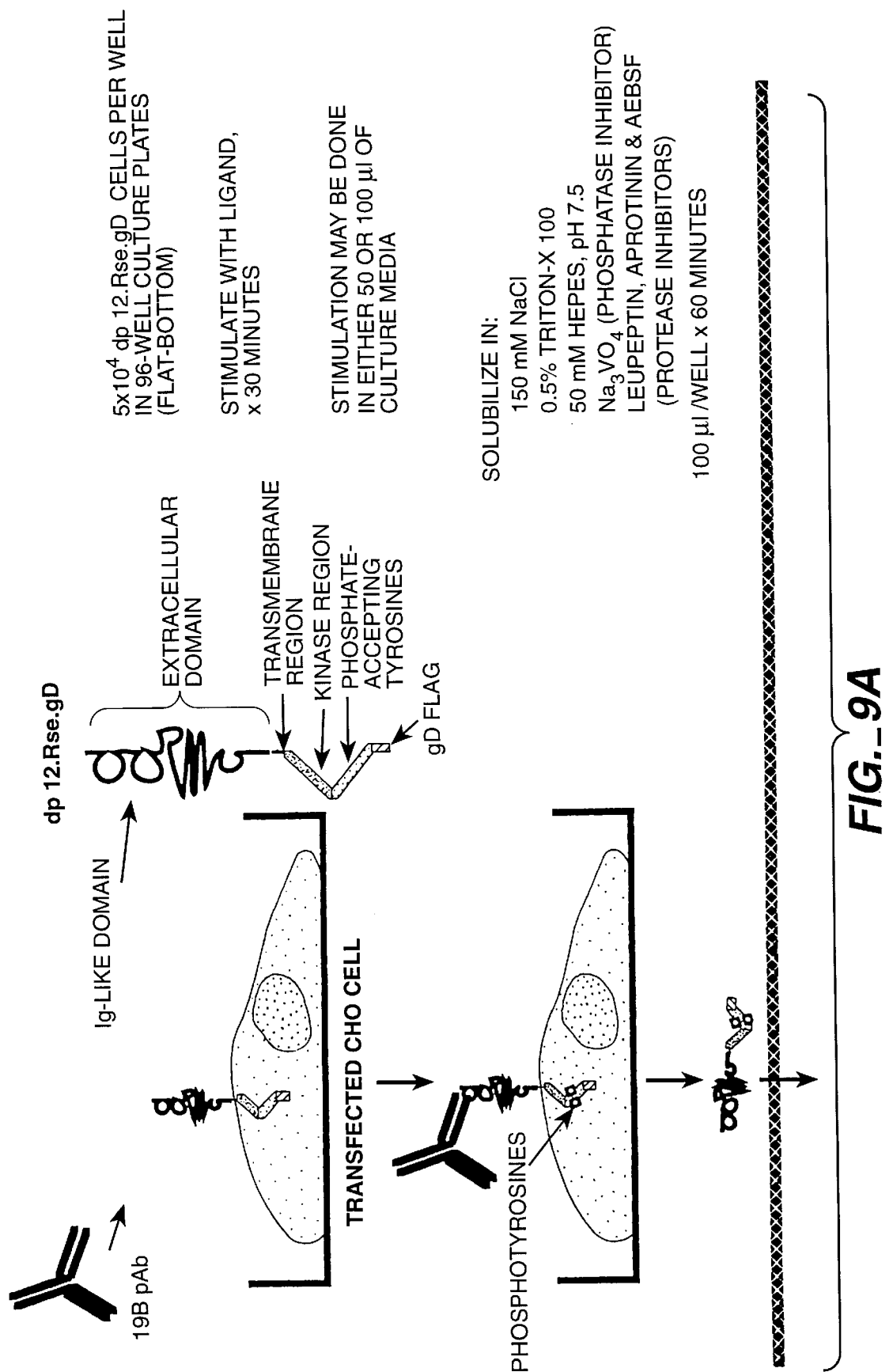
FIG._9A

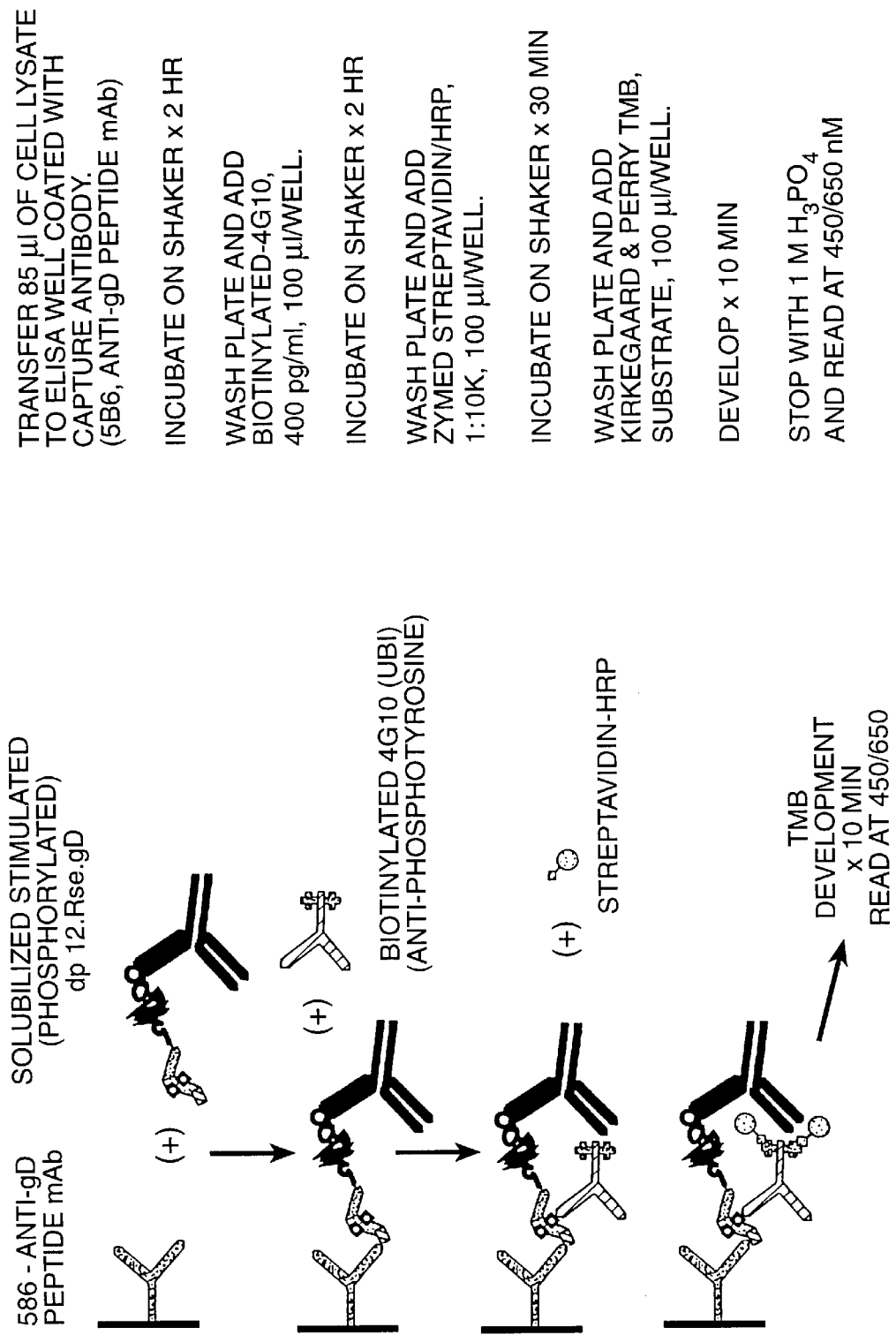
FIG._9B

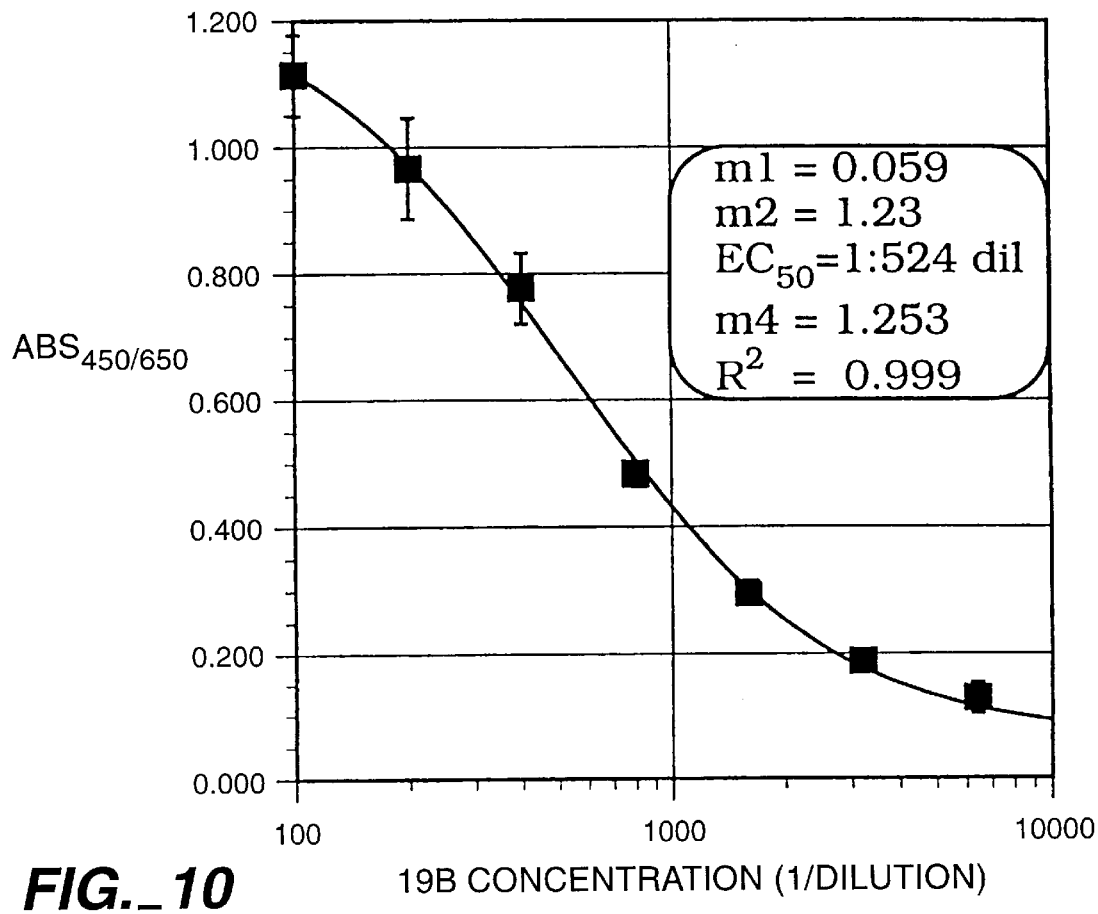
FIG._10
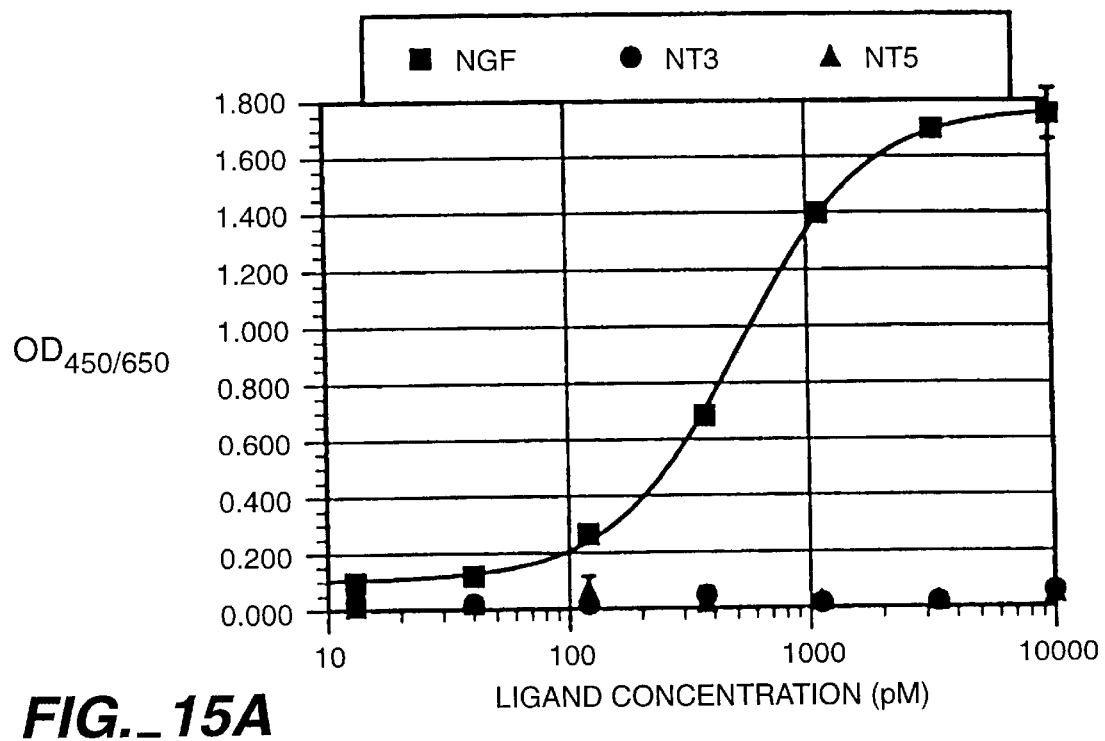
FIG._15A

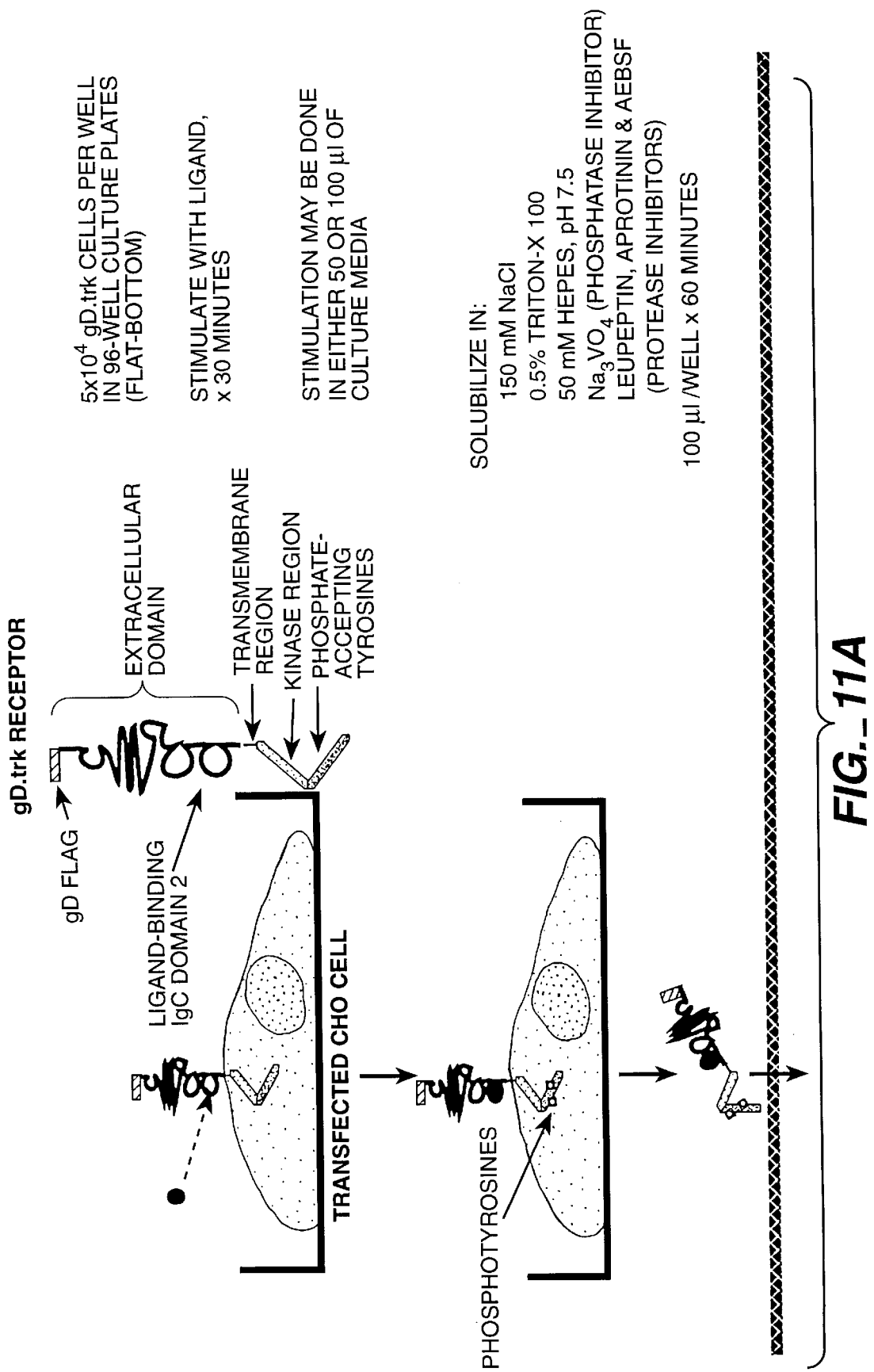
FIG._11A

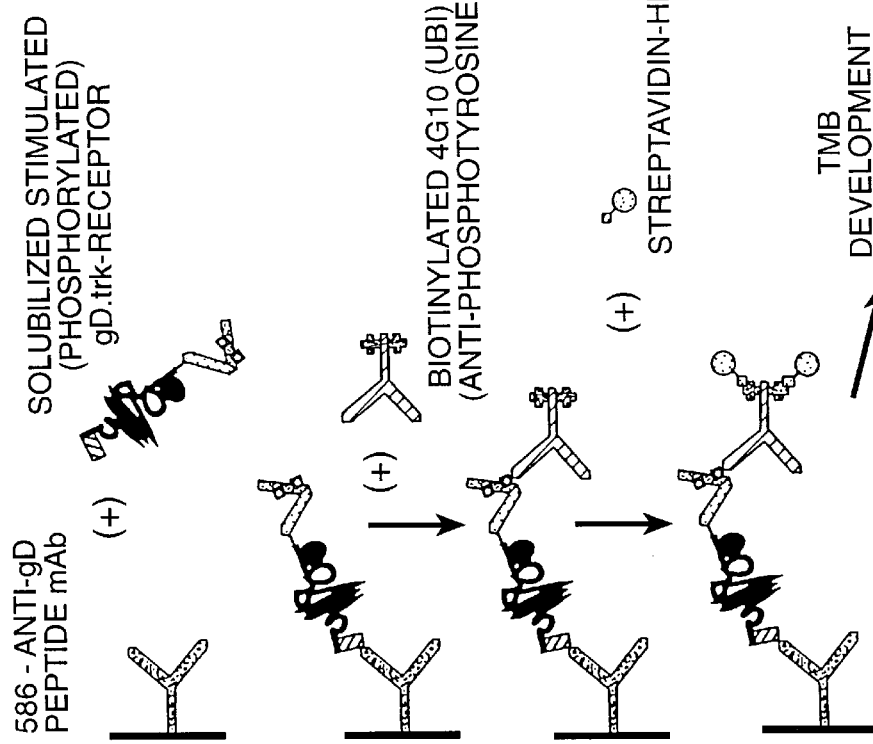
FIG._11B

```
                ^sp6 RNA start
 841  TATAGAATAA CATCCACTTT GCCTTTCTCT CCACAGGTGT CCACTCCCAG GTCCAACTGC
      ATATCTTATT GTAGGTGAAA CGGAAAGAGA GGTGTCCACA GGTGAGGGTC CAGGTTGACG ^cloning linker
           ^R1 site mutated in
              ^begin gD from pchadII
 901  ACCTGAATTC CACTGCCTTC CACCAAGCTC TGCAGGATCC CAGAGTCAGG GGTCTGTATC
      TGGACTTAAG GTGACGGAAG GTGGTTCGAG ACGTCCTAGG GTCTCAGTCC CCAGACATAG 961  TTCCTGCTGG TGGCTCCAGT TCAGGAACAG TAAACCCTGC TCCGAATATT GCCTCTCACA
      AAGGACGACC ACCGAGGTCA AGTCCTTGTC ATTTGGGACG AGGCTTATAA CGGAGAGTGT 1021  TCTCGTCAAT CTCCGCGAGG ACTGGGGACC CTGTGACAAG CTTCAGCGCG AACGACCAAC
      AGAGCAGTTA GAGGCGCTCC TGACCCCTGG GACACTGTTC GAAGTCGCGC TTGCTGGTTG ^Start gD
                                                      M* G* G*
   1                                                  GTATGGGGGG
1081  TACCCCGATC ATCAGTTATC CTTAAGGTCT CTTTTGTGTG GTGCGTTCCG GTATGGGGGG
      ATGGGGCTAG TAGTCAATAG GAATTCCAGA GAAAACACAC CACGCAAGGC CATACCCCCC T* A* A* R* L* G* A* V* I* L* F* V* V* I* V* G* L* H* G* V*
   4  GACTGCCGCC AGGTTGGGGG CCGTGATTTT GTTTGTCGTC ATAGTGGGCC TCCATGGGGT
      CTGACGGCGG TCCAACCCCC GGCACTAAAA CAAACAGCAG TATCACCCGG AGGTACCCCA R* G* K* Y* A* L* A  D  A  S  L  K  M  A  D  P  N  R  F  R
  24  CCGGGGCAAA TATGCCTTGG CGGATGCCTC TCTCAAGATG GCCGACCCCA ATCGATTTCG
      GGCGCCGTTT ATACGGAACC GCCTACGGAG AGAGTTCTAC CGGCTGGGGT TAGCTAAAGC
```

FIG.-12A

```
                                            ^Xho and GTA mutated in
                                            ^begin mature trkA
       G  K  D     L  P  V  L     D  Q  L     L  E  V     A  A  P  C     P  D  A
  44   CGGCAAAGAC  CTTCCGGTCC  TGGACCAGCT  GCTCGAGGTA  GCCGCACCCT  GCCCCGATGC
1261   GCCGTTTCTG  GAAGGCCAGG  ACCTGGTCGA  CGAGCTCCAT  CGGCGTGGGA  CGGGGCTACG C  C  P     H  G  S  S     G  L  R     C  T  R     D  G  A  L     D  S  L
  64   CTGCTGCCCC  CACGGCTCCT  CGGGACTGCG  ATGCACCCGG  GATGGGGCCC  TGGATAGCCT
1321   GACGACGGGG  GTGCCGAGGA  GCCCTGACGC  TACGTGGGCC  CTACCCCGGG  ACCTATCGGA H  H  L     P  G  A  E     N  L  T     E  L  Y     I  E  N  Q     Q  H  L
  84   CCACCACCTG  CCCGGCGCAG  AGAACCTGAC  TGAGCTCTAC  ATCGAGAACC  AGCAGCATCT
1381   GGTGGTGGAC  GGGCCGCGTC  TCTTGGACTG  ACTCGAGATG  TAGCTCTTGG  TCGTCGTAGA Q  H  L     E  L  R  D     L  R  G     L  G  E     L  R  N  L     T  I  V
 104   GCAGCATCTG  GAGCTCCGTG  ATCTGAGGGG  CCTGGGGGAG  CTGAGAAACC  TCACCATCGT
1441   CGTCGTAGAC  CTCGAGGCAC  TAGACTCCCC  GGACCCCCTC  GACTCTTTGG  AGTGGTAGCA K  S  G     L  R  F  V     A  P  D     A  F  H     F  T  P  R     L  S  R
 124   GAAGAGTGGT  CTCCGTTTCG  TGGCGCCAGA  TGCCTTCCAT  TTCACTCCTC  GGCTCAGTCG
1501   CTTCTCACCA  GAGGCAAAGC  ACCGCGGTCT  ACGGAAGGTA  AAGTGAGGAG  CCGAGTCAGC L  N  L     S  F  N  A     L  E  S     L  S  W     K  T  V  Q     G  L  S
 144   CCTGAATCTC  TCCTTCAACG  CTCTGGAGTC  TCTCTCCTGG  AAAACTGTGC  AGGGCCTCTC
1561   GGACTTAGAG  AGGAAGTTGC  GAGACCTCAG  AGAGAGGACC  TTTTGACACG  TCCCGGAGAG L  Q  E     L  V  L  S     G  N  P     L  H  C     S  C  A  L     R  W  L
 164   CTTACAGGAA  CTGGTCCTGT  CGGGGAACCC  TCTGCACTGT  TCTTGTGCCC  TGCGCTGGCT
1621   GAATGTCCTT  GACCAGGACA  GCCCCTTGGG  AGACGTGACA  AGAACACGGG  ACGCGACCGA
```

*FIG._12B*

```
184   Q   R   W   E   E   E   G   L   G   G   V   P   E   Q   K   L   Q   C   H   G
1681  ACAGCGCTGG GAGGAGGAGG GACTGGGCGG AGTGCCTGAA CAGAAGCTGC AGTGTCATGG
      TGTCGCGACC CTCCTCCTCC CTGACCCGCC TCACGGACTT GTCTTCGACG TCACAGTACC

204   Q   G   P   L   A   H   M   P   N   A   S   C   G   V   P   T   L   K   V   Q
1741  GCAAGGGCCC CTGGCCCACA TGCCCAATGC CAGCTGTGGT GTGCCCACGC TGAAGGTCCA
      CGTTCCCGGG GACCGGGTGT ACGGGTTACG GTCGACACCA CACGGGTGCG ACTTCCAGGT

224   V   P   N   A   S   V   D   V   G   D   D   V   L   L   R   C   Q   V   E   G
1801  GGTGCCCAAT GCCTCGGTGG ATGTGGGGGA CGACGTGCTG CTGCGGTGCC AGGTGGAGGG
      CCACGGGTTA CGGAGCCACC TACACCCCCT GCTGCACGAC GACGCCACGG TCCACCTCCC

244   R   G   L   E   Q   A   G   W   I   L   T   E   L   E   Q   S   A   T   V   M
1861  GCGGGGCCTG GAGCAGGCCG GCTGGATCCT CACAGAGCTG GAGCAGTCAG CCACGGTGAT
      CGCCCCGGAC CTCGTCCGGC CGACCTAGGA GTGTCTCGAC CTCGTCAGTC GGTGCCACTA

264   K   S   G   G   L   P   S   L   G   L   T   L   A   N   V   T   S   D   L   N
1921  GAAATCTGGG GGTCTGCCAT CCCTGGGGCT GACCCTGGCC AATGTCACCA GTGACCTCAA
      CTTTAGACCC CCAGACGGTA GGGACCCCGA CTGGGACCGG TTACAGTGGT CACTGGAGTT

284   R   K   N   L   T   C   W   A   E   N   D   V   G   R   A   E   V   S   V   Q
1981  CAGGAAGAAC TTGACGTGCT GGGCAGAGAA CGATGTGGGC CGGGCAGAGG TCTCTGTTCA
      GTCCTTCTTG AACTGCACGA CCCGTCTCTT GCTACACCCG GCCCGTCTCC AGAGACAAGT

304   V   N   V   S   F   P   A   S   V   Q   L   H   T   A   V   E   M   H   H   W
2041  GGTCAACGTC TCCTTCCCGG CCAGTGTGCA GCTGCACACG GCGGTGGAGA TGCACCACTG
      CCAGTTGCAG AGGAAGGGCC GGTCACACGT CGACGTGTGC CGCCACCTCT ACGTGGTGAC
```

FIG._12C

```
184  Q   R   W   E   E   G   L   G   G   V   P   E   Q   K   L   Q   C   H   G
1681 ACAGCGCTGG GAGGAGGAGG GACTGGGGCGG AGTGCCTGAA CAGAAGCTGC AGTGTCATGG
     TGTCGCGACC CTCCTCCTCC CTGACCCCGCC TCACGGACTT GTCTTCGACG TCACAGTACC

204  Q   G   P   L   A   H   M   P   N   A   S   C   G   V   P   T   L   K   V   Q
1741 GCAAGGGCCC CTGGCCACA  TGCCCAATGC CAGCTGTGGT GTGCCCACGC TGAAGGTCCA
     CGTTCCCGGG GACCGGGTGT ACGGGTTACG GTCGACACCA CACGGGTGCG ACTTCCAGGT

224  V   P   N   A   S   V   D   V   G   D   D   V   L   L   R   C   Q   V   E   G
1801 GGTGCCCAAT GCCTCGGTGG ATGTGGGGGA CGACGTGCTG CTGCGGTGCC AGGTGGAGG
     CCACGGGTTA CGGAGCCACC TACACCCCCT GCTGCACGAC GACGCCACGG TCCACCTCCC

244  R   G   L   E   Q   A   G   W   I   L   T   E   L   E   Q   S   A   T   V   M
1861 GCGGGGCCTG GAGCAGGCCG GCTGGATCCT CACAGAGCTG GAGCAGTCAG CCACGGTGAT
     CGCCCCGGAC CTCGTCCGGC CGACCTAGGA GTGTCTCGAC CTCGTCAGTC GGTGCCACTA

264  K   S   G   G   L   P   S   L   G   L   T   L   A   N   V   T   S   D   L   N
1921 GAAATCTGGG GGTCTGCCAT CCCTGGGGCT GACCCTGGCC AATGTCACCA GTGACCTCAA
     CTTTAGACCC CCAGACGGTA GGGACCCCGA CTGGGACCGG TTACAGTGGT CACTGGAGTT

284  R   K   N   L   T   C   W   A   E   N   D   V   G   R   A   E   V   S   V   Q
1981 CAGGAAGAAC TTGACGTGCT GGGCAGAGAA CGATGTGGGC CGGGCAGAGG TCTCTGTTCA
     GTCCTTCTTG AACTGCACGA CCCGTCTCTT GCTACACCCG GCCCGTCTCC AGAGACAAGT

304  V   N   V   S   F   P   A   L   H   T   A   V   E   M   H   H   W
2041 GGTCAACGTC TCCTTCCCGG CCAGTGTGCA GCTGCACACG GCGGTGGAGA TGCACCACTG
     CCAGTTGCAG AGGAAGGGCC GGTCACACGT CGACGTGTGC CGCCACCTCT ACGTGGTGAC
```

FIG. _12D

```
464   N   K   F       G   I   N   R       P   A   V       L   A   P       E   D   G   L       A   M   S
2521  AAACAAGTTT  GGGATCAACC  GCCCGGCTGT  GCTGGCTCCA  GAGGATGGGC  TGGCCATGTC
      TTTGTTCAAA  CCCTAGTTGG  CGGGCCGACA  CGACCGAGGT  CTCCTACCCG  ACCGGTACAG

484   L   H   F       M   T   L   G       G   S   S       L   S   P       T   E   G   K       G   S   G
2581  CCTGCATTTC  ATGACATTGG  GTGGCAGCTC  CCTGTCCCCC  ACCGAGGGCA  AAGGCTCTGG
      GGACGTAAAG  TACTGTAACC  CACCGTCGAG  GGACAGGGGG  TGGCTCCCGT  TTCCGAGACC

504   L   Q   G       H   I   I   E       N   P   Q       Y   F   S       D   A   C   V       H   H   I
2641  GCTCCAAGGC  CACATCATCG  AGAACCCACA  ATACTTCAGT  GATGCCTGTG  TTCACCACAT
      CGAGGTTCCG  GTGTAGTAGC  TCTTGGGTGT  TATGAAGTCA  CTACGGACAC  AAGTGGTGTA

524   K   R   R       D   I   V   L       K   W   E       L   G   E       G   A   F   G       K   V   F
2701  CAAGCGCCGG  GACATCGTGC  TCAAGTGGGA  GCTGGGGGAG  GGCGCCTTTG  GAAAGGTCTT
      GTTCGCGGCC  CTGTAGCACG  AGTTCACCCT  CGACCCCCTC  CCGCGGAAAC  CCTTCCAGAA

544   L   A   E       C   H   N   L       L   P   E       Q   D   K       M   L   V   A       V   K   A
2761  CCTTGCTGAG  TGCCACAACC  TCCTGCCTGA  GCAGGACAAG  ATGCTGGTGG  CTGTCAAGGC
      GGAACGACTC  ACGGTGTTGG  AGGACGGACT  CGTCCTGTTC  TACGACCACC  GACAGTTCCG

564   L   K   E       A   S   E   S       A   R   Q       D   F   Q       R   E   A   E       L   L   T
2821  ACTGAAGGAG  GCGTCCGAGA  GTGCTCGGCA  GGACTTCCAA  CGTGAGGCTG  AGCTGCTCAC
      TGACTTCCTC  CGCAGGCTCT  CACGAGCCGT  CCTGAAGGTT  GCACTCCGAC  TCGACGAGTG

584   M   L   Q       H   Q   H   I       V   R   F       F   G   V       C   T   E   G       R   P   L
2881  CATGCTGCAG  CACCAGCACA  TCGTGCGCTT  CTTCGGCGTC  TGCACCGAGG  GCCGCCCCCT
      GTACGACGTC  GTGGTCGTGT  AGCACGCGAA  GAAGCCGCAG  ACGTGGCTCC  CGGCGGGGGA
```

FIG.-12E

```
604  L   M   V   F   E   Y   M   R   H   G   D   L   N   R   F   L   R   S   H   G
2941 GCTCATGGTC TTTGAGTATA TGCGGCACGG GGACCTCAAC CGCTTCCTCC GATCCCATGG
     CGAGTACCAG AAACTCATAT ACGCCGTGCC CCTGGAGTTG GCGAAGGAGG CTAGGGTACC

624  P   D   A   K   L   L   A   G   G   E   D   V   A   P   G   P   L   G   L   G
3001 ACCTGATGCC AAGCTGCTGG CTGGTGGGGA GGATGTGGCT CCAGGCCCCC TGGGTCTGGG
     TGGACTACGG TTCGACGACC GACCACCCCT CCTACACCGA GGTCCGGGGG ACCCAGACCC

644  Q   L   L   A   V   A   S   Q   V   A   A   G   M   V   Y   L   A   G   L   H
3061 GCAGCTGCTG GCCGTGGCTA GCCAGGTCGC TGCGGGGATG GTGTACCTGG CGGGTCTGCA
     CGTCGACGAC CGGCACCGAT CGGTCCAGCG ACGCCCCTAC CACATGGACC GCCCAGACGT

664  F   V   H   R   D   L   A   T   R   N   C   L   V   G   Q   G   L   V   V   K
3121 TTTTGTGCAC CGGGACCTGG CCACACGCAA CTGTCTAGTG GGCCAGGGAC TGGTGGTCAA
     AAAACACGTG GCCCTGGACC GGTGTGCGTT GACAGATCAC CCGGTCCCTG ACCACCAGTT

684  I   G   D   F   G   M   S   R   D   I   Y   S   T   D   Y   Y   R   V   G   G
3181 GATTGGTGAT TTTGGCATGA GCAGGGATAT CTACAGCACC GACTATTACC GTGTGGGAGG
     CTAACCACTA AAACCGTACT CGTCCCTATA GATGTCGTGG CTGATAATGG CACACCCTCC

704  R   T   M   L   P   I   R   W   M   P   P   E   S   I   L   Y   R   K   F   T
3241 CCGCACCATG CTGCCCATTC GCTGGATGCC GCCCGAGAGC ATCCTGTACC GTAAGTTCAC
     GGCGTGGTAC GACGGGTAAG CGACCTACGG CGGGCTCTCG TAGGACATGG CATTCAAGTG

724  T   E   S   D   V   W   S   F   G   V   V   L   W   E   I   F   T   Y   G   K
3301 CACCGAGAGC GACGTGTGGA GCTTCGGGGT GGTGCTCTGG GAGATCTTCA CCTACGGCAA
     GTGGCTCTCG CTGCACACCT CGAAGCCCCA CCACGAGACC CTCTAGAAGT GGATGCCGTT

```
3361  GCAGCCCTGG TACCAGCTCT CCAACACGGA GGCAATCGAC TGCATCACGC AGGGACGTGA
      CGTCGGGACC ATGGTCGAGA GGTTGTGCCT CCGTTAGCTG ACGTAGTGCG TCCCTGCACT

764       L   E   R     P   R   A   C     P   P   E     V   Y   A     I   M   R   G     C   W   Q
3421  GTTGGAGCGG CCACGTGCCT GCCCACCAGA GGTCTACGCC ATCATGCGGG GCTGCTGGCA
      CAACCTCGCC GGTGCACGGA CGGGTGGTCT CCAGATGCGG TAGTACGCCC CGACGACCGT

784       R   E   P     Q   Q   R   H     S   I   K     D   V   H     A   R   L   Q     A   L   A
3481  GCGGGAGCCC CAGCAACGCC ACAGCATCAA GGATGTGCAC GCCCGGCTGC AAGCCCTGGC
      CGCCCTCGGG GTCGTTGCGG TGTCGTAGTT CCTACACGTG CGGGCCGACG TTCGGGACCG

R1 site added with cloning primer^
                  R1 site removed with cut and fill^

804       Q   A   P     P   V   Y   L     D   V   L     G   O
3541  CCAGGCACCT CCTGTCTACC TGGATGTCCT GGGCTAGAAT TAATTCAATC GATGGCCGCC
      GGTCCGTGGA GGACAGATGG ACCTACAGGA CCCGATCTTA ATTAAGTTAG CTACCGGCGG

^sv40 early poly A
3601  ATGGCCCAAC TTGTTTATTG CAGCTTATAA TGGTTACAAA TAAAGCAATA GCATCACAAA
      TACCGGGTTG AACAAATAAC GTCGAATATT ACCAATGTTT ATTTCGTTAT CGTAGTGTTT
```

*FIG._12G*

```
            ^sp6 RNA start
 841  TATAGAATAA CATCCACTTT GCCTTTCTCT CCACAGGTGT CCACTCCCAG GTCCAACTGC
      ATATCTTATT GTAGGTGAAA CGGAAAGAGA GGTGTCCACA GGTGAGGGTC CAGGTTGACG ^cloning linker    ^begin gD from pchadII
 901  ACCTCGGTTC TATCGATTGA ATTCCACCAA GCTCTGCAGG CTTCCACTGC ATCCCAGAGT
      TGGAGCCAAG ATAGCTAACT TAAGGTGGTT CGAGACGTCC GAAGGTGACG TAGGGTCTCA 961  CAGGGGTCTG TATCTTCCTG CTGGTGGCTC CAGTTCAGGA ACAGTAAACC CTGCTCCGAA
      GTCCCCAGAC ATAGAAGGAC GACCACCGAG GTCAAGTCCT TGTCATTTGG GACGAGGCTT 1021  TATTGCCTCT CACATCTCGT CAATCTCCGC GAGGACTGGG GACCCTGTGA CAAGCTTCAG
      ATAACGGAGA GTGTAGAGCA GTTAGAGGCG CTCCTGACCC CTGGGACACT GTTCGAAGTC 1081  CGGAACGAC  CAACTACCCC GATCATCAGT TATCCTTAAG GTCTCTTTTG TGTGGTGCGT
      GCGCTTGCTG GTTGATGGGG CTAGTAGTCA ATAGGAATTC CAGAGAAAAC ACACCACGCA ^Start gD
  1        M* G* G* T* A*    A* R* L*    G* A* V* I*    L* F* V*    V* I* V*
 1141 TCCGGTATGG GGGGACTGC  CGCCAGGTTG GGGGCCGTGA TTTTGTTTGT CGTCATAGTG
      AGGCCATACC CCCCCTGACG GCGGTCCAAC CCCCGGCACT AAAACAAACA GCAGTATCAC 19   G* L* H* G*    V* R* G*    K* Y* A*    L* A D A S L K    M A D
 1201 GGCCTCCATG GGGTCCGGG CAAATATGCC TTGGCGGATG CCTCTCTCAA GATGGCCGAC
      CCGGAGGTAC CCCAGGCCC GTTTATACGG AACCGCCTAC GGAGAGAGTT CTACCGGCTG
```

FIG._13A

```
                              xho and GTA mutated in^
                                            start mature trkB^
 39   P   N   R   F   R   G   K   D   L   P   V   L   D   Q   L   E   V   C   P
1261 CCCAATCGAT TTCGCGGCAA AGACCTTCCG GTCCTGGACC AGCTGCTCGA GGTATGTCCC
     GGGTTAGCTA AAGCGCCGTT TCTGGAAGGC CAGGACCTGG TCGACGAGCT CCATACAGGG 59   T   S   C   K   C   S   A   S   R   I   W   C   S   D   P   S   P   G   I   V
1321 ACGTCCTGCA AATGCAGTGC CTCTCGGATC TGGTGCAGCG ACCCTTCTCC TGGCATCGTG
     TGCAGGACGT TTACGTCACG GAGAGCCTAG ACCACGTCGC TGGGAAGAGG ACCGTAGCAC 79   A   F   P   R   L   E   P   N   S   V   D   P   E   N   I   T   E   I   F   I
1381 GCATTTCCGA GATTGGAGCC TAACAGTGTA GATCCTGAGA ACATCACCGA AATTTTCATC
     CGTAAAGGCT CTAACCTCGG ATTGTCACAT CTAGGACTCT TGTAGTGGCT TTAAAAGTAG 99   A   N   Q   K   R   L   E   I   I   N   E   D   D   V   E   A   Y   V   G   L
1441 GCAAACCAGA AAAGGTTAGA AATCATCAAC GAAGATGATG TTGAAGCTTA TGTGGGACTG
     CGTTTGGTCT TTTCCAATCT TTAGTAGTTG CTTCTACTAC AACTTCGAAT ACACCCTGAC 119   R   N   L   T   I   V   D   S   G   L   K   F   V   A   H   K   A   F   L   K
1501 AGAAATCTGA CAATTGTGGA TTCTGGATTA AAATTTGTGG CTCATAAAGC ATTTCTGAAA
     TCTTTAGACT GTTAACACCT AAGACCTAAT TTTAAACACC GAGTATTTCG TAAAGACTTT 139   N   S   N   L   Q   H   I   N   F   T   R   N   K   L   T   S   L   S   R   K
1561 AACAGCAACC TGCAGCACAT CAATTTTACC CGAAACAAAC TGACGAGTTT GTCTAGGAAA
     TTGTCGTTGG ACGTCGTGTA GTTAAAATGG GCTTTGTTTG ACTGCTCAAA CAGATCCTTT 159   H   F   R   H   L   D   L   S   E   L   I   L   V   G   N   P   F   T   C   S
1621 CATTTCCGTC ACCTTGACTT GTCTGAACTG ATCCTGGTGG GCAATCCATT TACATGCTCC
     GTAAAGGCAG TGGAACTGAA CAGACTTGAC TAGGACCACC CGTTAGGTAA ATGTACGAGG
```

*FIG._13B*

```
179  C   D   I   M   W   I   K   T   L   Q   E   A   K   S   S   P   D   T   Q   D
1681 TGTGACATTA TGTGGATCAA ACACCTAGTT GACTCTCCAA GAGGCTAAAT CCAGTCCAGA CACTCAGGAT
     ACACTGTAAT ACACCTAGTT                                                              
     (complementary strand)

199  L   Y   C   L   N   E   S   S   K   N   I   P   L   A   N   L   Q   I   P   N
1741 TTGTACTGCC TGAATGAAAG CAGCAAGAAT ATTCCCCTGG CAAACCTGCA GATACCCAAT
     AACATGACGG ACTTACTTTC GTCGTTCTTA TAAGGGGACC GTTTGGACGT CTATGGGTTA

219  C   G   L   P   S   A   N   L   A   A   P   N   L   T   V   E   E   G   K   S
1801 TGTGGTTTGC CATCTGCAAA TCTGGCCGCA CCTAACCTCA CTGTGGAGGA AGGAAAGTCT
     ACACCAAACG GTAGACGTTT AGACCGGCGT GGATTGGAGT GACACCTCCT TCCTTTCAGA

239  I   T   L   S   C   S   V   A   G   D   P   V   P   N   M   Y   W   D   V   G
1861 ATCACATTAT CCTGTAGTGT GGCAGGTGAT CCGGTTCCTA ATATGTATTG GGATGTTGGT
     TAGTGTAATA GGACATCACA CCGTCCACTA GGCCAAGGAT TATACATAAC CCTACAACCA

259  N   L   V   S   K   H   M   N   E   T   S   H   T   Q   G   S   L   R   I   T
1921 AACCTGGTTT CCAAACATAT GAATGAAACA AGCCACACAC AGGGCTCCTT AAGGATAACT
     TTGGACCAAA GGTTTGTATA CTTACTTTGT TCGGTGTGTG TCCCGAGGAA TTCCTATTGA

279  N   I   S   S   D   D   S   G   K   Q   I   S   C   V   A   E   N   L   V   G
1981 AACATTTCAT CCGATGACAG TGGGAAGCAG ATCTCTTGTG TGGCGGAAAA TCTTGTAGGA
     TTGTAAAGTA GGCTACTGTC ACCCTTCGTC TAGAGAACAC ACCGCCTTTT AGAACATCCT

299  E   D   Q   D   S   V   N   L   T   V   H   F   A   P   T   I   T   F   L   E
2041 GAAGATCAAG ATTCTGTCAA CCTCACTGTG CATTTTGCAC CAACTATCAC ATTTCTCGAA
     CTTCTAGTTC TAAGACAGTT GGAGTGACAC GTAAAACGTG GTTGATAGTG TAAAGAGCTT
```

FIG._13C

```
319  S P T S D H H W C I          P F T V K G N P K P
2101 TCTCCAACCT CAGACCACCA CTGGTGCATT CCATTCACTG TGAAAGGCAA CCCAAAACCA
     AGAGGTTGGA GTCTGGTGGT GACCACGTAA GGTAAGTGAC ACTTTCCGTT GGGTTTTGGT

339  A L Q W F Y N G A I          L N E S K Y I C T K
2161 GCGCTTCAGT GGTTCTATAA CGGGGCAATA TTGAATGAGT CCAAATACAT CTGTACTAAA
     CGCGAAGTCA CCAAGATATT GCCCCGTTAT AACTTACTCA GGTTTATGTA GACATGATTT

359  I H V T N H T E Y H          G C L Q L D N P T H
2221 ATACATGTTA CCAATCACAC GGAGTACCAC GGCTGCCTCC AGCTGGATAA TCCCACTCAC
     TATGTACAAT GGTTAGTGTG CCTCATGGTG CCGACGGAGG TCGACCTATT AGGGTGAGTG

379  M N N G D Y T L I A          K N E Y G K D E K Q
2281 ATGAACAATG GGGACTACAC TCTAATAGCC AAGAATGAGT ATGGGAAGGA TGAGAAACAG
     TACTTGTTAC CCCTGATGTG AGATTATCGG TTCTTACTCA TACCCTTCCT ACTCTTTGTC

399  I S A H F M G W P G          I D D G A N P N Y P
2341 ATTTCTGCTC ACTTCATGGG CTGGCCTGGA ATTGACGATG GTGCAAACCC AAATTATCCT
     TAAAGACGAG TGAAGTACCC GACCGGACCT TAACTGCTAC CACGTTTGGG TTTAATAGGA

419  D V I Y E D Y G T A          A N D I G D T N R
2401 GATGTAATTT ATGAAGATTA TGGAACTGCA GCGAATGACA TCGGGGACAC CAACGAACAGA
     CTACATTAAA TACTTCTAAT ACCTTGACGT CGCTTACTGT AGCCCCTGTG GTGCTTGTCT

439  S N E I P S T D V T          D K T G R E H L S V
2461 AGTAATGAAA TCCCCTTCCAC AGACGTCACT GATAAAACCG GTCGGGAACA TCTCTCGGTC
     TCATTACTTT AGGGAAGGTG TCTGCAGTGA CTATTTTGGC CAGCCCTTGT AGAGAGCCAG

459  Y A V V V I A S V V      L V M L F C L G F L
2521 TATGCTGTGG TGGTGATTGC GTCTGTGGTG CTGGTGATGC TTTTGTGTAAT GCTGTTTCTG
     ATACGACACC ACCACTAACG CAGACACCAC GACCACTACG AAAACCATTA CGACAAAGAC
```

FIG._13D

```
479   L   K   L   A   R   H   S   K   F   G   M   K   G   P   A   S   V   I   S   N
2581  CTTAAGTTGG CAAGACACTC CAAGTTTGGC ATGAAAGGCC CAGCCTCCGT TATCAGCAAT
      GAATTCAACC GTTCTGTGAG GTTCAAACCG TACTTTCCGG GTCGGAGGCA ATAGTCGTTA

499   D   D   D   S   A   S   P   L   H   H   I   S   N   G   S   N   T   P   S   S
2641  GATGATGACT CTGCCAGCCC ACTCCATCAC ATCTCCAATG GGAGTAACAC TCCATCTTCT
      CTACTACTGA GACGGTCGGG TGAGGTAGTG TAGAGGTTAC CCTCATTGTG AGGTAGAAGA

519   S   E   G   G   P   D   A   V   I   I   G   M   T   K   I   P   V   I   E   N
2701  TCGGAAGGTG GCCCAGATGC TGTCATTATT GGAATGACCA AGATCCCTGT CATTGAAAAT
      AGCCTTCCAC CGGGTCTACG ACAGTAATAA CCTTACTGGT TCTAGGGACA GTAACTTTTA

539   P   Q   Y   F   G   I   T   N   S   Q   L   K   P   D   T   F   V   Q   H   I
2761  CCCCAGTACT TTGGCATCAC CAACAGTCAG CTCAAGCCAG ACACCATTGT TCAGCACATC
      GGGGTCATGA AACCGTAGTG GTTGTCAGTC GAGTTCGGTC TGTGTAAACA AGTCGTGTAG

559   K   R   H   N   I   V   L   K   R   E   L   G   E   G   A   F   G   K   V   F
2821  AAGCGACATA ACATTGTTCT GAAAAGGGAG CTAGGCGAAG GAGCCTTTGG AAAAGTGTTC
      TTCGCTGTAT TGTAACAAGA CTTTTCCCTC GATCCGCTTC CTCGGAAACC TTTTCACAAG

579   L   A   E   C   Y   N   L   C   P   E   Q   D   K   I   L   V   A   V   K   T
2881  CTAGCTGAAT GCTATAACCT CTGTCCTGAG CAGGACAAGA TCCTGGTTGC AGTGAAGACC
      GATCGACTTA CGATATTGGA GACAGGACTC GTCCTGTTCT AGGACCAACG TCACTTCTGG

599   L   K   D   A   S   D   N   A   R   K   D   F   H   R   E   A   E   L   L   T
2941  CTGAAGGATG CCAGTGACAA TGCACGCAAG GACTTCCACC GTGAGGCCGA GCTCCTGACC
      GACTTCCTAC GGTCACTGTT ACGTGCGTTC CTGAAGGTGG CACTCCGGCT CGAGGACTGG
```

*FIG._13E*

```
619  N   L   Q   H   E   H   I   V   K   F   Y   G   V   C   V   E   G   D   P   L
3001 AACCTCCAGC ATGAGCACAT CGTCAAGTTC TATGGCGTCT GCGTGGAGGG CGACCCCCTC
     TTGGAGGTCG TACTCGTGTA GCAGTTCAAG ATACCGCAGA CGCACCTCCC GCTGGGGAG

639  I   M   V   F   E   Y   M   K   H   G   D   L   N   K   F   L   R   A   H   G
3061 ATCATGGTCT TTGAGTACAT GAAGCATGGG GACCTCAACA AGTTCCTCAG GGCACACGGC
     TAGTACCAGA AACTCATGTA CTTCGTACCC CTGGAGTTGT TCAAGGAGTC CCGTGTGCCG

659  P   D   A   V   L   M   A   E   G   N   P   P   T   E   L   T   Q   S   Q   M
3121 CCTGATGCCG TGCTGATGGC TGAGGGCAAC CCGCCCACGG AACTGACGCA GTCGCAGATG
     GGACTACGGC ACGACTACCG ACTCCCGTTG GGCGGGTGCC TTGACTGCGT CAGCGTCTAC

679  L   H   I   A   Q   Q   I   A   A   G   M   V   Y   L   A   S   Q   H   F   V
3181 CTGCATATAG CCCAGCAGAT CGCCGCGGGC ATGGTCTACC TGGCGTCCCA GCACTTCGTG
     GACGTATATC GGGTCGTCTA GCGGCGCCCG TACCAGATGG ACCGCAGGGT CGTGAAGCAC

699  H   R   D   L   A   T   R   N   C   L   V   G   E   N   L   L   V   K   I   G
3241 CACCGCGATT TGGCCACCAG GAACTGCCTG GTCGGGGAGA ACTTGCTGGT GAAAATCGGG
     GTGGCGCTAA ACCGGTGGTC CTTGACGGAC CAGCCCCTCT TGAACGACCA CTTTTAGCCC

719  D   F   G   M   S   R   D   V   Y   S   T   D   Y   Y   R   V   G   G   H   T
3301 GACTTTGGGA TGTCCCGGGA CGTGTACAGC ACTGACTACT ACAGGGTCGG TGGCCACACA
     CTGAAACCCT ACAGGGCCCT GCACATGTCG TGACTGATGA TGTCCCAGCC ACCGGTGTGT

739  M   L   P   I   R   W   M   P   P   E   S   I   M   Y   R   K   F   T   T   E
3361 ATGCTGCCCA TTCGCTGGAT GCCTCCAGAG AGCATCATGT ACAGGAAATT CACGACGGAA
     TACGACGGGT AAGCGACCTA CGGAGGTCTC TCGTAGTACA TGTCCTTTAA GTGCTGCCTT

759  S   D   V   W   S   L   G   V   V   L   W   E   I   F   T   Y   G   K   Q   P
3421 AGCGACGTCT GGAGCCTGGG GGTCGTGTTG TGGGAGATT TCACCTATGG CAAACAGCCC
```

FIG.—13F

```
                    TCGCTGCAGA CCTCGGACCC CCAGCACAAC ACCCTCTAAA AGTGGATACC GTTTGTCGGG
779 W  Y  Q  L      S  N  N    E  V  I    E  C  I  T    Q  G  R    V  L  Q
3481 TGGTACCAGC TGTCAAACAA TGAGGTGATA GAGTGTATCA CTCAGGGCCG AGTCCTGCAG
     ACCATGGTCG ACAGTTTGTT ACTCCACTAT CTCACATAGT GAGTCCCGGC TCAGGACGTC

799 R  P  R  T      C  P  Q      E  V  Y    E  L  M  L    G  C  W    Q  R  E
3541 CGACCCCCGCA CGTGCCCCCA GGAGGTGTAT GAGCTGATGC TGGGGTGCTG GCAGCGAGAG
     GCTGGGGCGT GCACGGGGGT CCTCCACATA CTCGACTACG ACCCCACGAC CGTCGCTCTC

819 P  H  M  R      K  N  I      K  G  I      H  T  L  L    Q  N  L    A  K  A
3601 CCCCACATGA GGAAGAACAT CAAGGGCATC CATACCCTCC TTCAGAACTT GGCCAAGGCA
     GGGGTGTACT CCTTCTTGTA GTTCCCGTAG GTATGGGAGG AAGTCTTGAA CCGGTTCCGT

839 S  P  V  Y      L  D  I      L  G  Q
3661 TCTCCGGTCT ACCTGGACAT TCTAGGCTAG GGCCCTTTTC CCCAGACCGA TCCTTCCCAA
     AGAGGCCAGA TGGACCTGTA AGATCCGATC CCGGGAAAAG GGGTCTGGCT AGGAAGGGTT

3721 CGTACTCCTC AGAGGGGCTG AGAGGATGAA CATCTTTTAA CTGCCGCTGG AGGCCACCAA
     GCATGAGGAG TCTGCCCGAC TCTCCTACTT GTAGAAAATT GACGGCGACC TCCGGTGGTT half Xho half Sal site from subcloning^
3781 GCTGCTCTCC TTCACTCTGA CAGTATTAAC ATCAAAGACT CCGAGAAGCT CTCGACCTGC
     CGACGAGAGG AAGTGAGACT GTCATAATTG TAGTTTCTGA GGCTCTTCGA GAGCTGGACG ^sv40 early poly A
3841 AGAAGCTTGG CCGCCATGGC CCAACTTGTT TATTGCAGCT TATAATGGTT ACAAATAAAG
     TCTTCGAACC GGCGGTACCG GGTTGAACAA ATAACGTCGA ATATTACCAA TGTTTATTTC
```

FIG._13G

```
                          ^sp6 RNA start
 841  TATAGAATAA CATCCACTTT GCCTTTCTCT CCACAGGTGT CCACTCCCAG GTCCAACTGC
      ATATCTTATT GTAGGTGAAA CGGAAAGAGA GGTGTCCACA GGTGAGGGTC CAGGTTGACG ^cloning linker
                             ^RI site mutated in
                             ^gD from pchadII
 901  ACCTGAATTC CACTGCCTTC CACCAAGCTC TGCAGGATCC CAGAGTCAGG GGTCTGTATC
      TGGACTTAAG GTGACGGAAG GTGGTTCGAG ACGTCCTAGG GTCTCAGTCC CCAGACATAG 961  TTCCTGCTGG TGGCTCCAGT TCAGGAACAG TAAACCCTGC TCCGAATATT GCCTCTCACA
      AAGGACGACC ACCGAGGTCA AGTCCTTGTC ATTTGGGACG AGGCTTATAA CGGAGAGTGT 1021  TCTCGTCAAT CTCCGCGAGG ACTGGGGACC CTGTGACAAG CTTCAGCGCG AACGACCAAC
      AGAGCAGTTA GAGGCGCTCC TGACCCCTGG GACACTGTTC GAAGTCGCGC TTGCTGGTTG ^Start
 gD                                                   M*  G*  G*
   1
1081  TACCCCGATC ATCAGTTATC CTTAAGGTCT CTTTTGTGTG GTGCGTTCCG GTATGGGGGG
      ATGGGGCTAG TAGTCAATAG GAATTCCAGA GAAAACACAC CACGCAAGGC CATACCCCCC T*  A*  A*  R*  L*  G*  A*  V*  I*  L*  F*  V*  V*  I*  V*  G*  L*  H*  G*  V*
   4
1141  GACTGCCGCC AGGTTGGGGG CCGTGATTTT GTTTGTCGTC CCGGATGCCC TCCATGGGGT
      CTGACGGCGG TCCAACCCCC GGCACTAAAA CAAACAGCAG GGCCTACGGG AGGTACCCCA R*  G*  K*  Y*  A*  L*  A   D   A   S   L   K   M   A   D   P   N   R   F   R
  24
1201  CCGCGGCAAA TATGCCTTGG CGGATGCCTC TCTCAAGATG GCCGACCCCA ATCGATTTCG
      GGCGCCGTTT ATACGGAACC GCCTACGGAG AGAGTTCTAC CGGCTGGGGT TAGCTAAAGC
```

*FIG._14A*

```
                                         ^Xho site and GTA mutated in
                                         ^begin mature trkC
         C    P    A    N    C    V    C
 44  G   K   D   L   P   V   L   D   Q   L   L   E   V
1261 CGGCAAAGAC CTTCCGGTCC TGGACCAGCT GCTCGAGGTA TGCCCCTGCAA ATTGTGTCTG
     GCCGTTTCTG GAAGGCCAGG ACCTGGTCGA CGAGCTCCAT ACGGGACGTT TAACACAGAC 64  S   K   T   E   I   N   C   R   R   P   D   D   G   N   L   F   P   L   L   E
1321 CAGCAAGACT GAGATCAATT GCCGGCGGCC GGACGATGGG AACCTCTTCC CCCTCCTGGA
     GTCGTTCTGA CTCTAGTTAA CGGCCGCCGG CCTGCTACCC TTGGAGAAGG GGGAGGACCT 84  G   Q   D   S   G   N   S   A   N   I   N   I   T   D   I   S   R
1381 AGGGCAGGAT TCAGGGAACA GCAATGGGAA CGCCAATATC AACATCACGG ACATCTCAAG
     TCCCGTCCTA AGTCCCTTGT CGTTACCCTT GCGGTTATAG TTGTAGTGCC TGTAGAGTTC 104  N   I   T   S   I   H   I   E   N   W   R   S   L   H   T   L   N   A   V   D
1441 GAATATCACT TCCATACACA TAGAGAACTG CGCAGTCTT CACACGCTCA ACGCCGTGGA
     CTTATAGTGA AGGTATGTGT ATCTCTTGAC CGCGTCAGAA GTGTGCGAGT TGCGGCACCT 124  M   E   L   Y   T   G   L   Q   K   L   T   I   K   N   S   G   L   R   S   I
1501 CATGGAGCTC TACACCGGAC TTCAAAAGCT GACCATCAAG AACTCAGGAC TTCGGAGCAT
     GTACCTCGAG ATGTGGCCTG AAGTTTTCGA CTGGTAGTTC TTGAGTCCTG AAGCCTCGTA 144  Q   P   R   A   F   A   K   N   P   H   L   R   Y   I   N   L   S   S   N   R
1561 TCAGCCCAGA GCCTTTGCCA AGAACCCCCA TTTGCGTTAT ATAAACCTGT CAAGTAACCG
     AGTCGGGTCT CGGAAACGGT TCTTGGGGGT AAACGCAATA TATTTGGACA GTTCATTGGC 164  L   T   T   L   S   W   Q   L   F   Q   T   L   S   L   R   E   L   Q   L   E
1621 GCTCACCACA CTCTCGTGGC AGCTCTTCCA GACGCTGAGT CTTCGGGAAT TGCAGTTGGA
```

*FIG._14B*

```
                  CGAGTGGTGT GAGAGCACCG TCGAGAAGGT CTGCGACTCA GAAGCCCTTA ACGTCAACCT

184          Q  N  F    F  N  C  S    C  D  I    R  W  M    Q  L  W  Q    E  Q  G
      1681        GCAGAACTTT TTCAACTGCA GCTGTGACAT CCGCTGGATG CAGCTCTGGC AGGAGCAGGG
                  CGTCTTGAAA AAGTTGACGT CGACACTGTA GGCGACCTAC GTCGAGACCG TCCTCGTCCC

204          E  A  K    L  N  S  Q    N  L  Y    C  I  N    A  D  G  S    Q  L  P
      1741        GGAGGCCAAG CTCAACAGCC AGAACCTCTA CTGCATCAAT GCTGATGGCT CCCAGCTTCC
                  CCTCCGGTTC GAGTTGTCGG TCTTGGAGAT GACGTAGTTA CGACTACCGA GGGTCGAAGG

224          L  F  R    M  N  I  S    Q  C  D    L  P  E    I  S  V  S    H  V  N
      1801        TCTCTTCCGC ATGAACATCA GTCAGTGTGA CCTTCCTGAG ATCAGCGTGA GCCACGTCAA
                  AGAGAAGGCG TACTTGTAGT CAGTCACACT GGAAGGACTC TAGTCGCACT CGGTGCAGTT

244          L  T  V    R  E  G  D    N  A  V    I  T  C    N  G  S  G    S  P  L
      1861        CCTGACCGTA CGAGAGGGTG ACAATGCTGT TATCACTTGC AATGGCTCTG GATCACCCCT
                  GGACTGGCAT GCTCTCCCAC TGTTACGACA ATAGTGAACG TTACCGAGAC CTAGTGGGGA

264          P  D  V    D  W  I  V    T  G  L    Q  S  I    N  T  H  Q    T  N  L
      1921        TCCTGATGTG GACTGGATAG TCACTGGGCT GCAGTCCATC AACACTCACC AGACCAATCT
                  AGGACTACAC CTGACCTATC AGTGACCCGA CGTCAGGTAG TTGTGAGTGG TCTGGTTAGA

284          N  W  T    N  V  H  A    I  N  L    T  L  V    N  V  T  S    E  D  N
      1981        GAACTGGACC AATGTTCATG CCATCAACTT GACGCTGGTG AATGTGACGA GTGAGGACAA
                  CTTGACCTGG TTACAAGTAC GGTAGTTGAA CTGCGACCAC TTACACTGCT CACTCCTGTT

304          G  F  T    L  T  C  I    A  E  N    V  V  G    M  S  N  A    S  V  A
      2041        TGGCTTCACC CTGACGTGCA TTGCAGAGAA CGTGGTGGGC ATGAGCAATG CCAGTGTTGC
                  ACCGAAGTGG GACTGCACGT AACGTCTCTT GCACCACCCG TACTCGTTAC GGTCACAACG
```

FIG._14C

| | | L T V | Y Y P P | R V V | S L E | E P E L | R L E |
|---|---|---|---|---|---|---|---|
| 324 | | CCTCACTGTC | TACTATCCCC | CACGTGTGGT | GAGCCTGGAG | GAGCCTGAGC | TGCGCCTGGA |
| 2101 | | GGAGTGACAG | ATGATAGGGG | GTGCACACCA | CTCGGACCTC | CTCGGACTCG | ACGCGGACCT |

| | | H C I | E F V V | R G N | P P P | T L H W | L H N |
|---|---|---|---|---|---|---|---|
| 344 | | GCACTGCATC | GAGTTTGTGG | TGCGTGGCAA | CCCCCCACCA | ACGCTGCACT | GGCTGCACAA |
| 2161 | | CGTGACGTAG | CTCAAACACC | ACGCACCGTT | GGGGGTGGT | TGCGACGTGA | CCGACGTGTT |

| | | G Q P | L R E S | K I I | H V E | Y Y Q E | G E I |
|---|---|---|---|---|---|---|---|
| 364 | | TGGGCAGCCT | CTGCGGGAGT | CCAAGATCAT | CCATGTGGAA | TACTACCAAG | AGGGAGAGAT |
| 2221 | | ACCCGTCGGA | GACGCCCTCA | GGTTCTAGTA | GGTACACCTT | ATGATGGTTC | TCCCTCTCTA |

| | | S E G | C L L F | N K P | T H Y | N N G N | Y T L |
|---|---|---|---|---|---|---|---|
| 384 | | TTCCGAGGGC | TGCCTGCTCT | TCAACAAGCC | CACCCACTAC | AACAATGGCA | ACTATACCCT |
| 2281 | | AAGGCTCCCG | ACGGACGAGA | AGTTGTTCGG | GTGGGTGATG | TTGTTACCGT | TGATATGGGA |

| | | I A K | N P L G | T A N | Q T I | N G H F | L K E |
|---|---|---|---|---|---|---|---|
| 404 | | CATTGCCAAA | AACCCACTGG | GCACAGCCAA | CCAGACCATC | AATGGCCACT | TCCTCAAGGA |
| 2341 | | GTAACGGTTT | TTGGGTGACC | CGTGTCGGTT | GGTCTGGTAG | TTACCGGTGA | AGGAGTTCCT |

^begin ecd insert                                    ^end ecd insert

| | | P F P | E S T D | N F I | L F D | E V S P | T P P |
|---|---|---|---|---|---|---|---|
| 424 | | GCCCTTTCCA | GAGAGCACGG | ATAACTTTAT | CTTGTTTGAC | GAAGTGAGTC | CCACACCTCC |
| 2401 | | CGGGAAAGGT | CTCTCGTGCC | TATTGAAATA | GAACAAACTG | CTTCACTCAG | GGTGTGGAGG |

^begin TM

| | | I T V | T H K P | E E D | T F G | V S I A | V G L |
|---|---|---|---|---|---|---|---|
| 444 | | TATCACTGTG | ACCCACAAAC | CAGAAGAAGA | CACTTTTGGG | GTATCCATAG | CAGTTGGACT |

*FIG._14D*

```
                ATAGTGACAC TGGGTGTTTG GTCTTCTTCT GTGAAAACCC CATAGGTATC GTCAACCTGA
                                                                     ^end TM
          A   A   F   A   C   V   L   L   V   V   L   F   V   M   I   N   K   Y   G   R
464
2521      TGCTGCTTTT GCCTGTGTCC TGTTGGTGGT TCTCTTCGTC ATGATCAACA AATATGGTCG
          ACGACGAAAA CGGACACAGG ACAACCACCA AGAGAAGCAG TACTAGTTGT TTATACCAGC R   S   K   F   G   M   K   G   P   V   A   V   I   S   G   E   E   D   S   A
484
2581      ACGGTCCAAA TTTGGAATGA AGGGTCCCGT GGCTGTCATC AGTGGTGAGG AGGACTCAGC
          TGCCAGGTTT AAACCTTACT TCCCAGGGCA CCGACAGTAG TCACCACTCC TCCTGAGTCG S   P   L   H   H   I   N   H   G   I   T   T   P   S   S   L   D   A   G   P
504
2641      CAGCCCACTG CACCACATCA ACCACGGCAT CACCACGCCC TCGTCACTGG ATGCCGGGCC
          GTCGGGTGAC GTGGTGTAGT TGGTGCCGTA GTGGTGCGGG AGCAGTGACC TACGGCCCGG D   T   V   V   I   G   M   T   R   I   P   V   I   E   N   P   Q   Y   F   R
524
2701      CGACACTGTG GTCATTGGCA TGACTCGCAT CCCTGTCATT GAGAACCCCC AGTACTTCCG
          GCTGTGACAC CAGTAACCGT ACTGAGCGTA GGGACAGTAA CTCTTGGGGG TCATGAAGGC Q   G   H   N   C   H   K   P   D   T   Y   V   Q   H   I   K   R   D   I
544
2761      TCAGGGACAC AACTGCCACA AGCCGGACAC GTATGTGCAG CACATTAAGA GGAGAGACAT
          AGTCCCTGTG TTGACGGTGT TCGGCCTGTG CATACACGTC GTGTAATTCT CCTCTCTGTA
                    ^begin TK
          V   L   K   R   E   L   G   E   G   A   F   G   K   V   F   L   A   E   C   Y
564
2821      CGTGCTGAAG CGAGAACTGG GTGAGGGAGC CTTTGGAAAG GTCTTCCTGG CCGAGTGCTA
          GCACGACTTC GCTCTTGACC CACTCCCTCG GAAACCTTTC CAGAAGGACC GGCTCACGAT
```

FIG._14E

```
584  N   L   S       P   T   K   D       K   M   L       V   A   V       K   A   L   K       D   P   T
2881 CAACCTCAGC CCGACCAAGG ACAAGATGCT TGTGGCTGTG AAGGCCCTGA AGGATCCCAC
     GTTGGAGTCG GGCTGGTTCC TGTTCTACGA ACACCGACAC TTCCGGGACT TCCTAGGGTG

604  L   A   A       R   K   D   F       Q   R   E       A   E   L       L   T   N   L       Q   H   E
2941 CCTGGCTGCC CGGAAGGATT TCCAGAGGGA GGCCGAGCTG CTCACCAACC TGCAGCATGA
     GGACCGACGG GCCTTCCTAA AGGTCTCCCT CCGGCTCGAC GAGTGGTTGG ACGTCGTACT

624  H   I   V       K   F   Y   G       V   C   G       D   G   D       P   L   I   M       V   F   E
3001 GCACATTGTC AAGTTCTATG GAGTGTGCGG CGATGGGGAC CCCCTCATCA TGGTCTTTGA
     CGTGTAACAG TTCAAGATAC CTCACACGCC GCTACCCCTG GGGGAGTAGT ACCAGAAACT

644  Y   M   K       H   G   D   L       N   K   F       L   R   A       H   G   P   D       A   M   I
3061 ATACATGAAG CATGGAGACC TGAATAAGTT CCTCAGGGCC CATGGGCCAG ATGCAATGAT
     TATGTACTTC GTACCTCTGG ACTTATTCAA GGAGTCCCGG GTACCCGGTC TACGTTACTA

664  L   V   D       G   Q   P   R       Q   A   K       G   E   L       G   L   S   Q       M   L   H
3121 CCTTGTGGAT GGACAGCCAC GCCAGGCCAA GGGTGAGCTG GGGCTCTCCC AAATGCTCCA
     GGAACACCTA CCTGTCGGTG CGGTCCGGTT CCCACTCGAC CCCGAGAGGG TTTACGAGGT

684  I   A   S       Q   I   A   S       G   M   V       Y   L   A       S   Q   H   F       V   H   R
3181 CATTGCCAGT CAGATCGCCT CGGGTATGGT GTACCTGGCC TCCCAGCACT TTGTGCACCG
     GTAACGGTCA GTCTAGCGGA GCCCATACCA CATGGACCGG AGGGTCGTGA AACACGTGGC

704  D   L   A       T   R   N   C       L   V   G       A   N   L       L   V   K   I       G   D   F
3241 AGACCTGGCC ACCAGGAACT GCCTGGTTGG AGCGAATCTG CTAGTGAAGA TTGGGGACTT
     TCTGGACCGG TGGTCCTTGA CGGACCAACC TCGCTTAGAC GATCACTTCT AACCCCTGAA

^TK insert site
724  G   M   S       R   D   V   Y       S   T   D       Y   Y   R       V   G   G   H       T   M   L
```

FIG._14F

```
3301  CGGCATGTCC AGAGATGTCT ACAGCACGGA TTATTACAGG GTGGGAGGAC ACACCATGCT
      GCCGTACAGG TCTCTACAGA TGTCGTGCCT AATAATGTCC CACCCTCCTG TGTGGTACGA

744    P   I   R   W   M   M   P   P   E   S   I   M   Y   R   K   F   T   T   E   S   D
3361  CCCCATTCGC TGGATGCCTC CTGAAAGCAT CATGTACCGG AAGTTCACTA CAGAGAGTGA
      GGGGTAAGCG ACCTACGGAG GACTTTCGTA GTACATGGCC TTCAAGTGAT GTCTCTCACT

764    V   W   S   F   G   V   I   L   W   E   I   F   T   Y   G   K   Q   P   W   F
3421  TGTATGGAGC TTCGGGGTGA TCCTCTGGGA GATCTTCACC TATGGAAAGC AGCCATGGTT
      ACATACCTCG AAGCCCCACT AGGAGACCCT CTAGAAGTGG ATACCTTTCG TCGGTACCAA

784    Q   L   S   N   T   E   V   I   E   C   I   T   Q   G   R   V   L   E   R   P
3481  CCAACTCTCA AACACGGAGG TCATTGAGTG CATTACCCAA GGTCGTGTTT TGGAGCGGCC
      GGTTGAGAGT TTGTGCCTCC AGTAACTCAC GTAATGGGTT CCAGCACAAA ACCTCGCCGG

804    R   V   C   P   K   E   V   Y   D   V   M   L   G   C   W   Q   R   E   P   Q
3541  CCGAGTCTGC CCCAAAGAGG TGTACGATGT CATGCTGGGG TGCTGGCAGA GGGAACCACA
      GGCTCAGACG GGGTTTCTCC ACATGCTACA GTACGACCCC ACGACCGTCT CCCTTGGTGT

824    Q   R   L   N   I   K   E   I   Y   K   I   L   H   A   L   G   K   A   T   P
3601  GCAGCGGTTG AACATCAAGG AGATCTACAA AATCCTCCAT GCTTTGGGGA AGGCCACCCC
      CGTCGCCAAC TTGTAGTTCC TCTAGATGTT TTAGGAGGTA CGAAACCCCT TCCGGTGGGG

^stop
                                    R1 site removed with cut and fill^

844    I   Y   L   D   I   L   G   O
3661  AATCTACCTG GACATTCTTG GCTAGTGGTG GCTGGTGGTC ATGAATTAAT TCAATCGATG
      TTAGATGGAC CTGTAAGAAC CGATCACCAC CGACCACCAG TACTTAATTA AGTTAGCTAC

^sv40 early poly A
3721  GCCGCCATGG CCCAACTTGT TTATTGCAGC TTATAATGGT TACAAATAAA GCAATAGCAT
      CGGCGGTACC GGGTTGAACA AATAACGTCG AATATTACCA ATGTTTATTT CGTTATCGTA
```

FIG._14G

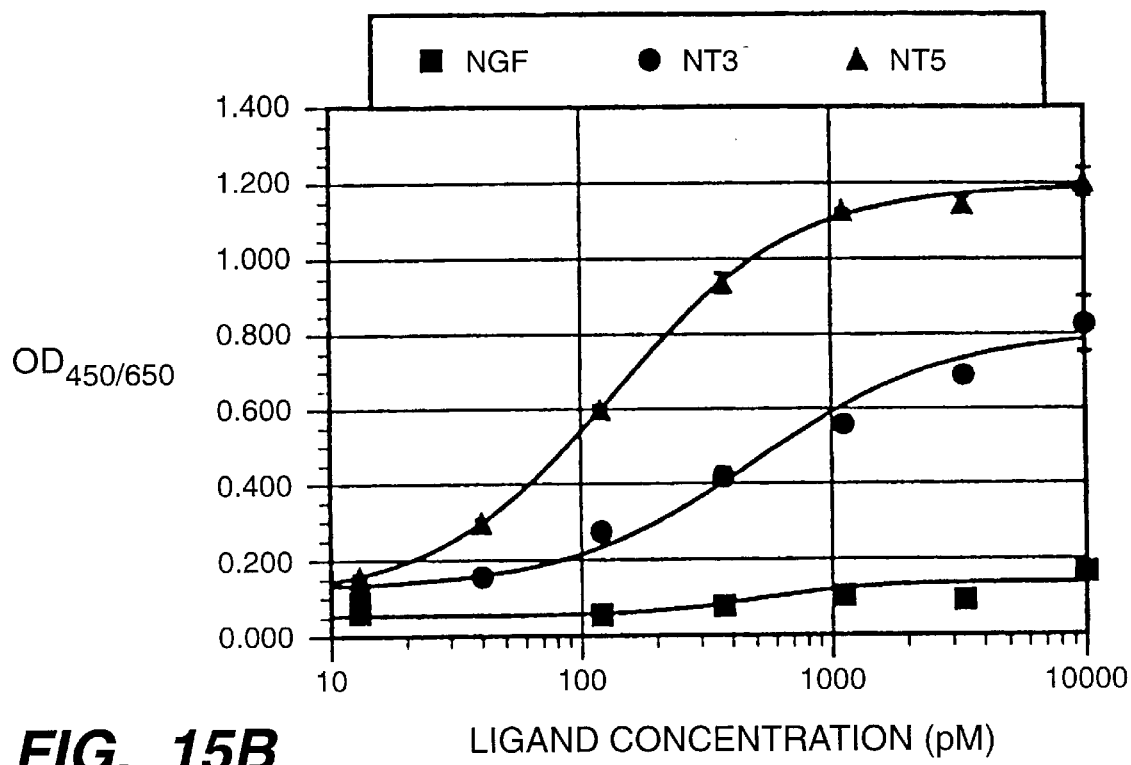
FIG._15B
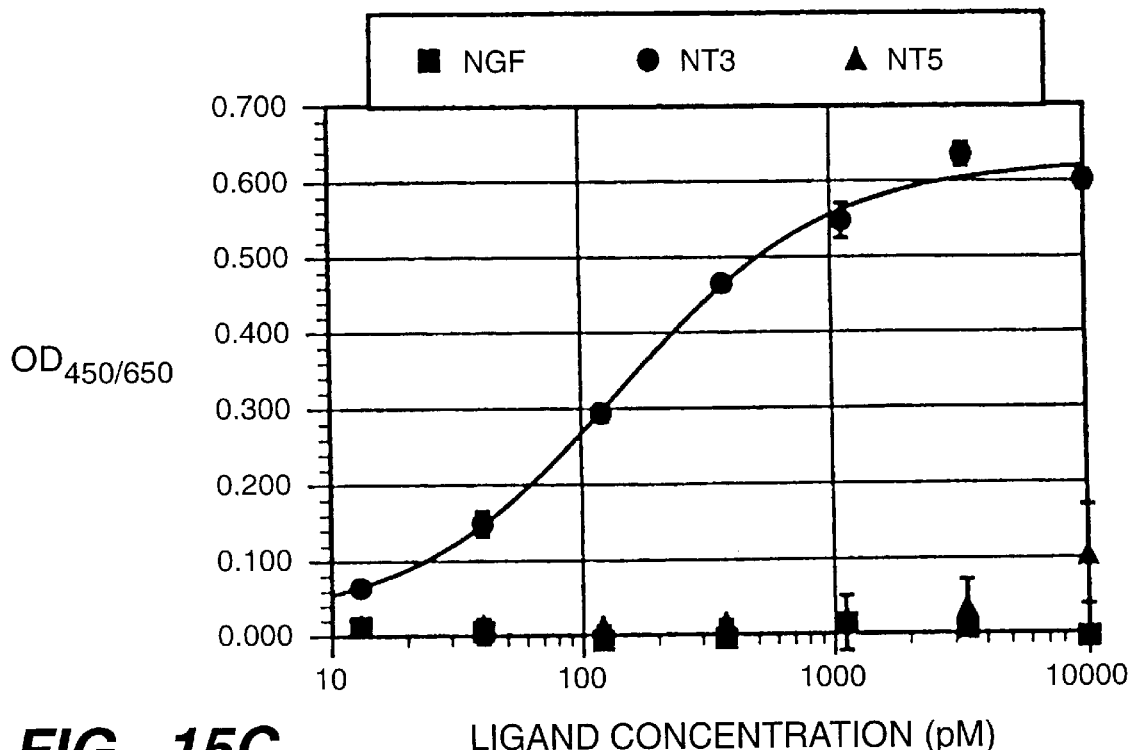
FIG._15C

FIG._16A

```
    aluI
    sstI
    sacI
    hgiJII
    hgiAI/aspHI
    ecl136II
    bsp1286
    bsiHKAI
    bmyI                                                        aluI
    banII                                    sau3AI pvuII
    taqI              nlaIV                  mboI/ndeII[dam-]
                      scrFI                   dpnI[dam+]
                      mvaI                    pvuI/bspCI
                      ecoRII                  pleI dpnII[dam-]
                      dsaV                    hinfI  taqI[dam-]
                      bstNI             rmaI    mcrI    nspBII
                      apyI[dcm+]        maeI    taqI[dam-]
                      bsaJI
  1 TTCGAGCTCG CCCGACATTG ATTATTGACT AGAGTCGATC GACAGCTGTG GAATGTGTGT CAGTTAGGGT
    AAGCTCGAGC GGGCTGTAAC TAATAACTGA TCTCAGCTAG CTGTCGACAC CTTACACACA GTCAATCCCA sfaNI              scrFI
                                                       ppu10I             mvaI
                                                       nsiI/avaIII        ecoRII
                                                       nlaIII             dsaV
                                                       sphI               bstNI
                                                       nspI               apyI
                                                       nspHI              sexAI
 71 GTGGAAAGTC CCCAGGCTCC CCAGCAGGCA GAAGTATGCA AAGCATGCAT CTCAATTAGT CAGCAACCAG
    CACCTTTCAG GGGTCCGAGG GGTCGTCCGT CTTCATACGT TTCGTACGTA GAGTTAATCA GTCGTTGGTC
```

FIG._16B

```
                                                                          nlaIII
                                                                          styI
                                                          sphI            ncoI
                                                          nspI            bslI dsaI
        nlaIV                             nsiI/avaIII     nspHI           aciI bsaJI
     scrFI          sfaNI                 nlaIII
     mvaI                    ppu10I
     ecoRII
     dsaV
         bstNI
         apyI[dcm+]
[dcm+]   bsaJI
141 GTGTGGAAAG TCCCCAGGCT CCCCAGCAGG CAGAAGTATG CAAAGCATGC ATCTCAATTA GTCAGCAACC
    CACACCTTTC AGGGGTCCGA GGGGTCGTCC GTCTTCATAC GTTTCGTACG TAGAGTTAAT CAGTCGTTGG aciI bsrI aciI
               aciI      aciI fokI       CGCCCAGTTC CGCCCATTCT CCGCCCCATG
    aciI       CCCCTAACTC GCCCATCCCG     GCGGGTCAAG GCGGGTAAGA GGCGGGGTAC
211 ATAGTCCCGC CCCCTAACTC GCCCATCCCG CCCCTAACTC CGCCCAGTTC CGCCCATTCT CCGCCCCATG
    TATCAGGGCG GGGGATTGAGG CGGGTAGGGC fnu4HI
                 bglI
                 sfiI
                 haeIII/palI
            mnlI  mnlI       ddeI                                          mnlI
       haeIII/palI bsaJI mnlI aluI
       mnlI bsaJI aciI    haeIII/palI
281 GCTGACTAAT TTTTTTTATT TATGCAGAGG CCGAGGCCGC CTCGGCCCTCT GAGCTATTCC AGAAGTAGTG
    CGACTGATTA AAAAAAATAA ATACGTCTCC GGCTCCGGCG GAGCCGGAGA CTCGATAAGG TCTTCATCAC
```

```
                      rmaI
                      styI
                      bsaJI
                      blnI
                      avrII                                                    haeIII/palI
                      haeIII/palI                                              mcrI
                      stuI                              aluI                   eagI/xmaIII/eclXI
            mnlI      haeI                              rmaI                   eaeI
            mnlI mael                                   maeI                   cfrI
      mnlI                                              nheI                   mspI
                                                        aluI                   hpaII
351 AGGAGGCTTT TTTGGAGGCC TAGGCTTTTG CAAAAAGCTA GCTTATCCGG
    TCCTCCGAAA AAACCTCCGG ATCCGAAACT GTTTTTCGAT CGAATAGGCC scrFI
    nciI                     tfiI
    mspI                     hinFI
    hpaII      aciI                                                                       aciI
    dsaV       thaI                                                maeIII     rsaI
    cauII      fnuDII/mvnI                                         maeIII     csp6I  scfI
               bstUI
               bsh1236I
401 CCGGGAACGG TGCATTGGAA CGCGGATTCC CCGTGCCAAG AGTGACGTAA GTACCGCCTA TAGAGGGATA
    GGCCCTTGCC ACGTAACCTT GCGCCTAAGG GGCACGGTTC TCACTGCATT CATGGCGGAT ATCTCGCTAT
                                                           ^splice donor fnu4HI
            bbvI                                                                    pflMI
            nspBII                                                                  bslI
    mnlI    aciI        nlaIII   taqI                     sfaNI
471 AGAGGATTTT ATCCCCGCTG CCATCATGGT TCGACCATTG AACTGCATCG TCGCCCGTGTC CCAAAATATG
    TCTCCTAAAA TAGGGGCGAC GGTAGTACCA AGCTGGTAAC TTGACGTAGC AGCGGGCACAG GGTTTTATAC
                 DHFR ATG^

```
                                        haeIII/palI
                                        haeI
                                        scrFI
                                        mvaI          bsrBI
                                        ecoRII
                                        dsaV                              rsaI
                                        bstNI    aciI                     csp6I
                              bsmAI     apyI[dcm+]           xmnI         scaI
                              bsaI      bsaJI  mnlI  ddeI    asp700    GGAACGAGTT CAAGTACTTC CAAAGAATGA
541 GGGATTGGCA AGAACGGAGA CCTACCCTGG CCTCCGCTCA                        CCTTGCTCAA GTTCATGAAG GTTTCTTACT
    CCCTAACCGT TCTTGCCTCT GGATGGGACC GGAGGCGAGT scrFI
                                                                                         mvaI
                                                                                         ecoRII
                                                                                         dsaV
            eco57I                                                                       bstNI
            mboII                           tfiI                                         apyI[dcm+]
            earI/ksp632I                    hinfI                                        sexAI         ddeI
            mnlI                  alwNI           hphI
611 CCACAACCTC TTCAGTGGAA GGTAAACAGA ATCTGGTGAT TATGGGTAGG AAAACCTGGT TCTCCATTCC
    GGTGTTGGAG AAGTCACCTT CCATTTGTCT TAGACCACTA ATACCCATCC TTTTGGACCA AGAGGTAAGG tfiI    tru9I       tru9I
        hinfI   mseI        mseI     ddeI
        mboII taqI  ahaIII/draI   aseI/asnI/vspI                                bslI     mnlI
681 TGAGAAGAAT CGACCTTTAA AGGACAGAAT TAATATAGTT CTCAGTAGAG AACTCAAAGA ACCACCACGA
    ACTCTTCTTA GCTGGAAATT TCCTGTCTTA ATTATATCAA GAGTCATCTC TTGAGTTTCT TGGTGGTGCT
```

FIG._16E

```
sstI
sacI
hgiJII
hgiAI/aspHI
ecl136II
bsp1286
bsiHKAI
  bmyI                                           tru9I              mspI
  banII                                          aflII/bfrI         hpaII
    aluI            bstXI    fokI sfaNI mseI                        bsaWI                  haeIII/palI
                                                                                           haeI
751 GGAGCTCATT TTCTTGCCAA AAGTTTGGAT GATGCCTTAA GACTTATTGA ACAACCGGAA TTGGCAAGTA
    CCTCGAGTAA AAGAACGGTT TTCAAACCTA CTACGGAATT CTGAATAACT TGTTGGCCTT AACCGTTCAT scrFI                scrFI
                                          mvaI                 mvaI
                                          ecoRII               ecoRII
                                          dsaV      tfiI       dsaV
                                          bstNI     nlaIII     bstNI       ddeI
    accI nlaIII       mnlI                apyI[dcm+] hinfI     apyI[dcm+]
821 AAGTAGACAT GGTTTGGATA GTCGGAGGCA GTTCTGTTTA CCAGGAAGCC ATGAATCAAC CAGGCCACCT
    TTCATCTGTA CCAAACCTAT CAGCCTCCGT CAAGACAAAT GGTCCTTCGG TACTTAGTTG GTCCGGTGGA
```

FIG._16F

```
                                                                                    maeII
                         nlaIII                                           aflIII
                         sau3AI                                  maeII
                         mboI/ndeII[dam-]
                         dpnI[dam+]
                         dpnII[dam-]       apoI
     pleI
     hinfI    maeIII alwI[dam-]        maeIII
891  TAGACTCTTT GTGACAAGGA TCATGCAAGGA ATTGAAAGT GACACGTTTT TCCCAGAAAAT TGATTTGGGG
     ATCTGAGAAA CACTGTTCCT AGTACGTCCT TAAACTTTCA CTGTGCAAAA AGGGTCTTTA ACTAAACCCC
                                  hgaI
                                  hinlI/acyI
                                  ahaII/bsaHI
                                  scrFI               mnlI
                                  mval
                                  ecoRII
                                  dsaV
                                  bstNI      ecoNI
                                  apyI[dcm+]          mnlI
          mnlI                    bsaJI     bslI ddeI
961  AAATATAAAC CTCTCCCAGA ATACCCAGGC GTCCTCTCTG
     TTTATATTTG GAGAGGGTCT TATGGGTCCG CAGGAGAGAC
```

FIG._16G

```
     scrFI
     mvaI
     ecoRII
     dsaV
     bstNI
     apyI[dcm+]
     sau96I
     avaII                                                                                    sfaNI
     asuI   mnlI          sfaNI                   accI    mboII                               mboII
1001 AGGTCCAGGA GGAAAAAGGC ATCAAGTATA AGTTTGAAGT CTACGAGAAG AAAGACTAAC AGGAAGATGC
     TCCAGGTCCT CCTTTTTCCG TAGTTCATAT TCAAACTTCA GATGCTCTTC TTTCTGATTG TCCTTCTACG
                                                                      ^END DHFR nlaIII
                                                          styI
                                                          ncoI
                                              ppuI0I      dsaI
                                    alul      nsiI/avaIII  bsaJI
                            mnlI    TCCTAAAGCT ATGCATTTTT ATAAGACCAT GGGACTTTTG
1071 TTTCAAGTTC TCTGCTCCCC TCCTAAAGCT ATGCATTTTT ATAAGACCAT GGGACTTTTG
     AAAGTTCAAG AGACGAGGGG AGGATTTCGA TACGTAAAAA TATTCTGGTA CCCTGAAAAC
```

FIG._16H

```
                                                                                                     sau96I
                                                                                                     avaII
                                                                                                     asuI
                                                     fnu4HI                                          scrFI
                                                     aciI                                            mvaI
                                                     thaI                                            ecoRII
                           sau3AI                    fnuDII/mvnI  tru9I                              dsaV
                           mboI/ndeII[dam-]          bstUI        mseI                               bstNI
                           dpnI[dam+]                bsh1236I     aseI/asnI/vspI                     apyI[dcm+]
              styI         dpnII[dam-]                                                          bslI bsaJI
              bsaJI        alwI[dam-]
                           bstYI/xhoII
1131 CTGGCTTTAG ATCCCCCTGG CTTCGTTAGA ACGCGGCTAC AATTAATACA TAACCTTATG TATCATACAC CTCCCAGGTC
     GACCGAAATC TAGGGGAACC GAAGCAATCT TGCGCCGATG TTAATTATGT ATTGGAATAC ATAGTATGTG GAGGGTCCAG maeIII
           hphI   scfI       fokI
1201 ATACGATTTA GGTGACACTA TAGATAACAT CCACTTTGCC TTTCTCTCCA CAGGTGTCCA CTCCCAGGTC
     TATGCTAAAT CCACTGTGAT ATCTATTGTA GGTGAAACGG AAAGAGAGGT GTCCACAGGT GAGGGTCCAG
```

FIG._16I

```
                                                                    scrFI
                                                                    ncil
                                                                    mspI
                                                                    hpaII
                                                                    dsaV
                                                                    xmaI/pspAI
                                                                    smaI
                                                                    scrFI
                                                                    ncil
                                                                    dsaV
                                                                    cauII
                                                                    bsaJI
                                                                    avaI
                                                            sau3AI
                                                            mboI/ndeII[dam-]
                                                            dpnI[dam+]
                                                            dpnII[dam-]
                                                    nlaIV cauII
                                            pleI    bstYI/xhoII
                                            hinfI   bamHI bsaJI
                                    taqI rmaI mael  alwI[dam-]
                                    salI mael alwI[dam-]
                            scfI    accI xbaI mnlI bsaJI
              scfI  hindIII bspMI  hincII/hindII alwI[dam-]
              aluI pstI
        ddeI  bsgI
  mnlI bsaJI
1271 CAACTGCACC TCGGTTCTAA GCTTCTGCAG GCTTCTGCAG CTTCTGCAG GTCGACTCTA GAGGATCCCC CTCCTAGGGG
     GTTGACGTGG AGCCAAGATT CGAAGACGTC CAGCTGAGAT
```

FIG._16J

```
                                               sau96I
                                       aciI   haeIII/palI
                                       fnu4HI  asuI
                                       bglI    nlaIII
                                       sfiI    styI
                                       eaeI    ncoI                                              aluI
                                       cfrI    dsaI                                              fnu4HI
              ecoRI   taqI  haeIII/palI                                                          bbvI            maeIII
              apoI    claI/bsp106 bsaJI                          AACTTGTTTA TTGCAGCTTA TAATGGTTAC AAATAAAGCA
     1321 GGGGAATTCA ATCGATGGCC GCCATGGCCC                       TTGAACAAAT AACGTCGAAT ATTACCAATG TTTATTTCGT
          CCCCTTAAGT TAGCTACCGG CGGTACCGGG                       ^sv40
                                                                                        rmaI
              sfaNI   apoI                                                              bsmI maeI
     1391 ATAGCATCAC AAATTTCACA AATAAAGCAT TTTTTTCACT GCATTCTAGT TGTGGTTTGT CCAAACTCAT
          TATCGTAGTG TTTAAAGTGT TTATTTCGTA AAAAAAGTGA CGTAAGATCA ACACCAAACA GGTTTGAGTA
```

FIG._16K

```
                                              sau3AI
                                              mboI/ndeII[dam-]
                                              dpnI[dam+]
                                              dpnII[dam-]
                                              pvuI/bspCI
                                              mcrI
                                              taqI[dam-]   tru9I
                                              claI/bsp106[dam-]
                                              sau3AI          mseI
                                              mboI/ndeII[dam-]
                                              dpnI[dam+] xmnI
                                              dpnII[dam-]  aseI/asnI/vspI
                              nlaIII   alwI[dam-]  asp700
1461 CAATGTATCT TATCATGTCT GGATCGATCG GGAATTAATT
     GTTACATAGA ATAGTACAGA CCTAGCTAGC CCTTAATTAA
                                              sv40 origin^ rsaI
                                                                    csp6I
                                                                    nlaIV
                                                                    kpnI
                                                                    hgiCI
                    haeIII/palI                                     banI
                    haeI                                            asp718
            styI                                                    acc65I  ddeI   aciI
            ncoI                              mnlI                           mnlI
      fnu4HI dsaI
      bbvI  bsaJI
      hinPI     nlaIII                mnlI
      hhaI/cfoI nlaIII
1501 CGGGCGCAGCA CCATGGCCTG AAATAACCTC TGAAAGAGGA GTACCTTCTG AGGCGGAAAG
     GCCGCGTCGT GGTACCGGAC TTTATTGGAG ACTTTCTCCT CATGGAAGAC TCCGCCTTTC
```

FIG._16L

```
                                                                           nlaIV
                                                                           scrFI
                                                                           mvaI
                                                                           ecoRII
                                                                           dsaV
                                                                           bstNI
                                                                           apyI[dcm+]
         aluI                                                              bsaJI
         pvuII
         nspBII
1571 AACCAGCTGT GGAATGTGTG TCAGTTAGGG TGTGGAAAGT CCCAGGCTC CCCAGCAGGC AGAAGTATGC
     TTGGTCGACA CCTTACACAC AGTCAATCCC ACACCTTTCA GGGTCCGAG GGGTCGTCCG TCTTCATACG scrFI          scrFI                nlaIV
                                          mvaI           mvaI
         sfaNI                            ecoRII         ecoRII
           ppu10I                         dsaV           dsaV
     nsiI/avaIII
       nlaIII                                  bstNI          bstNI
          sphI                                 apyI[dcm+]     apyI[dcm+]
          nspI                                 sexAI          bsaJI
         nspHI
1641 AAAGCATGCA TCTCAATTAG TCAGCAACCA GGTGTGGAAA GTCCCCAGGC TCCCCAGCAG GCAGAAGTAT
     TTTCGTACGT AGAGTTAATC AGTCGTTGGT CCACACCTTT CAGGGGTCCG AGGGGTCGTC CGTCTTCATA sfaNI
           ppu10I
     nsiI/avaIII
       nlaIII
          sphI
          nspI
         nspHI                                                      aciI
                                                   aciI       aciI  fokI
1711 GCAAAGCATG CATCTCAATT AGTCAGCAAC CATAGTCCCG CCCCTAACTC CGCCCATCCC GCCCCTAACT
     CGTTTCGTAC GTAGAGTTAA TCAGTCGTTG GTATCAGGGC GGGGATTGAG GCGGGTAGGG CGGGGATTGA
```

FIG._16M

```
                                                      nlaIII
                                                      styI
                                                      ncoI                                          mnlI
                bsrI                     bslI dsaI
       asiI    aciI        CCGCCCAGTT CCGCCCCATTC TCCGCCCCAT GGCTGACTAA TTTTTTTTAT TTATGCAGAG
1781 CCGCCCAGTT CCGCCCCATTC TCCGCCCCAT GGCTGACTAA TTTTTTTTAT TTATGCAGAG
     GGCGGGTCAA GGCGGGGTAAG AGGCGGGGTA CCGACTGATT AAAAAAAATA AATACGTCTC styI
                                                                                          bsaJI
               fnu4HI                                                                     blnI
               bglI                                                                       avrII
               sfiI                                                                       haeIII/palI
               haeIII/palI                                                     stuI
       mnlI    mnlI      bsaJI mnlI   alul                               mnlI  haeI
       haeIII/palI               ddeI                                          mnlI
       bsaJI aciI        haeIII/palI                                 mnlI
1841 GCCGAGGCCG CCTCGGCCTC TGAGCTATTC CAGAAGTAGT GAGGAGGCTT TTTTGGAGGC
     CGGCTCCGGC GGAGCCGGAG ACTCGATAAG GTCTTCATCA CTCCTCCGAA AAAACCTCCG
```

FIG._16N

```
                                                              hinPI
                                             aciI             hhaI/cfoI
                                             haeIII/palI     thaI
                                      mcrI                   bstUI              bspMI
                                      eagI/xmaIII/eclXI  fnuDII/mvnI            scfI
                              taqI  eaeI                      hinPI             pstI
                              xhoI  notI                      hhaI/cfoI  tru9I  sse83871
                              paeR7I cfrI         tru9I       ascI      ahaIII/draI  bsgI
                              avaI  fnu4HI        pacI        msel  tru9I bshl236I mseI
                        mnlI  aciI      mseI bsrBI fnu4HI     mseI  bssHII    swaI
              rmaI      alul  maeIII  bsrBI fnu4HI  GCGGCCGCTT AATTAAGGCG CGCCATTTAA ATCCTGCAGG
              maeI
1901 CTAGGCTTTT GCAAAAAGCT GTTACCTCGA GCGGCCGCTT AATTAAGGCG CGCCATTTAA ATCCTGCAGG
     GATCCGAAAA CGTTTTTCGA CAATGGAGCT CGCCGGCGAA TTAATTCCGC GCGGTAAATT TAGGACGTCC
                  ^start pUC118
                              ^linearization linker inserted into HpaI site scrFI
                                                             mvaI
                                                             ecoRII
                                                             dsaV
                      haeIII/palI                            bstNI
                      eaeI                                   apyI[dcm+]           tru9I
              maeIII  cfrI                                                         mseI
              alul    bsrI        maeI maeII bsrI            bsaJI maeIII
1971 TAACAGCTTG GCACTGGCCG TCGTTTTACA ACGTCGTGAC CTGGCGTTAC CCAACTTAAT
     ATTGTCGAAC CGTGACCGGC AGCAAAATGT TGCAGCACTG ACCCTTTGG GACCGCAATG GGTTGAATTA
```

FIG. 16O

```
                                                                    sau3AI
                                                          sau96I    mboI/ndeII[dam-]
                                                      haeIII/palI
                                                      asuI    dpnI[dam+]
                                                           mnlI       dpnII[dam-]
                                                        mboII  aciI  pvuI/bspCI
                                                      earI/ksp632I   mcrI
              aluI
              pvuII
              nspBII
     fnu4HI
     bbvI  fokI  CACATCCCCC CTTCGCCAGC TGGCGTAATA GCGAAGAGGC CCGCACCGAT
2041 CGCCTTGCAG                                                GGCGTGGCTA
     GCGGAACGTC GTGTAGGGGG GAAGCGGTCG ACCGCATTAT CGCTTCTCCG hinPI
                                  hhaI/cfoI
                                  nlaIV
                                  narI
                                  kasI
                                  hinlI/acyI
                                  hgiCI
                                  haeII     aciI
                                  banI     sfaNI
                                       ahaII/bsaHI             sfaNI
                    bglI                            GCCTGATGCG GTATTTCTC CTTACGCATC
2101 CGCCCTTCCC AACAGTTGCG TAGCCTGAAT GGGGAATGGC CCGCTTACCG CGGACTACGC CATAAAAGAG GAATGCGTAG
     GCGGGAAGGG TTGTCAACGC ATCGGACTTA
```

FIG._16P

```
                                                      hinPI
                                                      thaI
                                                      fnuDII/mvnI
                                                      bstUI scfI       hinPI
                                                      bsh1236I         hhaI/cfoI
                                          rsaI hhaI/cfoI    fnu4HI
        aciI     aciI   maeII         csp6I    bslI    aciI
2171 TGTGCGGTAT TTCACACCGC ATACGTCAAA GCAACCATAG TACGGCGCCCT GTAGCGGGGC
     ACACGCCATA AAGTGTGGCG TATGCAGTTT CGTTGGTATC ATGCGCGGGA CATCGCCGCG fnu4HI
           thaI                       fnu4HI
           fnuDII/mvnI                hinPI                        hinPI
           bstUI                      hhaI/cfoI                    hhaI/cfoI
           hinPI aciI       thaI
           hhaI/cfoI        fnuDII/mvnI                rmaI
                            bstUI                              hinPI    haeII
     tru9I aciI             bsh1236I    aciI                   hhaI/cfoI bsrBI
     mseI bsh1236I          maeIII bbvI maeIII         haeII maeI  aciI
2231 ATTAAGGCGG GCGGGTGTGG TGGTTACGCG CAGGCGTGACC GCTACACTTG CCAGCGCCCT AGCGCCCGCT
     TAATTCGCGC CGCCCACACC ACCAATGCGC GTCGCACTGG CGATGTGAAC GGTCGCGGGA TCGCGGGCGA nlaIV
                                                                            hgiJII
                                               mspI                         bsp1286
                                               hpaII                        bmyI
                                    mboII      naeI              aluI       banII
                                    maeII cfr10I
2301 CCTTTCGCTT TCTTCCCTTC CTTTCTCGCC ACGTTCGCCG GCTTTCCCCG TCAAGCTCTA AATCGGGGGC
     GGAAAGCGAA AGAAGGGAAG GAAAGAGCGG TGCAAGCGGC CGAAAGGGGC AGTTCGAGAT TTAGCCCCCG
```

FIG._16Q

```
                                                        mnlI
                                        nlaIV
                                        hgiCI
                                        banI taqI                          hphI
              nlaIV    GTTCCGATTT AGTGCTTTAC GGCACCTCGA CCCCAAAAAA CTTGATTTGG
2371 TCCCTTTAGG GTTCCGATTT AGTGCTTTAC GGCACCTCGA CCCCAAAAAA CTTGATTTGG
     AGGGAAATCC CAAGGCTAAA TCACGAAATG CCGTGGAGCT GGGGTTTTTT GAACTAAACC maeII  haeIII/palI                              maeII pleI
              draIII sau96I                                   drdI hinfI maeII
              bsaAI  asuI
2401 GTGATGGTTC ACGTAGTGGG CCATCGCCCT GATAGACGGT TTTTCGCCCT TTGACGTTGG AGTCCACGTT
     CACTACCAAG TGCATCACCC GGTAGCGGGA CTATCTGCCA AAAAGCGGGA AACTGCAACC TCAGGTGCAA tru9I                                 bslI
          mseI   pleI              bsrI         bslI  avaI
          hinfI
2501 CTTTAATAGT GGACTCTTGT TCCAAACTGG AACAACACTC AACCCTATCT CGGGCTATTC TTTTGATTTA
     GAAATTATCA CCTGAGAACA AGGTTTGACC TTGTTGTGAG TTGGGATAGA GCCCGATAAG AAAACTAAAT haeIII/palI            tru9I                     tru9I
                 tru9I mseI                     alul   mseI   apoI        mseI
2571 TAAGGGATTT TGCCGATTTC GGCCTATTGG TTAAAAAATG AGCTGATTTA ACAAAAATTT
     ATTCCCTAAA ACGGCTAAAG CCGGATAACC AATTTTTTAC TCGACTAAAT TGTTTTTAAA
```

FIG._16R

```
                                                          hgiAI/aspHI
                                                          bsp1286
                                                          bsiHKAI
      thaI                                                bmyI    ddeI
      fnuDII/mvnI                  maeII                  apaLI/snoI  rsaI
      apoI                         psp1406I               alw44I/snoI csp6I
      bstUI   tru9I                tru9I
      bsh1236I msel   sspI msel
2631  AACGGAATT TTAACAAAAT ATTAACGTTT ACAATTTTAT GGTGCACTCT CAGTACAATC
      TTGCGCTTAA AATTGTTTTA TAATTGCAAA TGTTAAAATA CCACGTGAGA GTCATGTTAG hinPI
                                                   bsrI         fnu4HI
                                                   maeIII       nlaIII hhaI/cfoI
              fnu4HI  tru9I                        maeII        bsaAI tth111I/aspI bbvI
              sfaNI   aciI    msel         aciI
2691  TGCTCTGATG  CCGCATAGTT AAGCCAACTC CGCTATCGCT ACGTGACTGG GTCATGGCTG CGCCCCGACA
      ACGAGACTAC  GGCGTATCAA TTCGGTTGAG GCGATAGCGA TGCACTGACC CAGTACCGAC GCGGGGCTGT hinPI                            sfaNI
                  hhaI/cfoI                        mspI                       maeIII
                  thaI                             hpaII
                  fnuDII/mvnI                      scrFI
                  bstUI                            nciI
               nspBII bsh1236I                     dsaV fokI               aluI
               acil acil hgaI    drdI              cauII  acil      CCGCTTACAG ACAAGCTGTG
2761  CCCGCCAACA CCCGCTGACG CGCCCTGACG GGCTTGTCTG CTCCCGGCAT CCGCTTACAG ACAAGCTGTG
      GGGCGGTTGT GGGCGACTGC GCGGGACTGC CCGAACAGAC GAGGGCCGTA GGCGAATGTC TGTTCGACAC
```

FIG._16S

```
           scrFI
           nciI
           mspI                                                                                       thaI
           hpaII            nspI                                                                      fnuDII/mvnI
           dsaV             nspHI                                                                     bstUI
       esp3I      fnu4HI                                                                              bsh1236I
       bsmAI         bbvI                                                                             hinPI
       bslI  cauII aluI nlaIII     mnlI              hphI           hphI                              hhaI/cfoI
                                                                                                      thaI mnlI
                                                                                                      fnuDII/mvnI
                                                                                                      bstUI
                                                                                                      bsh1236I
2831 ACCGTCTCCG GGAGCTGCAT GTGTCAGAGG TTTCACCGT CATCACCGAA ACGGCGGAGG CAGTATTCTT
     TGGCAGAGGC CCTCGACGTA CACAGTCTCC AAAAGTGGCA GTAGTGGCTT TGCCGCCTCC GTCATAAGAA mnlI
                  haeIII/palI                               nlaIII
         mboII    sau96I                               tru9I rcaI         aciI
         bpuAI    asuI                                 mseI bspHI         thaI
         bbsI   eco0109I/draII                                            fnuDII/mvnI
                                                                          bstUI
                                                                          bsh1236I
                                                                          hinPI
2901 GAAGACGAAA GGGCCCTCGTG ATACGCCTAT TTTTATAGGT TAATGTCATG               hhaI/cfoI
     CTTCTGCTTT CCCGGAGCAC TATGCGGATA AAAATATCCA ATTACAGTAC hinII/acyI
               ahaII/bsaHI
               aatII
           ddeI maeII
2951 ATAATAATGG TTTCTTAGAC GTCAGGTGGC ACTTTTCGGG GAAATGTGCG
     TATTATTACC AAAGAATCTG CAGTCCACCG TGAAAAGCCC CTTTACACGC
```

FIG._16T

```
                                                                bsmAI
                                                                rcaI
                                                         bsrBI  nlaIII
                                                         aciI   bspHI
       nlaIV
3001  CGGAACCCCT ATTTGTTTAT TTTTCTAAAT ACATTCAAAT ATGTATCCGC TCATGAGACA ATAACCCTGA
      GCCTTGGGGA TAAACAAATA AAAAGATTTA TGTAAGTTTA TACATAGGCG AGTACTCTGT TATTGGGACT mboII
                               sspI      earI/ksp632I
3071  TAAATGCTTC AATAATATTG AAAAAGGAAG AGTATGAGTA TTCAACATTT CCGTGTCGCC CTTATTCCCT
      ATTTACGAAG TTATTATAAC TTTTTCCTTC TCATACTCAT AAGTTGTAAA GGCACAGCGG GAATAAGGGA fnu4HI
        aciI                              hphI                           sfaNI
3141  TTTTTGCGGC ATTTGCCTT  CCTGTTTTG CTCACCCAGA AACGCTGGTG AAAGTAAAAG
      AAAAACGCCG TAAACGGAA  GGACAAAAAC GAGTGGGTCT TTGCGACCAC TTTCATTTTC hgiAI/aspHI
                       bsp1286
                       bsiHKAI                         sau3AI
          sau3AI                                       mboI/ndeII[dam-]
          mboI/ndeII[dam+]                             dpnI[dam+]
          dpnI[dam+]  bmyI                             dpnII[dam-]
          dpnII[dam-] apaLI/snoI              taqI     bstYI/xhoII
          mboII[dam-] alw44I/snoI   maeIII    bsrI     alwI[dam-]   aciI
          eco57I                                                    nspBII
3201  ATGCTGAAGA TCAGTTGGGT GCACGAGTGG GTTACATCGA ACTGGATCTC AACAGCGGTA
      TACGACTTCT AGTCAACCCA CGTGCTCACC CAATGTAGCT TGACCTAGAG TTGTCGCCAT
```

FIG._16U

```
       sau3AI
       mboI/ndeII[dam-]
       dpnI[dam+]                maeII
       dpnII[dam-]               psp1406I            hgiAI/aspHI
       alwI[dam-]                 xmnI               bsp1286I   tru9I
       bstYI/xhoII                 asp700             bsiHKAI    mseI
                       mboII                          bmyI      ahaIII/draI
3261 AGATCCTTGA GAGTTTTCGC CCCGAAGAAC GTTTTCCAAT GATGAGCACT TTTAAAGTTC
     TCTAGGAACT CTCAAAAGCG GGGCTTCTTG CAAAAGGTTA CTACTCGTGA AAATTTCAAG scrFI
                                     nciI
                        aciI         mspI
                        thaI         hpaII
                        fnuDII/mvnI  dsaV
                        bstUI
                        bsh1236I   hinlI/acyI
                        hinPI       hgaI cauII                                        aciI
                        hhaI/cfoI    ahaII/bsaHI         bcgI  mcrI     fnu4HI
3321 TGCTATGTGG CGGGTATTA TCCCGTGATG ACGCCGGGCA AGAGCAACTC GGTCGCCGCA
     ACGATACACC GCGCCATAAT AGGGCACTAC TGCGGCCCGT TCTCGTTGAG CCAGCGGCGT rsaI
                       csp6I  bsrI
                       scaI   hphI maeIII  CACAGAAAAG  sfaNI    fokI
         ddeI                      CATCTTACGG
3381 TACACTATTC TCAGAATGAC TTGGTTGAGT ACTCACCAGT CACAGAAAAG CATCTTACGG
     ATGTGATAAG AGTCTTACTG AACCAACTCA TGAGTGGTCA GTGTCTTTTC GTAGAATGCC
```

FIG._16V

```
                                                                haeIII/palI
                                                                eaeI
                                                                cfrI
                                                                fnu4HI
                              fnu4HI                            aciI
                              bbvI         nlaIII      CATGAGTGAT AACACTGCGG CCAACTTACT
       nlaIII      AGTAAGAGAA TTATGCAGTG CTGCCATAAC    GTACTCACTA TTGTGACGCC GGTTGAATGA
3441 ATGGCATGAC    TCATTCTCTT AATACGTCAC GACGGTATTG
     TACCGTACTG
                              sau96I
                              avaII                                    nlaIII
                              asuI                                     sau3AI maeIII
                      sau3AI                                           mboI/ndeII[dam-]
                      mboI/ndeII[dam-]                                 dpnI[dam+]
                      dpnI[dam+]                                       dpnII[dam-]
                      dpnII[dam-]
                      pvuI/bspCI                       nlaIII alwI[dam-]
                mcrI  mnlI           aluI    aciI
3511 TCTGACAACG ATCGGAGGAC CGAAGGAGCT AACCGCTTTT TTGCACAACA TGGGGGATCA TGTAACTCGC
     AGACTGTTGC TAGCCTCCTG GCTTCCTCGA TTGGCGAAAA AACGTGTTGT ACCCCCTAGT ACATTGAGCG
                     mspI
          sau3AI     nlaIV                                                   fnu4HI
          mboI/ndeII[dam-] aluI                              maeIII sfaNI    bbvI
          dpnI[dam+]   hpaII
          dpnII[dam-] bsaWI
3581 CTTGATCGTT GGGAACCGGA GCTGAATGAA GCCATACCAA ACGACGAGCG TGACACCACG ATGCCAGCAG
     GAACTAGCAA CCCTTGGCCT CGACTTACTT CGGTATGGTT TGCTGCTCGC ACTGTGGTGC TACGGTCGTC
```

```
                                                               mspI
                                                               hpaII
                                                               scrFI
                                    hinPI                      nciI
                                    hhaI/cfoI            aluI  dsaV
                                    mstI                 rmaI  cauII
                          avaII/fspI        bsrI         maeI
                   maeII              tru9I
                   psp1406I           mseI
3651 CAATGGCAAC AACGTTGCGC AAACTATTAA CTGGCGAACT ACTTACTCTA GCTTCCCGGC
     GTTACCGTTG TTGCAACGCG TTTGATAATT GACCGCTTGA TGAATGAGAT CGAAGGGCCG bglI
                                                                 sau96I
                                     sau96I                      haeIII/palI
       tru9I       fokI              avaII           hinPI  asuI mspI
       mseI        bsrI       aciI   asuI            hhaI/cfoI   hpaII
       aseI/asnI/vspI  mnlI
3711 AACAATTAAT AGACTGGATG GAGGGGATA AAGTTGCAGG ACCACTTCTG CGCTCGGCCC TTCCGGCTGG
     TTGTTAATTA TCTGACCTAC CTCCGCCTAT TTCAACGTCC TGGTGAAGAC GCGAGCCGGG AAGGCCGACC thaI
                                                          fnuDII/mvnI
                              mspI                        bstUI
                              hpaII                bsmAI aciI          fnu4HI
                              cfr10I               bsaI bsh1236I       bbvI
                       nlaIV hphI
                  gsuI/bpmI
3781 CTGGTTTATT GCTGATAAAT CTGGAGCCGG TGAGCGTGGG TCTCGCGGTA TCATTGCAGC
     GACCAAATAA CGACTATTTA GACCTCGGCC ACTCGCACCC AGAGCGCCAT AGTAACGTCG
```

```
      sau96I
       asuI
       nlaIV                                                              pleI
      bsrI haeIII/palI    mnlI                                            hinfI
                                                               eam1105I
3841 ACTGGGGCCA GATGGTAAGC CCTCCCGTAT CGTAGTTATC TACACGACGG GGAGTCAGGC
     TGACCCCCGT CTACCATTCG GGAGGGCATA GCATCAATAG ATGTGCTGCC CCTCAGTCCG ddeI
                                     sau3AI       nlaIV
                                    mboI/ndeII[dam-]
                                     dpnI[dam+]       hgiCI        tru9I
                                     dpnII[dam-]   banI mnlI       mseI
      fokI
3901 AACTATGGAT GAACGAAATA GACAGATCGC TGAGATAGGT GCCTCACTGA TTAAGCATTG
     TTGATACCTA CTTGCTTTAT CTGTCTAGCG ACTCTATCCA CGGAGTGACT AATTCGTAAC tru9I
                                                         mseI             tru9I
      maeIII                                          ahaIII/draI          mseI
3961 GTAACTGTCA GACCAAGTTT ACTCATATAT ACTTTAGATT GATTAAAAC TTCATTTTA
     CATTGACAGT CTGGTTCAAA TGAGTATATA TGAAATCTAA CTAATTTTG AAGTAAAAAT
             rmaI        sau3AI
      sau3AI hphI   mboI/ndeII[dam-]
     mboI/ndeII[dam-]
      dpnI[dam+]     dpnI[dam+]
      dpnII[dam-]    dpnII[dam-]
      tru9I bstYI/xhoII   alwI[dam-]                                      maeII
      mseI   alwI[dam-]    bstYI/xhoII              nlaIII                tru9I
     ahaIII/draI maeI   mboII[dam-]                  rcaI                  mseI
                                                    bspHI
4021 ATTTAAAAGG ATCTAGGTGA AGATCCTTTT TGATAATCTC ATGACCAAAA TCCCTTAACG TGAGTTTTCG
     TAAATTTTCC TAGATCCACT TCTAGGAAAA ACTATTAGAG TACTGGTTTT AGGAATTGC ACTCAAAAGC
```

FIG._16Y

```
                                                    sau3AI
                                                    mboI/ndeII[dam-]
                                                    dpnI[dam+]          sau3AI
                                                    dpnII[dam-]         mboI/ndeII[dam-]
                                                    bstYI/xhoII         dpnI[dam+]
                                      sau3AI    alwI[dam-]              dpnII[dam-]
                                      mboI/ndeII[dam-]                  alwI[dam-]
                                      dpnI[dam+] mboI[dam-]
                hgaI                  dpnII[dam-]                       bstYI/xhoII
4091  TTCCACTGAG CGTCAGACCC CGTAGAAAAG ATCAAAGGAT CTTCTTGAGA TCCTTTTTTT
      AAGGTGACTC GCAGTCTGGG GCATCTTTTC TAGTTTCCTA GAAGAACTCT AGGAAAAAAA
         ddeI thaI
         fnuDII/mvnI
         bstUI
         bsh1236I                                            aciI
         hinPI        fnu4HI                                 nspBII
         hhaI/cfoI    bbvI                     aciI
4151  CTGCGCGTAA TCTGCTGCTT GCAAACAAAA AAACCACCGC TACCAGCGGT GGTTTGTTTG
      GACGCGCATT AGACGACGAA CGTTTGTTTT TTTGGTGGCG ATGGTCGCCA CCAAACAAAC sau3AI
            mboI/ndeII[dam-]
            dpnI[dam+]
            dpnII[dam-]
            alwI[dam-]                               bsrI             hinPI
      mspI                                           maeIII   eco57I  hhaI/cfoI
      hpaII  aluI
4211  CCGGATCAAG AGTACCAAC TCTTTTTCCG AAGGTAACTG GCTTCAGCAG AGGCGAGATA CCAAATACTG
      GGCCTAGTTC TCGATGGTTG AGAAAAAGGC TTCCATTGAC CGAAGTCGTC TCCGCTCTAT GGTTTATGAC
```

FIG. 16Z-1

```
         rmaI                         haeIII/palI
         maeI       bslI       haeI                       scfI       aciI                        mnlI
4281 TCCTTCTAGT GTAGCCGTAG TTAGGCCACC ACTTCAAGAA CTCTGTAGCA CCGCCTACAT ACCTCGCTCT
     AGGAAGATCA CATCGGCATC AATCCGGTGG TGAAGTTCTT GAGACATCGT GGCGGATGTA TGGAGCGAGA scrFI
                                                                nciI
                              fnu4HI                            mspI
                       alwNI  bbvI                              hpaII         pleI
                  bsrI fnu4HI     bsrI                          dsaV          hinfI
         maeIII   bbvI                                          cauII
4351 GCTAATCCTG TTACCAGTGG CTGCTGCCAG TGGCGATAAG TCGTGTCTTA CCGGGTTGGA CTCAAGACGA
     CGATTAGGAC AATGGTCACC GACGACGGTC ACCGCTATTC AGCACAGAAT GGCCCAACCT GAGTTCTGCT hgiAI/aspHI
                          nspBII                           bsp1286
                          fnu4HI                           bsiHKAI
                mspI      bbvI  mcrI                       bmyI
                hpaII     hinPI aciI                       apaLI/snoI
                bsaWI           hhaI/cfoI                  alw44I/snoI   aluI
         maeIII
4421 TAGTTACCGG ATAAGGGCCA GCGGTCGGGC TGAACGGGGG GTTCGTGCAC ACAGCCCAGC TTGGAGCGAA
     ATCAATGGCC TATTCCCGGT CGCCAGCCCG ACTTGCCCCC CAAGCACGTG TGTCGGGTCG AACCTCGCTT hinPI
                                                                hhaI/cfoI
          ddeI    scfI                                          haeII
4491 CGACCTACAC CGAACTGAGA TACCTACAGC GTGAGCATTG AGAAAGCGCC ACGCTTCCCG AAGGGAGAAA
     GCTGGATGTG GCTTGACTCT ATGGATGTCG CACTCGTAAC TCTTTCGCGG TGCGAAGGGC TTCCCTCTTT
```

FIG._16Z-2

```
                                                                              scrFI
                                                                              mvaI
                                                                              ecoRII    mvaI
                                                                              dsaV      ecoRII
                                                                              bstNI
                                         hinPI mnlI                           bsaJI
               mspI                      hhaI/cfoI  aluI apyI[dcm+]
               hpaII
               bslI    fnu4HI      GCGGCAGGGT  GAGCGCACGA GGGAGCTTCC AGGGGAAAC
        aciI   bsaWI   aciI
4561 GGGGACAGG TATCCGGTAA GCGGCAGGGT CGGAACAGGA GAGCGCACGA GGGAGCTTCC AGGGGAAAC
     CCGCCTGTCC ATAGGCCATT CGCCGTCCCA GCCTTGTCCT CTCGCGTGCT CCCTCGAAGG TCCCCCTTTG scrFI
                                                              mnlI drdI hgaI taqI        sfaNI
        dsaV
        bstNI
        apyI[dcm+]
4631 GCCTGGTATC TTTATAGTCC TGTCGGGTTT CGCCACCTCT GACTTGAGCG TCGATTTTTG TGATGCTCGT
     CGGACCATAG AAATATCAGG ACAGCCCAAA GCGGTGGAGA CTGAACTCGC AGCTAAAAAC ACTACGAGCA haeIII/palI
                                                    fnu4HI
                                                    aciI
                                                    thaI bslI
                                                    fnuDII/mvnI
                                                    bstUI
         nlaIV                                      bsh1236I
         aciI
4701 CAGGGGGGCG GAGCCTATGG AAAAACGCCA GCAACGCGGC
     GTCCCCCCGC CTCGGATACC TTTTTGCGGT CGTTGCGCCG
```

FIG._16Z-3

```
                     haeIII/palI
             scrFI
             mvaI bslI
             ecoRII
             dsaV                                                                    tfiI
             bstNI                          nspI                                     hinfI
             apyI[dcm+]    haeIII/palI     nspHI
         nlaIV haeI        haeI   aflIII          nlaIII
4741 CTTTTTACGG TTCCTGGCCT TTTGCTGGCC ATGTTCTTTC CTGCGTTATC CCCTGATTCT
     GAAAAATGCC AAGGACCGGA AAACGACCGG TACAAGAAAG GACGCAATAG GGGACTAAGA fnu4HI
                                                        bbvI
                                           bsrBI   aciI fnu4HI    mcrI
                        aciI        aluI   aciI
4811 GTGGATAAACC GTATTACCGG CTTTGAGTGA GCTGATACCG CTCGCCGCAG CCGAACGACC
     CACCTATTGG CATAATGGCC GAAACTCACT CGACTATGGC GAGCGGCGTC GGCTTGCTGG hinPI
                                                  haeII
             fnu4HI                               sapI hhaI/cfoI
             bbvI pleI                            mboII                    mnlI
         hinPI hinfI              mnlI aciI earI/ksp632I         aciI
         hhaI/cfoI                                
4871 GAGGCGCAGCG AGTCAGTGAG CGAGGAAGCG GAAGAGCGCC CAATACGCAA ACCGCCTCTC
     CTCGCGTCGC TCAGTCACTC GCTCCTTCGC CTTCTCGCGG GTTATGCGTT TGGCGGAGAG
```

FIG._16Z-4

```
      thaI
      fnuDII/mvnI
      bstUI
      bsh1236I
      hinPI
      hhaI/cfoI
      thaI
      fnuDII/mvnI
      bstUI
      bsh1236I haeIII/palI          tru9I  aluI
      bslI   eaeI  tfiI asel/asnI/vspI       pvuII
      aciI  cfrI  hinfI  mseI  nspBII                                      bsrI      aciI
4931  CCCGGCGTT GGCCGATTCA TTAATCCAGC TGGCACGACA GGTTTCCCGA CTGGAAAGCG
      GGGCCGCAA CCGGCTAAGT AATTAGGTCG ACCGTGCTGT CCAAAGGGCT GACCTTTCGC
                                                                          scrFI
                                                                          mvaI
                                                                          ecoRII
                                                                          dsaV
                                                            nlaIV bstNI
                             tru9I                          hgiCI apyI[dcm+]
                hinPI        mseI       maeIII              banI bsaJI
                hhaI/cfoI aseI/asnI/vspI   mnlI
4991  GGCAGTGAGC GCAACGCAAT TAATGTGAGT TACCTCACTC ATTAGGCACC CCAGGCTTTA CACTTTATGC
      CCGTCACTCG CGTTGCGTTA ATTACACTCA ATGGAGTGAG TAATCCGTGG GGTCCGAAAT GTGAAATACG
```

FIG._16Z-5

```
           mspI             aciI
             hpaII           bsrBI                        aluI            nlaIII
5061  TTCCGGCTCG TATGTTGTGT GGAATTGTGA GCGGATAACA ATTTCACACA GGAAACAGCT ATGACCATGA
      AAGGCCGAGC ATACAACACA CCTTAACACT CGCCTATTGT TAAAGTGTGT CCTTTGTCGA TACTGGTACT
        tru9I
         mseI
          aseI/asnI/vspI
           xmnI
            asp700
5131  TTACGAATTA A
      AATGCTTAAT T >length: 5141
```

KINASE RECEPTOR ACTIVATION ASSAY

CROSS REFERENCES

This application is a continuation of U.S. application Ser. No. 08/286,305 filed 5 Aug. 1994, now U.S. Pat. No. 5,766,863 which application is a continuation-in-part of co-pending U.S. application Ser. No. 08/170,558 filed 20 Dec. 1993, which application is a continuation of U.S. application Ser. No. 08/157,563 filed 23 Nov. 1993 (abandoned), which applications are incorporated herein by reference and to which applications priority is claimed under 35 USC §120.

BACKGROUND OF THE INVENTION

1. Field of the Invention

This invention relates to a kinase receptor activation (KIRA) assay. In particular, the invention relates to an assay for measuring autophosphorylation of the kinase domain of a receptor protein tyrosine kinase (rPTK) using a kinase receptor activation, enzyme-linked immunosorbent assay (KIRA ELISA).

2. Description of Related Art

One mechanism for signal transduction in animals involves protein phosphorylation. Protein phosphorylation involves the action of protein kinase, an enzyme that transfers a phosphate group from a phosphate donor onto an acceptor amino acid in a substrate protein. Protein phosphatases provide a means for reversing the signal when the stimulus is removed.

Protein kinases have multiple substrates, and classification of the protein kinases is based on the acceptor amino acid specificity. The two most well characterized protein kinases are the protein kinases with a protein alcohol group as acceptor called protein serine/threonine kinases and the protein kinases with a protein phenolic group as acceptor called protein tyrosine kinases (Hunter, *Methods in Enzymology* 200:3–9[1991]).

The most well known type of signal-transducing protein kinases are growth factor receptor protein tyrosine kinases (rPTKs). rPTKs usually comprise a large, glycosylated, extracellular ligand binding domain (ECD) and an intracellular domain (ICD) which contains a tyrosine kinase catalytic domain. A single hydrophobic transmembrane (TM) domain connects the ECD and ICD. Examples of rPTKs include the insulin receptor, epidermal growth factor receptor (EGF-R), platelet-derived growth factor receptor (PDGF-R), insulin-like growth factor receptor (IGF-1-R), and the HER2 receptor, to name a few. See, for example, Ullrich and Schlessinger *Cell* 61:203–212 (1990) and Fantl et al., *Annu. Rev. Biochem.* 62:453–481 (1993). rPTKs can phosphorylate exogenous protein substrates and intrinsic tyrosine residues via their catalytic tyrosine kinase domain. The intrinsic tyrosine residues normally reside in the ICD of the rPTK (see FIG. 1 herein). Activation of the intracellular kinase domain of rPTKs appears to be mediated by receptor oligomerization which results from the conformational alteration of the ECD upon ligand binding thereto. See Ullrich and Schlessinger, supra.

Various assays have been developed which measure tyrosine kinase activity. Some of these assays measure the ability of a tyrosine kinase enzyme to phosphorylate a synthetic substrate polypeptide. For example, an assay has been developed which measures growth factor-stimulated tyrosine kinase activity by measuring the ability of the kinase to catalyze the transfer of the y-phosphate of ATP to a suitable acceptor substrate. See Pike, L., *Methods of Enzymology* 146:353–362 (1987) and Hunter, *Journal of Biological Chemistry* 257(9):4843–4848 (1982), for example. In this assay, the use of [y-$^{32}$P]ATP permits the radioactive labeling of the phosphorylated substrate, which is a synthetic tyrosine-containing peptide. Others have described protein kinase assays wherein incorporation of $^{32}$P into a tyrosine kinase receptor, such as the EGF receptor (see Donato et al., *Cell Growth Differ.* 3:259–268 [1992]), insulin receptor (see Kasuga et al., *Journal of Biological Chemistry* 257(17):9891–9884 [1982] and Kasuga et al, *Methods in Enzymology* 109:609–621 [1985]), and liver growth hormone receptor (see Wang et al., *Journal of Biological Chemistry* 267(24):17390–17396 [1992]), is measured.

The discovery of anti-phosphotyrosine antibodies has provided a non-radioactive, alternative means for measuring phosphorylation of tyrosine residues. For example, White and Backer (*Methods in Enzymology* 201:65–67 [1991]) mention polyclonal antibodies which selectively bind to phosphotyrosine and are considered to be useful for studying rPTKs. An anti-phosphotyrosine monoclonal antibody was used in one of the assays referred to in Madden et al. (*Anal Biochem* 199:210–215 [1991]), which measured phosphatase activity toward the insulin receptor. Anti-phosphotyrosine antibodies were also used by Cleaveland et al., in their protein tyrosine kinase ELISA assay. See Cleaveland et al., *Analytical Biochemistry* 190:249–253 (1990). The method of Cleaveland et al. utilizes purified high-activity oncogene tyrosine kinases, v-src and v-fps, and measures the ability of these tyrosine kinases to phosphorylate synthetic polymeric substrates which are coated on an ELISA microtiter plate. The phosphotyrosine produced by src-induced phosphorylation of the polymeric substrate is then quantitated by addition of an anti-phosphotyrosine antibody, the presence of which is detected using a second rabbit anti-mouse antibody which is linked to a reporter enzyme, horseradish peroxidase (HRPO). A similar ELISA assay has been developed by Lazaro et al., which is used for detection of a protein tyrosine kinase. See Lazaro et al., *Analytical Biochemistry* 192:257–261 (1991). Like the assay of Cleaveland et al., this assay also measures the ability of a protein tyrosine kinase to phosphorylate a synthetic substrate which is bound to microELISA wells.

A direct way to assess specific activation of rPTKs is by analysis of receptor autophosphorylation. See, e.g., Hunter and Cooper *Ann Rev Biochem* 54:897–930 (1985) and Ullrich and Schlessinger, *Cell* 61:203–212 (1990). Using this direct approach, Knutson and Buck disclose assays for measuring autophosphorylation of the insulin receptor under in situ or in vitro conditions (*Archives of Biochemistry and Biophysics* 285(2):197–204 [1991]). In the in situ assay, monolayer cultures of embryonic mouse 3T3-C2 fibroblasts (having the endogenous insulin receptor) are incubated with insulin in large cell culture dishes. Following incubation, the insulin receptor is extracted from the membranes. To achieve extraction of the insulin receptor, the cell monolayers are scraped into a buffer containing protease inhibitors and the cells are then disrupted in a homogenizer. The cellular homogenate is subsequently subjected to centrifugation for 60 min., and the pellet which forms is extracted into buffer containing detergent. Following a further centrifugation step, the supernatant (containing the insulin receptor) is incubated with an anti-insulin receptor antibody. Then, the receptor-antibody complex is incubated with protein A-agarose and unoccupied protein A sites are blocked with normal rabbit IgG. The agarose beads are then centrifuged, the supernatants aspirated and the pellets are re-suspended in buffer containing the radiolabelled anti-phosphotyrosine antibody. The amount of bound iodinated anti-phosphotyrosine antibody is consequently measured.

Klein and his colleagues discuss an assay for measuring insulin activation of the insulin receptor (Klein et al., *Diabetes* 42:883–890 [1993]). In this assay, aliquots of a heterogeneous population of mononuclear blood cells (including T cells, B cells, macrophages etc) having the insulin receptor are exposed to insulin in centrifuge tubes. The cells are then lysed in detergent using a motordriven homogenizer and the lysates are concentrated two- to four-fold using vacuum centrifugation. Sometimes, the insulin receptor is also partially purified using wheat germ agglutin agarose. The supernatants which form following centrifugation, are then transferred to anti-insulin receptor-coated microtiter plates. Insulin (8.7 nM) as well as kinase and phosphatase inhibitors are present during receptor immobilization in order to optimize the percentage of receptors captured to the microtiter plates. Activation of the insulin receptor is then measured by transphosphorylation of the substrate Poly-Glu, Tyr with $^{32}$P labeled ATP. The supernatants are then spotted onto absorbent paper and the paper is washed with cold TCA to remove unbound $^{32}$P-ATP. Remaining $^{32}$P-labeled Poly-Glu, Tyr on the washed absorbent paper is subsequently counted by scintillation counting.

Hagino et al. were also interested in studying the insulin receptor in patients (Hagino et al., *Diabetes* 43:274–280 [1994]). As a first step in the assay, Hagino et al. stimulate a primary cell suspension, which is not particularly homogeneous with respect to cell type. In particular, heparinized blood (1 ml washed twice with medium and resuspended in 1 ml of medium containing bovine serum albumin, BSA) is exposed to varying concentrations of insulin. The autophosphorylation reaction is stopped, the cells centrifuged for 30 min, the supernatant is discarded and the erythrocyte ghosts thus obtained are resuspended in buffer and centrifuged again. The pellet thereby obtained is adjusted to 500 μl and solubilized in detergent. The solubilized materials are then centrifuged and the resulting supernatant is subjected to sandwich ELISA (using anti-insulin receptor antibodies to capture the insulin receptor) to determine the extent of insulin receptor autophosphorylation.

Several others have used an enzyme-conjugated form of the anti-phosphotyrosine antibody in Western blot analyses which measure receptor autophosphorylation. Briefly, Western blotting generally involves electrophoresing activated rPTK on polyacrylamide gel. The rPTK is then transferred to nitrocellulose and immunoblotted with the anti-phosphotyrosine antibody which is labelled to enable detection. See, for example, Wang, *Molecular and Cellular Biology* 5(12):3640–3643 (1985); Glenney et al., *Journal of Immunological Methods* 109:277–285 (1988); Kamps, *Methods in Enzymology* 201:101–110 (1991); Kozma et al., *Methods in Enzymology* 201:28–43 (1991); Holmes et al., *Science* 256:1205–10 (1992); and Corfas et al., *PNAS. USA* 90:1624–1628 (1993). However, with Western blot analysis, accurate quantitation can be very tedious. Furthermore, this technique tends to be time-consuming and generally does not allow high sample throughput.

It is an object of the instant invention to provide a sensitive, reliable assay that measures receptor protein tyrosine kinase (rPTK) autophosphorylation. The assay is desirably useful for qualitatively and quantitatively measuring kinase activation as well as facilitating identification and characterization of potential agonists and antagonists for a selected rPTK. It is a further object of the invention to provide an assay which enables ligand-receptor interactions to be studied for any selected rPTK.

This assay must have a capacity for high throughput, that is, the ability to reliably evaluate large numbers of samples in a relatively short period of time (e.g., in one day). The assay ideally does not use radioactive materials and is also amenable to automation.

It is a further object, in at least one embodiment of the invention, to provide a generic assay which enables a rPTK of interest to be studied, regardless of whether or not a receptor-specific capture agent having the desired characteristics is available. Furthermore, it is an object of the invention to provide an assay which substantially represents the activity of the tyrosine kinase receptor in situ. This is desirable insofar as it reduces the possibility that altered interactions between the receptor and the ligand may occur as a consequence of the receptor not being membrane-bound. Furthermore, if the receptor is a multimeric complex, this assay enables the correctly assembled receptor to be studied.

These and other objects will be apparent to the ordinary artisan upon consideration of the specification as a whole.

SUMMARY OF THE INVENTION

Accordingly, the invention provides an assay for measuring activation (i.e., autophosphorylation) of a tyrosine kinase receptor of interest.

The assay can be divided into two major stages, each of which is generally performed in separate assay plates. The first stage of the assay involves activating the receptor and is termed the kinase receptor activation (KIRA) stage of the assay. The second stage of the assay involves measuring receptor activation. Conveniently, this is achieved using an enzyme-linked immunosorbent assay (ELISA) to measure receptor activation.

The KIRA stage of the assay involves activating a tyrosine kinase receptor which is located in the cell membrane of an eukaryotic cell such that the extracellular domain of the receptor faces the external milieu of the cell, the transmembrane domain is located in the cell membrane and the kinase domain is located intracellularly. This stage of the overall assay involves steps (a) to (c) below:

(a) The first solid phase (e.g., a well of a first assay plate) is coated with a substantially homogeneous population of cells (usually a mammalian cell line) so that the cells adhere to the solid phase. Often, the cells are adherent and thereby adhere naturally to the first solid phase. In one embodiment of the invention, the cells have an endogenous tyrosine kinase receptor presented in the cell membrane as discussed above. In an alternative embodiment, the cells have been transformed with DNA encoding a tyrosine kinase receptor or a "receptor construct" defined further below, which DNA is expressed by the cells such that the receptor or receptor construct is suitably positioned in the cell membranes thereof.

The receptor construct comprises a fusion of a kinase receptor and a flag polypeptide. The flag polypeptide is recognized by the capture agent, often a capture antibody, in the ELISA part of the assay. Use of a receptor construct as disclosed herein is particularly advantageous since it provides a "generic" assay wherein autophosphorylation of any tyrosine kinase receptor can be measured, regardless of whether or not a receptor-specific capture agent having the required characteristics is available. Often, the tyrosine kinase receptor is a fusion protein comprising the ECD of a selected tyrosine kinase and the catalytic ICD (and possibly the transmembrane domain) of another well characterized tyrosine kinase (e.g., the Rse receptor).

(b) An analyte is then added to the wells having the adhering cells, such that the tyrosine kinase receptor is exposed to (or contacted with) the analyte. This assay enables identification of agonist and antagonist ligands for the tyrosine kinase receptor of interest. In order to detect the presence of an antagonist ligand which blocks binding and/or activation of the receptor by an agonist ligand, the adhering cells are exposed to the suspected antagonist ligand first and then to the agonist ligand for to a mixture of the agonist and antagonist) so that competitive inhibition of receptor binding and activation can be measured. Also, the assay can identify an antagonist which binds to the agonist ligand and thereby reduces or eliminates its ability to bind to, and activate, the rPTK. To detect such an antagonist, the suspected antagonist and the agonist for the rPTK are incubated together and the adhering cells are then exposed to this mixture of ligands.

(c) Following exposure to the analyte, the adhering cells are solubilized using a lysis buffer (which has a solubilizing detergent therein) and gentle agitation, thereby releasing cell lysate which can be subjected to the ELISA part of the assay directly, without the need for concentration or clarification of the cell lysate. Thus, this assay provides a significant improvement over assays described by Knutson and Buck, supra, Klein et al., supra, and Hagino et al., supra, insofar as it is surprisingly unnecessary to concentrate the cell lysate prior to the ELISA. Furthermore, unlike the other assays, in the instant assay the cells can be lysed in lysis buffer using gentle agitation without the need for homogenizing, centrifuging or clarifying the cells. The cell lysate thus prepared is then ready to be subjected to the ELISA stage of the assay. It has been discovered that, surprisingly, the first assay plate can be stored at freezing temperatures (i.e., at about −20° to −70° C.) for significant periods of time (at least 6 months) before the ELISA stage of the assay. This is a significant finding insofar as the KIRA and ELISA stages of the assay can be performed on separate days.

The ELISA component of the assay comprises steps (d) to (h), described below.

(d) As a first step, the second solid phase (usually a well of an ELISA microtiter plate) is coated with a capture agent (often a capture antibody) which binds specifically to the tyrosine kinase receptor, or, in the case of a receptor construct, to the flag polypeptide. Coating of the second solid phase is carried out so that the capture agent adheres to the second solid phase. The capture agent is generally a monoclonal antibody, but, as is described in the examples herein, polyclonal antibodies may also be used.

(e) The cell lysate obtained in step (c) of the above-mentioned KIRA stage of the assay is exposed to, or contacted with, the adhering capture agent so that the receptor or receptor construct adheres to (or is captured in) the second solid phase. Unlike the assay of Klein et al., the instant assay does not require the ligand for the receptor as well as kinase inhibitors to be present to achieve suitable immobilization of the receptor or receptor construct to the second solid phase.

(f) A washing step is then carried out, so as to remove unbound cell lysate, leaving the captured receptor or receptor construct.

(g) The adhering or captured receptor or receptor construct is then exposed to, or contacted with, an anti-phosphotyrosine antibody which identifies phosphorylated tyrosine residues in the tyrosine kinase receptor. In the preferred embodiment, the anti-phosphotyrosine antibody is conjugated (directly or indirectly) to an enzyme which catalyses a color change of a non-radioactive color reagent. Accordingly, phosphorylation of the receptor can be measured by a subsequent color change of the reagent. The enzyme can be bound to the anti-phosphotyrosine antibody directly, or a conjugating molecule (e.g., biotin) can be conjugated to the anti-phosphotyrosine antibody and the enzyme can be subsequently bound to the anti-phosphotyrosine antibody via the conjugating molecule.

(h) Finally, binding of the anti-phosphotyrosine antibody to the captured receptor or receptor construct is measured, e.g., by a color change in the color reagent.

The invention also pertains to a Rse.flag reagent which is particularly useful for use in the KIRA ELISA assay. The Rse.flag reagent is a polypeptide comprising a fusion of a flag polypeptide (usually the gD flag described herein) to the carboxyl terminus of the intracellular domain of the Rse rPTK. Generally, the transmembrane domain of Rse and the extracellular domain of another rPTK of interest are also present in the fusion polypeptide reagent. The nucleic acid encoding this reagent and a cell transformed therewith are also claimed.

In yet a further aspect, the invention relates to a kit which can be used in the KIRA ELISA disclosed above which comprises an anti-flag polypeptide capture agent (e.g. a capture antibody) which is usually bound to the second solid phase as described herein. Thus, the kit generally provides an ELISA microtiter plate having an anti-flag polypeptide capture antibody adhering to a well thereof. Optionally, the kit also provides an anti-phosphotyrosine antibody which is often labelled, or reagents for labelling the anti-phosphotyrosine antibody are supplied with the kit. Sometimes, a homogeneous population of cells which have been transformed with a receptor construct as described herein are also provided with the kit. The kit also suitably includes instructions for carrying out the KIRA ELISA.

BRIEF DESCRIPTION OF THE DRAWINGS

FIGS. 1A–1C are diagrammatic representations of Rse.gD (FIG. 1A), Receptor ECD/Rse.gD chimera (FIG. 1B) and a CHO cell transformed with the Receptor ECD/Rse.gD chimera (FIG. 1C).

FIGS. 2A–2C depict an alignment of the amino acid sequence (SEQ ID NO: 1) and nucleotide sequence (SEQ ID NO: 2) of Rse.gD. The residues of the signal sequence are indicated with an (*), the transmembrane domain of Rse is boxed and the ECD and ICD of Rse are also delineated. The residues of the gD flag sequence are underlined.

FIG. 3 is a flow diagram of an exemplary strategy for selecting a suitable capture agent for use in the assay.

FIG. 4 is a flow diagram of an exemplary strategy for selecting a transformed cell suitable for use in the assay, where the cell has a receptor construct with an amino-terminal flag polypeptide located in the cell membrane thereof.

FIG. 5 is a flow diagram of an exemplary strategy for selecting a transformed cell suitable for use in the assay, where the cell has a receptor construct with a carboxyl-terminal flag polypeptide located in the cell membrane thereof.

FIGS. 6A–6B is a flow chart and cartoon illustrating the KIRA ELISA assay for the HER2 receptor described in Example 1.

FIG. 7 depicts a p185$^{HER2}$/HRGβ1$_{177-244}$ KIRA ELISA standard curve obtained using the assay described in Example 1. To obtain the standard curve, MCF-7 cells (2×10$^5$) were stimulated with 3000, 1000, 333, 111, 37, 12, 4, or 0 pM HRGβ1$_{177-244}$, as determined by quantitative amino acid analysis (q.a.a.a.). Each calibrator concentration was run in triplicate. The values derived from 10 such standard curves were averaged (total n=30) and are presented as mean ABS$_{450/650}$±sd vs. HRGβ1$_{177-244}$ concentration.

FIG. 8 depicts heregulin specificity of p185$^{HER2}$/HRG KIRA ELISA of Example 1. In the assay, MCF-7 cells (2×10$^5$) were stimulated with either HRGβ1$_{177-244}$ (■) at 3000, 1000, 333, 111, 37, 12, 4 or 0 pM or IGF-1 (▲), EGF (□), VEGF (●) or insulin (♦) at 30000, 1 0000, 3333, 1111, 370, 120, 40 or 0 pM. For all concentrations of ligands, n=3 and data are presented as average ABS$_{450/650}$±sd vs. ligand concentration.

FIGS. 9A–9B is a flow chart and cartoon illustrating the KIRA ELISA assay for the Rse receptor described in Example 2.

FIG. 10 depicts a Rse KIRA ELISA standard curve obtained using the assay described in Example 2. To obtain the standard curve, CHO cells transformed with the Rse.gD construct were stimulated with 1:100, 1:200, 1:400, 1:800, 1:1600, 1:3200 or 0 diluted, anti-Rse agonist antibody. Each calibrator concentration was run in triplicate. The values are presented as mean ABS$_{450/650}$±sd vs. 1/dilution agonist antibody.

FIGS. 11A–11B is a flow chart and cartoon illustrating the KIRA ELISA assay for the trk receptors (i.e., trk A, trk B, and trk C) described in Example 3.

FIGS. 12A–12G depict an alignment of the amino acid acid sequence (SEQ ID NO: 3) and nucleotide sequence (SEQ ID NO: 4) of gD.trk A used in the assay described in Example 3. The residues of the signal sequence are indicated with an (*), the residues of the gD flag sequence are underlined, the residues of the transmembrane domain of trk A are in bold and the ECD and ICD thereof are also delineated.

FIGS. 13A–13G depict an alignment of the amino acid sequence (SEQ ID NO: 5) and nucleotide sequence (SEQ ID NO: 6) of gD.trk B used in the assay described in Example 3. The residues of the signal sequence are indicated with an (*), the residues of the gD flag sequence are underlined, the residues of the transmembrane domain of trk B are in bold and the ECD and ICD thereof are also delineated.

FIGS. 14A–14G depict an alignment of the amino acid sequence (SEQ ID NO: 7) and nucleotide sequence (SEQ ID NO: 8) of gD.trk C used in the assay described in Example 3. The residues of the signal sequence are indicated with an (*), the residues of the gD flag sequence are underlined, the residues of the transmembrane domain of trk C are in bold and the ECD and ICD thereof are also delineated.

FIGS. 15A–15C depict standard curves for trk A, B and C, respectively, which were obtained using the assay described in Example 3. To obtain the standard curves, CHO cells transformed with the gD.trk constructs were stimulated with 3000, 1000, 333, 111, 37, 12, 4 or 0 pM of ligand, i.e. nerve growth factor (NGF, ■), neurotrophin 3 (NT3, ●) or neurotrophin 5 (NT5, ▲). The values are presented as mean ABS$_{450/650}$±sd vs. ligand concentration.

FIGS. 16A–16Z depict the nucleotide sequence (SEQ ID NO: 9) of the pSVl17.ID.LL expression vector used for expression of Rse.gD in Example 2.

DETAILED DESCRIPTION OF THE PREFERRED EMBODIMENTS

I. Abbreviations and Definitions

"rPTK" means a receptor protein tyrosine kinase.

"ECD", "TM domain" and "ICD" refer to the extracellular domain, transmembrane domain and intracellular domain of a rPTK, respectively.

"Kinase Receptor Activation" or "KIRA" when used throughout this application refers to the first stage of the instantly claimed assay wherein a cell-bound rPTK is exposed to a potential agonist/antagonist ligand which may (or may not) induce phosphorylation of tyrosine residues in the intracellular domain of the rPTK. The KIRA is generally carried out in the "first assay plate" as defined herein.

"Enzyme-Linked Immunosorbent Assay" or "ELISA" refers to the second stage of the instantly claimed assay and involves measuring tyrosine phosphorylation of the rPTK. The ELISA is normally carried out in the "second assay plate" as disclosed in this application. The ELISA is a "sandwich ELISA" insofar as it involves capturing the rPTK or receptor construct to the second solid phase (usually the well of an ELISA microtiter plate). ELISA assays generally involve the preparation of enzyme-antibody conjugates. The conjugated enzyme cleaves a substrate to generate a colored reaction product that can be detected spectrophotometrically. In this assay, the absorbance of the colored solution in individual microtiter wells is proportional to the amount of phosphotyrosines. A review of ELISA is found in Current Protocols in Molecular Biology, Vol. 2, chapter 11 (1991). While the term "ELISA" is used to describe the second stage of the instant assay, it is only a preferred embodiment of the invention, since, as disclosed herein, techniques other than enzymatic detection are available for measuring binding of the anti-phosphotyrosine antibody to the activated receptor.

The terms "receptor", "kinase receptor", "tyrosine kinase", "tyrosine kinase receptor", "receptor protein tyrosine kinase" and "rPTK" are used interchangeably herein and refer to a protein having at least one phosphate accepting phenolic group. The protein is usually a receptor insofar as it has a ligand-binding ECD, TM domain and ICD. The ICD usually comprises a catalytic kinase domain and has one or more phosphate accepting tyrosine residues. See FIGS. 1A and 1B, for example. Examples of tyrosine kinase receptors include the insulin receptor, insulin related receptor, epidermal growth factor receptor (EGF-R), platelet-derived growth factor receptors A and B (PDGF-R-A and PDGF-R-B), insulin-like growth factor 1 receptor (IGF-1-R), macrophage colony-stimulating factor receptor (M-CSF-R), HER2/neu/c-erbB-2 receptor, HER3/c-erbB-3 receptor, Xmrk receptor, IRR receptor, fibroblast growth factor (FGF) receptors bek and flg, c-kit receptor, Flk/kDR receptor, Rse receptor, the Eph, Elk, Eck, Eek, Erk, Cek4/Mek4/HEK and Cek5 receptors, Axl receptor, hepatocyte growth factor receptor (HGF-R), Flt1 VEGF receptor, SAL-S1 receptor, HpTK 5 receptor, trkA receptor, trkB receptor, and trkC receptor. See, for example, Ullrich and Schlessinger Cell 81:203–212 (1990); Fantl et al., Annu. Rev. Biochem. 62:453–481 (1993); Mark et at., Journal of Biological Chemistry 269(14):10720–10728(1994); and WO 93/15201.

The terms mentioned above encompass chimeric "receptor" molecules which comprise at least the extracellular domain of a selected tyrosine kinase and the intracellular domain, and, optionally, the transmembrane domain of another tyrosine kinase. Of course, the tyrosine kinase of interest can provide the transmembrane domain and/or intracellular domain. The terms also encompass amino acid sequence variants and covalent derivatives of the various rPTKs provided they still display tyrosine kinase phosphorylation activity in the KIRA ELISA. Therefore, the variants will general have conservative amino acid alterations. The individual domains of the tyrosine kinase can be delineated based on sequence homology to known tyrosine kinases and hydrophobicity plots. For example, the hydrophobic transmembrane domain can be readily determined and the ECD and ICD are usually amino-terminal and carboxyl terminal to the transmembrane domain, respectively. Conveniently, the transmembrane domain and ICD of the Rse receptor can be fused to the ECD of a tyrosine kinase of interest, thereby forming a chimeric receptor which is encompassed by the terms denoting a receptor as mentioned above.

In the preferred embodiment, the rPTK is selected from the group consisting of HER2 receptor (Ullrich and Schlessinger, supra), Rse receptor (Mark et al., supra and SEQ ID NO: 1), trk A receptor (SEQ ID NO: 3), trk B receptor (SEQ ID NO: 5) and trk C receptor (SEQ ID NO: 7).

By "autophosphorylation" is meant activation of the catalytic kinase domain of the rPTK, whereby at least one intrinsic tyrosine residue is phosphorylated. Generally, autophosphorylation will result when an agonist molecule binds to the extracellular domain of the kinase receptor. Without being limited to any particular mechanism of action, it is thought that binding of the agonist molecule may result in oligomerization of the kinase receptor which causes activation of the catalytic kinase domain.

By "solid phase" is meant a non-aqueous matrix to which the cells (in the KIRA stage of the assay) or the capture agent (in the ELISA stage of the assay) can adhere. Usually, the solid phase comprises the well of an assay plate but the invention is by no means limited to this embodiment. For example, the solid phase can comprise a discontinuous solid phase of discrete particles. The particles can be porous and formed from a number of different materials, e.g., polysaccharides (e.g. agarose), polyacrylamides, polystyrene, polyvinyl alcohol, silicones and glasses. For examples of suitable particulate solid phases, see U.S. Pat. No. 4,275,149.

By "well" is meant a recess or holding space in which an aqueous sample can be placed. The well is provided in an "assay plate". The invention usually employs a "first assay plate" which is formed from a material (e.g. polystyrene) which optimizes adherence of cells (having the receptor or receptor construct) thereto. Generally, the individual wells of the first assay plate will have a high surface area to volume ratio and therefore a suitable shape is a flat bottom well (where the cells are adherent). The "second assay plate" is generally formed from a material (e.g. polystyrene) which optimizes adherence of the capture agent thereto. The second assay plate may have the same general construction and/or characteristics as the first assay plate. However, separate plates are used for the KIRA stage of the assay and the ELISA stage of the assay.

In the preferred embodiment of the invention, both the first assay plate and the second assay plate are "microtiter" plates. The term "microtiter" plate when used herein refers to an assay plate having between about 30 to 200 individual wells, usually 96 wells. Often, the individual wells of the microtiter plate will hold a maximum volume of about 250 $\mu$l. Conveniently, the first assay plate is a 96 well polystyrene or plastic, cell culture microtiter plate (such as that sold by Becton Dickinson Labware, Lincoln Park, N.J.), which allows for automation. Often, about 50 $\mu$l to 300 $\mu$l, more preferably 100 $\mu$l to 200 $\mu$l, of an aqueous sample comprising cell culture media with the cells suspended therein will be added to each well of the first assay plate in the KIRA stage of the assay. It is desirable to seed between about $1\times10^4$ to $3\times10^5$ cells per well. More preferably, $5\times10^4$ to $1\times10^5$ cells per well are seeded. Usually, the second assay plate will comprise a polystyrene microtiter ELISA plate such as that sold by Nunc Maxisorp, Inter Med. Denmark.

The term "homogeneous population of cells" refers to a substantially homogeneous population of cells wherein at least about 80%, and preferably about 90%, of the cells in the population are of the same cell type. Therefore, it is convenient to use a cell line. The cell line is a eukaryotic cell line, normally an animal cell line and desirably a mammalian cell line.

The cells have, or are transformed to produce, the selected receptor or a receptor construct. For example, where the kinase receptor is known to be present in a certain cell line (e.g., the HER2 receptor in the MCF-7 cell line) no transformation step is required. Conversely, it may be necessary to transform a cell with a nucleic acid encoding the receptor, where the cell does not make the receptor, or does not have suitable numbers of the receptor in the cell membrane thereof. Accordingly, the cell is transformed with a nucleic acid encoding the receptor (or receptor construct) and the nucleic acid is expressed so that the ECD of the receptor faces the external milieu of the cell, the transmembrane domain is located in the cell membrane and the kinase domain is located intracellularly.

Where the assay relies on activating the endogenous rPTK, a cell line is selected which is known to produce the rPTK of interest, provided sufficient levels of the rPTK are present in the cell membrane thereof to enable detection. As a general proposition, a minimum number of about $1\times10^4$ receptors/cell is required. For example, the MCF-7 cell line (ATCC-HTB 22) which produces the HER2 receptor was shown to be useful in the assay. There are $5\times10^4$ HER2 receptors/MCF-7 cell. Examples of other cell lines and their respective rPTKs include, embryonic mouse 3T3-C2 fibroblast cell line and the insulin receptor, and Hep 3B (ATCC # HB 8064) cell line and the Rse receptor. However, the degree of expression of the rPTK nucleic acid in the cell line is not so high that it results in constitutive phosphorylation of the rPTK. For example, the SK-BR-3 cell line (ATCC HTB30), which has $3\times10^6$ HER2 receptors/cell, was found to be unsuitable for use in the assay disclosed herein. Therefore, it may be useful to use a cell line which has less than about $3\times10^6$ receptors/cell, depending on the type of receptor. The number of receptors/cell can be measured using Scatchard analysis, for example (Scatchard, *Ann. NY Acad. Sci.* 51:660–672 [1949]; and Goodwin et al., *Cell* 73:447–456 [1993]). However, selection of a cell line having a suitable number of receptors/cell is possible using the techniques described herein.

The term "adherent" when used herein to describe the cell, refers to a cell which naturally adheres to the first solid phase (often the well of the first assay plate), thereby forming a fairly uniform coating of the cells on the inside surface of the well. The uniform coating of cells generally forms following incubation of the cells in the wells of the first assay plate for about 8–16 hours. After incubation, non-adhering cells and cell culture medium are decanted off the first assay plate. Incubation is usually carried out at a temperature which is optimal for cell growth, i.e, about 37° C. Examples of adherent cell lines include CHO cells (Urlaub and Chasin, *Proc. Natl. Acad. Sci. USA* 77:4216 [1980]), MCF-7 cells (ATCC HB 22), 293 cells (Graham et al., *J. Gen Virol.* 36:59 [1977], Swiss albino 3T3 fibroblast cell line (ATCC No. CCL 92) and U937 macrophage cell line (ATCC No. CRL 1593).

A "flag polypeptide" comprises a short polypeptide which has enough residues to provide an epitope (preferably a linear epitope) against which a "capture agent" thereagainst can be made, yet is short enough such that it does not interfere with activity of the rPTK. The flag polypeptide is also sufficiently unique so that the capture agent thereagainst does not bind to other reagents in the assay. Selection of a "unique" flag polypeptide sequence can be accomplished by comparing the sequence of a proposed flag polypeptide against other known sequences in Genbank or EMBL, for example. Suitable flag polypeptides generally have at least 6 amino acid residues and usually between about 8–80 amino acid residues (preferably between about 9–30 amino acid residues).

By "receptor construct" is meant a polypeptide which comprises a fusion of a kinase receptor and a flag polypeptide as defined above. The flag polypeptide is provided at a location in the receptor construct such that: a) the flag polypeptide does not interfere with ligand binding to the receptor; b) the flag polypeptide does not interfere with autophosphorylation of the receptor and c) the flag polypeptide is presented in a suitable configuration so that it can bind to the capture agent in the ELISA stage of the assay. Often, the polypeptide flag will be present at the N-terminus of the receptor construct. See, for example, Example 3 which refers to the gD.trk constructs. Alternatively, the flag polypeptide may be present at the C-terminus of the receptor construct. See, for example, Example 2 which refers to the Rse.gD construct. See also FIGS. 1A–1C. The Rse construct disclosed herein is particularly useful, since the ICD (and optionally the transmembrane domain) thereof can be fused to the ECD of a kinase receptor of interest, thereby obviating the need to establish where the flag polypeptide should be located with respect to the kinase receptor of interest.

"Rse.gD" refers to a receptor construct which is the Rse receptor protein tyrosine kinase with the Herpes Simplex virus glycoprotein D (gD) flag polypeptide fused to the COOH-terminus thereof.

"Rse.flag reagent" refers to a polypeptide which comprises the ICD of the Rse receptor fused at its COOH-terminus to a flag polypeptide (normally the gD flag polypeptide). Sometimes, the TM domain of Rse and the ECD of a rPTK of interest will also be present in the Rse.gD reagent. "Receptor ECD/Rse.gD Chimera" refers to a fusion of the ECD of a rPTK of interest to the TM and ICD domains of Rse which are fused COOH-terminally to the gD flag polypeptide.

"gD.trkA", "gD.trkB" and "gD.trkC" refer to each of the trk receptors (A–C) having the gD flag polypeptide fused to the amino-termini thereof.

By "capture agent" is meant a compound or agent which is able to adhere to the second solid phase, as herein defined, and which is selective for a rPTK or receptor construct. Thus, the capture agent captures the receptor or receptor construct to the wells of the second assay plate. Usually, the capture agent binds selectively to the flag polypeptide which has been fused to the receptor of interest. Binding of the capture agent is not affected by the presence or absence of ligand bound to the receptor and does not induce receptor activation upon capture. Furthermore, the capture agent does not sterically block access to the phosphorylated tyrosine(s) by the anti-phosphotyrosine antibody. Means for selecting suitable capture agents are described herein. Generally, the capture agent will comprise an antibody (e.g., an affinity purified polyclonal antibody or a monoclonal antibody), but other selective agents, such as streptavidin which binds selectively to the "strep-tag" polypeptide can also be used (see Schmidt et al., Protein Engineering 6(1):109–122 [1993]). Streptavidin can be purchased commercially from Zymed Laboratories, S. San Francisco, Calif., for example.

Alternatively, the capture agent can comprise protein A (which binds specifically to immunoglobulins). In this embodiment of the invention, the activated receptor or receptor-construct present in the cell lysate is incubated with an antibody which binds specifically thereto, thereby forming a receptor-antibody complex. This complex can be captured by protein A by virtue of its specific binding to the antibody present in the complex. Protein A can be purchased commercially from Pharmacia Biotech, Inc., Piscataway, N.J., for example. A strategy for selecting a suitable capture agent is depicted in FIG. 3 and will be described in more detail later herein.

In the most preferred embodiment, the capture agent is a monoclonal antibody which binds specifically to a flag polypeptide (which is present in the receptor construct). Examples of suitable flag polypeptides and their respective capture antibodies include the flu HA flag and its antibody 12CA5, (Field et al, Mol. Cell. Biol. 8:2159–2165 [1988]); the c-myc flag and the 8F9, 3C7, 6E10, G4, B7 and 9E10 antibodies thereto (Evan et a., Molecular and Cellular Biology 5(12):3610–3616 [1985]); as well as the Herpes Simplex virus glycoprotein D (gD) flag and the 5B6 antibody thereto (Paborsky et al., Protein Engineering 3(6) :547–553 [1990] and Mark et al., Journal of Biological Chemistry 269(14):10720–10728[1994]). Other flag polypeptides have been disclosed. Examples include the Flag-peptide (Hopp et al., BioTechnology 6:1204–1210 [1988]); the KT3 epitope peptide (Martin et al., Science 255:192–194 [1992]); an a-tubulin epitope peptide (Skinner et al., J. Biol. Chem 266:15163–15166 [1991]); and the T7 gene 10 protein peptide tag (Lutz-Freyermuth et al., Proc. Natl. Acad. Sci. USA 87:6393–6397 [1990]). Once the flag polypeptide has been selected as discussed above, a capture antibody thereto can be generated using the techniques disclosed herein.

The term "analyte" refers to a compound or composition to be studied, usually to investigate its ability to activate (or prevent activation of) the tyrosine kinase receptor of interest. The analyte can comprise a bodily fluid (such as plasma or amniotic fluid) or a composition known to contain, or suspected of containing, a ligand for the tyrosine kinase receptor. The analyte can also comprise a cell which has a ligand to the rPTK of interest.

"Ligand" when used herein refers to a molecule which is able to bind to the ECD of the tyrosine kinase of interest or to a known agonist for the tyrosine kinase of interest. The ligand will usually be an agonist or antagonist for the tyrosine kinase.

By "agonist" is meant a molecule which is able activate the intracellular kinase domain of the tyrosine kinase upon binding to the ECD. Often, the agonist will comprise a growth factor (i.e., a polypeptide that is able to stimulate cell division). Exemplary growth factors include heregulin (HRG), insulin, insulin-like growth factors I and II (IGF-I and IGF-II), epidermal growth factor (EGF), interleukins (e.g., IL-8), macrophage colony-stimulating factor (M-CSF), erythropoietin (EPO), platelet-derived growth factor (PDGF), fibroblast growth factor (FGF), transforming growth factors alpha and beta (TGF-$\alpha$ and TGF-$\beta$), hepatocyte growth factor (HGF), and nerve growth factor (NGF). Alternatively, the agonist can be antibody against the rPTK (see, e.g., Yarden, Proc. Natl. Acad. Sci. USA 87:2569–2573 [1990]). However, other non-protein agonists such as small organic molecules are also encompassed by the invention.

By "antagonist" is meant a molecule which blocks agonist action. Usually, the antagonist will either: (a) bind to the rPTK and thereby block binding and/or activation of the rPTK by an agonist thereto (the antagonist may bind to the ECD of the rPTK, but this is not necessarily the case) or (b) bind to the agonist and thus prevent activation of the rPTK by the agonist. This assay facilitates the detection of both types of antagonist. The antagonist may, for example, comprise a peptide fragment comprising the receptor binding domain of the endogenous agonist ligand for the receptor. The antagonist may also be an antibody which is directed against the ECD of the rPTK, or against a known agonist for the rPTK. However, other non-protein molecules are also encompassed by this term.

The term "antibody" is used in the broadest sense and specifically covers monoclonal antibodies and antibody compositions with polyepitopic specificity (i.e. polyclonal antibodies). The polyclonal antibodies are preferably "affinity purified" antibodies. The term "affinity purified" means that the antibodies have been purified using the antigen (e.g. the rPTK or fragment thereof or the flag polypeptide) to selectively purify the polyclonal antibodies. Affinity purification can be achieved by immobilizing the antigen on an affinity column (e.g. an agarose column) and passing the polyclonal antibodies through the column. The affinity purified antibodies can be subsequently eluted from the column by changing the elution conditions or by adding a chaotropic agent, for example. For a review of affinity purification techniques with respect to antibodies, see *Current Protocols in Immunology*, Ed. Coligen et al., Wiley publishers, Vols. 1 and 2, for example.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of a selected antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. [See, e.g. U.S. Pat. No. 4,816,567 and Mage & Lamoyi, in *Monoclonal Antibody Production Techniques and Applications*, pp.79–97 (Marcel Dekker, Inc., New York (1987)].

Thus, the modifier "monoclonal" indicates the character of the antibody as being obtained from a substantially homogeneous population of antibodies, aid is not to be construed as requiring production of the antibody by any particular method. For example, the monoclonal antibodies to be used in accordance with the present invention may be made by the hybridoma method first described by Kohler & Milstein, *Nature*, 256:495 (1975), or may be made by recombinant DNA methods (U.S. Pat. No. 4,816,567). The "monoclonal antibodies" may can also be isolated from phage antibody libraries using the techniques described in Clackson et al., *Nature*, 352:624–628 (1991) and Marks et al., *J. Mol. Biol.*, 222:581–597 (1991), for example.

The term "anti-phosphotyrosine antibody" refers to a molecule, usually an antibody, which binds selectively to phosphorylated tyrosine residues in the kinase domain of a rPTK. The antibody can be polyclonal, but is desirably a monoclonal antibody. Anti-phosphotyrosine polyclonal antibodies can be made using the techniques disclosed in White and Backer, *Methods in Enzymology* 201:65–67 [1991] and monoclonal anti-phosphotyrosine antibodies can be obtained commercially from Upstate Biologicals, Inc. (UBI, Lake Placid, N.Y.), for example.

The word "label" when used herein refers to a detectable compound or composition which is conjugated directly or indirectly with a molecule (such as the anti-phosphotyrosine antibody). The label may be detectable by itself (e.g. radioisotope labels or fluorescent labels) or, in the case of an enzymatic label, may catalyze a chemical alteration of a substrate compound or composition which is detectable. The preferred label is an enzymatic one which catalyzes a color change of a non-radioactive color reagent.

By "washing" is meant exposing the solid phase to an aqueous solution (usually a buffer or cell culture media) in such a way that unbound material (e.g., non-adhering cells, non-adhering capture agent, unbound ligand, receptor, receptor construct, cell lysate, or anti-phosphotyrosine antibody) is removed therefrom. To reduce background noise, it is convenient to include a detergent (e.g. Triton X) in the washing solution. Usually, the aqueous washing solution is decanted from the wells of the assay plate following washing. Conveniently, washing can be achieved using an automated washing device. Sometimes, several washing steps (e.g., between about 1 to 10 washing steps) may be required.

By "block buffer" is meant an aqueous, pH buffered solution containing at least one blocking compound which is able to bind to exposed surfaces of the second solid phase which are not coated with capture agent. The blocking compound is normally a protein such as bovine serum albumin (BSA), gelatin, casein or milk powder and does not cross-react with any of the reagents in the assay (e.g., the anti-phosphotyrosine antibodies and detection reagents). The block buffer is generally provided at a pH between about 7 to 7.5 and suitable buffering agents include phosphate and TRIS.

By "lysis buffer" is meant an aqueous, pH buffered solution comprising a solubilizing detergent, one or more protease inhibitors and at least one phosphatase inhibitor (such as sodium orthovanadate). The term "solubilizing detergent" refers to a water miscible, non-ionic detergent which lyses cell membranes of eukaryotic cells but does not denature or activate the receptor or receptor construct. Examples of suitable non-ionic detergents include Triton-X 100, Tween 20, CHAPS and Nonidet P-40 (NP40) available from Calbiochem, La Jolla, Calif., for example. Many other non-ionic detergents are available in the art. Examples of suitable protease inhibitors include phenylmethylsulfonyl fluoride (PMSF), leupeptin, pepstatin, aprotinin, 4-(2-aminoethyl)-benzenesulfonyl fluoride hydrochloride-bestatin, chymostatin and benzamidine. Preservatives (e.g., thimerosal) and one or more compounds which maintain the isotonicity of the solution (e.g., sodium chloride [NaCl] or sucrose) and a buffer (e.g., Tris or PBS) are usually also present. Generally, the pH of the lysis buffer is in the range about 7 to 7.5.

Usually, following addition of the lysis buffer to the first assay plate, the first assay plate is "gently agitated" and this expression refers to the act of physically shaking the first assay plate (normally using a circular motion) at a substantially low velocity. Gentle agitation does not involve mechanically disrupting the cells (e.g. by homogenizing or centrifuging the cells). Exemplary shaking velocities are in the order of 200 to 500 rpm, preferably 300 to 400 rpm in a Bellco orbital shaker, for example.

II. Modes for Practicing the Invention

1. Kinase Receptor Activation—KIRA

The first stage of the assay involves phosphorylation of the kinase domain of a kinase receptor, wherein the receptor is present in the cell membrane of a eukaryotic cell. The receptor may be an endogenous receptor or nucleic acid encoding the receptor may be transformed into the cell. In one embodiment of the invention, nucleic acid encoding a receptor construct is transformed into the cell. Exemplary techniques for transforming the cell with either the receptor or the receptor construct nucleic acid follow.

A. Transformation of the cells

The instant invention provides a substantial improvement over soluble kinase receptor assays insofar as it is considered to more accurately reflect the activity of the receptor in situ. It has been discovered that it is possible to transform eukaryotic cells with a receptor construct (comprising the kinase receptor and either an amino- or carboxyl-terminal flag polypeptide) so that the receptor construct assembles itself appropriately in the cell membrane and still retains tyrosine kinase activity which can be detected in the ELISA stage of the assay. This provides a generic assay for measuring tyrosine kinase activity of any tyrosine kinase of interest.

If a suitable capture agent as described herein is available for a selected rPTK, cells can be transformed with the nucleic acid encoding the receptor alone, without the flag polypeptide. Alternatively, if cells are available which produce the receptor (e.g., MCF-7 cells which produce the HER2 receptor), it is not necessary to transform the cells for use in the assay.

In order to transform the cells with the nucleic acid encoding the rPTK or receptor construct, nucleic acid encoding the rPTK and, optionally, the flag polypeptide, is isolated. This can be achieved by screening a cDNA or genomic library known to contain the DNA encoding the rPTK or flag polypeptide of interest with a selected labelled probe (e.g., an antibody or oligonucleotide-probe) for the rPTK or flag polypeptide, using standard procedures as described in chapters 10–12 of Sambrook et al., *Molecular Cloning: A Laboratory Manual* (New York: Cold Spring Harbor Laboratory Press, 1989), for example. Alternatively, the nucleic acid encoding the flag polypeptide can be made synthetically using an oligo-synthesizing machine (Applied Biosystems, Calif.). An alternative means to isolate the nucleic acid encoding the rPTK or flag polypeptide is to use PCR methodology as described in section 14 of Sambrook et al, supra. Isolation of only the ECD of the rPTK of interest is required, since this nucleic acid can be fused to the nucleic acid encoding the TM and ICD of the Rse-flag polypeptide construct disclosed herein. See FIGS. 1A–1C and SEQ ID NOS:1 and 2. If necessary however, conventional primer extension procedures as described in section 7.79 of Sambrook et al., supra, can be used to detect precursors and processing intermediates of mRNA that may not have been reverse-transcribed into cDNA.

A preferred method of practicing this invention is to use carefully selected oligonucleotide sequences to screen cDNA libraries from various tissues, preferably mammalian cell lines having the rPTK of interest. The oligonucleotide sequences selected as probes should be of sufficient length and sufficiently unambiguous that false positives are minimized.

The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

In order to provide nucleic acid encoding a receptor construct, nucleic acid encoding the rPTK is fused at its 3' end to nucleic acid encoding the N-terminus of the flag polypeptide. Alternatively, the nucleic acid encoding the rPTK will be fused at its 5' end to nucleic acid encoding the carboxyl terminus of the flag polypeptide. Thus, the flag polypeptide is provided at either the carboxyl- or amino-terminus of the receptor construct. Examples of suitable flag polypeptides are provided above. Selection of other suitable flag polypeptides is possible using the techniques described herein.

In order to generate fusions between the Rse.flag reagent and a rPTK of interest, the nucleic acid encoding the ECD of the rPTK of interest is fused at its 3' end to the nucleic acid encoding the amino terminus of the Rse.flag reagent.

The nucleic acid (e.g., cDNA or genomic DNA) encoding the rPTK or receptor construct is then inserted into a replicable vector for further cloning (amplification of the DNA) or for expression. Many vectors are available to the skilled practitioner but must be compatible with the cell which is to be used in the assay. The vector will have vector components the presence of which will depend on various factors. Such components include, for example, a signal sequence, an origin of replication, one or more marker genes, an enhancer element, a promoter, and a transcription termination sequence. Selection of these vector components shall be described below.

Incorporation of a signal sequence into the expression vector is required since the rPTK or receptor construct must be transported to the cell membrane where it is positioned such that the ECD faces the external milieu of the cell. Therefore, a signal sequence suitable for positioning the rPTK or receptor construct in such a manner is used. The signal sequence is generally a component of the vector, or it may be a part of the rPTK or receptor construct DNA that is inserted into the vector. If a heterologous signal sequence is used, it is from those that are recognized and processed (i.e., cleaved by a signal peptidase) by the host cell.

For yeast secretion the native signal sequence may be substituted by, e.g., the yeast invertase leader, alpha factor leader (including Saccharomyces and Kluyveromyces α-factor leaders, the latter described in U.S. Pat. No. 5,010, 182 issued 23 Apr. 1991), or acid phosphatase leader, the *C. albicans* glucoamylase leader (EP 362,179 published 4 Apr. 1990), or the signal described in WO 90/13646 published 15 Nov. 1990. In mammalian cells expression of the DNA encoding the native signal sequence (e.g., the rPTK pre-sequence that normally directs secretion of rPTK from mammalian cells in vivo) is satisfactory, although other mammalian signal sequences may be suitable, such as signal sequences from other animal rPTKs, and signal sequences from secreted polypeptides of the same or related species, as well as viral secretory leaders, for example, the herpes simplex gD signal.

The DNA for such precursor region is ligated in reading frame to DNA encoding the rPTK or receptor construct.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. The 2 μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transformed into another organism for expression. For example, a vector is cloned in E.coli and then the same vector is transformed into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transformation of Bacillus with this vector results in homologous recombination with the genome and insertion of rPTK or receptor construct DNA. However, the recovery of genomic DNA encoding the rPTK or receptor construct is more complex than that of an exogenously replicated vector because restriction enzyme digestion is required to excise the rPTK or receptor construct DNA.

Expression and cloning vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

One example of a selection scheme utilizes a drug to arrest growth of a host cell. Those cells that are successfully transformed with a heterologous gene express the DNA encoding a protein conferring drug resistance and thus survive the selection regimen. Examples of such dominant selection use the drugs neomycin (Southern et al., *J. Molec. Appl. Genet.* 1:327 [1982]), mycophenolic acid (Mulligan et al., *Science* 209:1422 [1980]) or hygromycin (Sugden et al., *Mol. Cell. Biol.* 5:410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the rPTK or receptor construct nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the rPTK or receptor construct. Amplification is the process by which genes in greater demand for the production of a protein critical for growth are reiterated in tandem within the chromosomes of successive generations of recombinant cells. Increased quantities of rPTK or receptor construct are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA* 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the rPTK or receptor construct. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding the rPTK or receptor construct, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature* 282:39 [1979]; Kingsman et al., *Gene* 7:141 [1979]; or Tschemper et al., *Gene* 10:157 [1980]). The trp1 gene provides a selection marker for a mutant strain of yeast lacking the ability to grow in tryptophan, for example, ATCC No.44076 or PEP4-1 (Jones, *Genetics* 85:12 [1977]). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD can be used for transformation of Kluyveromyces yeasts. Bianchi et al., *Curr Genet.* 12:185 (1987). More recently, an expression system for large-scale production of recombinant calf chymosin was reported for *K. lactis*. Van den Berg, *Bio/Technology* 8:135 (1990). Stable multicopy expression vectors for secretion of mature recombinant human serum albumin by industrial strains of Kluyveromyces have also been disclosed. Fleer et al., *Bio/Technology* 9:968–975 (1991).

Expression and cloning vectors usually contain a promoter that is recognized by the host organism and is operably linked to the rPTK or receptor construct nucleic acid. Promoters are untranslated sequences located upstream (5') to the start codon of a structural gene (generally within about 100 to 1000 bp) that control the transcription and translation of particular nucleic acid sequence, such as the rPTK nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to rPTK or receptor construct-encoding DNA by removing the promoter from the source DNA by restriction enzyme digestion and inserting the isolated promoter sequence into the vector. Both the native rPTK promoter sequence and many heterologous promoters may be used to direct amplification and/or expression of the rPTK or receptor construct DNA. The promoter will be one which results in the accumulation of suitable numbers of receptor or receptor construct in the cell membrane of the transformed cell (i.e. so that autophosphorylation of the receptor is detectable in the ELISA but constitutive phosphorylation does not occur). Selection of a suitable promoter to achieve this is possible following the guidelines herein for selecting cells for use in the KIRA ELISA.

Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.* 255:2073 [1980]) or other glycolytic enzymes (Hess et al., *J. Adv. Enzyme Reg.*, 7:149 [1968]; and Holland, *Biochemistry* 17:4900[1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

rPTK or receptor construct transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the rPTK or receptor construct sequence, provided such promoters are compatible with the host cell systems.

The early and late promoters of the SV40 virus are conveniently obtained as an SV40 restriction fragment that also contains the SV40 viral origin of replication. Fiers et al., *Nature* 273:113 (1978); Mulligan and Berg, *Science* 209:1422–1427 (1980); Pavlakis et al., *Proc. Natl. Acad. Sci. USA* 78:7398–7402 (1981). The immediate early promoter of the human cytomegalovirus is conveniently obtained as a HindIII E restriction fragment. Greenaway et al., *Gene* 18:355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature* 295:503–508 (1982) on expressing cDNA encoding immune interferon in monkey cells; Reyes et al., *Nature* 297:598–601 (1982) on expression of human-β-interferon cDNA in mouse cells under the control of a thymidine kinase promoter from herpes simplex virus; Canaani and Berg, *Proc. Natl. Acad. Sci. USA* 79:5166–5170 (1982) on expression of the human interferon-β1 gene in cultured mouse and rabbit cells; and Gorman et al., *Proc. Natl. Acad. Sci. USA* 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Transcription of DNA encoding the rPTK or receptor construct by higher eukaryotes may be increased, if increased numbers of the rPTK or receptor construct per cell are required to facilitate detection in the ELISA stage of the assay. This may be achieved by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc. Natl. Acad. Sci. USA* 78:993 [1981]) and 3' (Lusky et al., *Mol. Cell Bio.* 3:1108 [1983]) to the transcription unit, within an intron (Banerji et al., *Cell* 33:729 [1983]), as well as within the coding sequence itself (Osborne et al., *Mol. Cell Bio.*4:1293 [1984]). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature* 297:17–18 (1982) on enhancing elements for activation of eukaryotic promoters. The enhancer may be spliced into the vector at a position 5' or 3' to the rPTK or receptor construct-encoding sequence, but is preferably located at a site 5' from the promoter.

Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the rPTK or receptor construct.

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9:309 (1981) or by the method of Maxam et al., *Methods in Enzymology* 65:499 (1980).

Other methods, vectors, and host cells suitable for adaptation to the synthesis of the rPTK or receptor construct in recombinant vertebrate cell culture are described in Gething et al., *Nature* 293:620–625 (1981); Mantei et al., *Nature*

281:40–46 (1979); Levinson et al.; EP 117,060; and EP 117,058. A particularly useful plasmid for mammalian cell culture expression of rPTK or receptor construct DNA is pRK5 (EP 307,247) or pSVI6B (PCT pub. no. WO 91/08291 published 13 Jun. 1991).

Examples of suitable eukaryotic cell lines for transformation include Saccharomyces cerevisiae, Schizosaccharomyces pombe (Beach and Nurse, Nature 290:140 [1981]; EP 139,383 published 2 May 1985); Kluyveromyces hosts (U.S. Pat. No. 4,943,529; Fleer et al., Bio/Technology 9:968–975 [1991]) and Aspergillus hosts such as A. nidulans (Ballance et al, Biochem. Biophys. Res. Commun. 112:284–289 [1983]; Tilburn et al., Gene 26:205–221 [1983]; Yelton et al., Proc. Natl. Acad. Sci. USA 81:1470–1474 [1984]) and A. niger (Kelly and Hynes, EMBO J. 4:475–479 [1985]), among lower eukaryotic host microorganisms.

Examples of useful animal host cell lines for transformation include monkey kidney CV1 line transformed by SV40 (COS-7, ATCC CRL 1651); human embryonic kidney line (293 or 293 cells subcloned for growth in suspension culture, Graham et al., J. Gen Virol. 36:59 [1977]); baby hamster kidney cells (BHK, ATCC CCL 10); Chinese hamster ovary cells/-DHFR (CHO, Urlaub and Chasin, Proc. Natl. Acad. Sci. USA 77:4216 [1980]); mouse sertoli cells (TM4, Mather, Biol. Reprod. 23:243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44–68 (19821); MRC 5 cells; FS4 cells; and a human hepatoma line (Hep G2).

Host cells are transformed with the above-described expression or cloning vectors of this invention and cultured in conventional nutrient media modified as appropriate for inducing promoters, selecting transformants, or amplifying the genes encoding the desired sequences. Transformation means introducing DNA into an organism so that the DNA is replicable, either as an extrachromosomal element or as a chromosomal integrant. Depending on the host cell used, transformation is done using standard techniques appropriate to such cells. Successful transformation is generally recognized when any indication of the operation of this vector occurs within the host cell.

For mammalian cells, the calcium phosphate precipitation method of Graham and Van der Eb, Virology 52:456–457 (1978) is preferred. General aspects of mammalian cell host system transformations have been described by Axel in U.S. Pat. No. 4,399,216 issued 16 Aug. 1983. Transformations into yeast are typically carried out according to the method of Van Solingen et al., J. Bact. 130:946 (1977) and Hsiao et al., Proc. Natl. Acad. Sci. (USA) 76:3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., Methods in Enzymology (1989), Keown et al., Methods in Enzymology 185:527–537 (1990), and Mansour et al., Nature 336:348–352 (1988).

The mammalian host cells used to produce the rPTK or receptor construct may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, Meth. Enz. 58:44 (1979), Barnes and Sato, Anal. Biochem. 102:255 (1980), U.S. Pat. No. 4,767,704; 4,657,866; 4,927,762; or 4,560,655; WO 90/03430; WO 87/00195; U.S. Pat. No. Re.30,985; or U.S. Pat. No. 5,122,469, the disclosures of each of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in Mammalian Cell Biotechnology: a Practical Approach, M. Butler, ed., IRL Press, 1991.

Gene amplification and/or expression may be measured in a sample directly, for example, by conventional Southern blotting, Northern blotting to quantitate the transcription of mRNA (Thomas, Proc. Natl. Acad. Sci. USA 77:5201–5205 [1980]), dot blotting (DNA analysis), or in situ hybridization, using an appropriately labeled probe, based on the sequences provided herein. Various labels may be employed, most commonly radioisotopes, particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining to quantitate directly the expression of gene product.

B. Selecting cells for use in the assay

As mentioned above, the cells to be subjected to the assay can be (a) cells having an endogenous receptor, (b) cells which have been transformed with a rPTK, or (c) cells transformed with a receptor construct. The suitability of the cells for use in the assay is investigated.

Cells having the endogenous rPTK can be subjected to a test-run KIRA ELISA using a known ligand to the PTK (e.g. an agonist antibody) and a control (e.g. the diluent for the agonist antibody). A range of ligand concentrations such as those used herein (see Examples 1, 2 and 3) will be used to determine whether sufficient numbers of the receptor are present in the cells being tested. In order to discover whether a cell line is unsuitable because the receptor is constitutively phosphorylated, the cell line can be subjected to the KIRA ELISA disclosed herein, wherein it is exposed to both positive and negative controls (e.g. a known agonist ligand in cell culture media as described herein as a positive control and the cell culture media without the agonist ligand as the negative control). If phosphorylation of the receptor is detected for both positive and negative controls, this may be indicative that constitutive phosphorylation of the receptor is occurring. However, it is possible that a constituent of the serum in the cell culture media is activating the receptor. Thus, the cells can be "starved" in serum-free media for about 2–12 hours (depending on cell survival and then the assay is repeated using the positive and negative controls. If activation is detected for both controls, the cell line may be considered unsuitable and another cell line can be tested.

If the cell line is transformed with the receptor (without the flag polypeptide) a strategy similar to that depicted in FIG. 4 can be used to discover whether or not the cell line is suitable for use in the assay. As a first step, successful transformation and expression of the nucleic acid encoding the rPTK is determined (see FIG. 4, step b). In order to identify whether the ECD of the rPTK is present on the surface of the cells, flow cytometric analysis can be performed using an antibody to the ECD of the receptor. The antibody can be made using the techniques for generating antibodies discussed herein. Flow cytometric analysis can be carried out using the techniques described in *Current Protocols in Immunology*, Ed. Coligen et al., Wiley publishers, Vols. 1 and 2, for example. Briefly, flow cytometric analysis involves incubating intact cells (having the receptor) with antibodies to the ECD thereof, followed by washing. The antibody-bound cells are then incubated with species specific anti-antibody antibodies conjugated to a fluorochrome. Following washing, the labeled cells are analyzed by fluorescence-activated flow cytometry to detect whether the ECD is present on the surface of the cells.

In the following step, i.e. FIG. 4, step (c), the ability of the cell-bound receptor to be activated is tested. In order to determine this, the transformed cells are exposed to a known agonist to the receptor (e.g. the endogenous ligand or an agonist antibody for the receptor). Following exposure, the cells are lysed in a suitable buffer (e.g. sodium dodecylbenzenesulfonate in phosphate buffered saline; SDS in PBS) and subjected to Western blotting with anti-phosphotyrosine antibodies as described in Wang, *Molecular and Cellular Biology* 5(12):3640–3643(1985); Glenney et a., *Journal of Immunological Methods* 109:277–285 (1988); Kamps, *Methods in Enzymology* 201:101–110 (1991); Kozma et a., *Methods in Enzymology* 201:28–43 (1 991); Holmes et at, *Science* 256:1205–10 (1992); or Corfas et al., *PNAS, USA* 90:1624–1628 (1993), for example.

Assuming the Western blotting step indicates that the rPTK can be activated, a KIRA ELISA test run can be performed, see FIG. 4 step (d), to further establish whether or not the transformed cell line can be used in the assay.

In the preferred embodiment of the invention, the KIRA ELISA is a "generic" assay insofar as any rPTK of interest can be studied regardless of the availability of receptor-specific reagents (i.e., capture agent). This embodiment employs a receptor construct having a flag polypeptide at either the amino or carboxyl terminus of the receptor.

If the flag polypeptide is provided at the $NH_2$-terminus (see, e.g., the gD.trk A, B and C receptor constructs disclosed in Example 3), the procedure for selecting a transformed cell line for use in the assay summarized in FIG. 4 can be performed. In this embodiment, the cells are transformed with the flag polypeptide-receptor construct as described earlier herein. See step (a). In step (b), successful transformation of the receptor and flag polypeptide (i.e. the receptor construct) is confirmed. In order to study this, two-dimensional flow cytometric analysis can be performed using antibodies to both the flag polypeptide and the ECD of the receptor. Techniques for two-dimensional flow cytometric analysis are disclosed in *Current Protocols in Immunology*, supra. Assuming successful transformation of the receptor construct is demonstrated, steps (c) and (d) of FIG. 4 are then performed. See the discussion above, for an explanation of steps (c) to (d) of FIG. 4.

A technique for identification of cells which have been successfully transformed with the receptor construct having a C-terminal flag polypeptide and which cells are also suitable for use in the assay is illustrated in FIG. 5. Following cell transformation [step (a)], successful transformation of the receptor is determined by flow cytometric analysis using an antibody directed against the ECD of the receptor of interest, for example. Flow cytometric analysis can be performed substantially as described above. This forms step (b) of the procedure outlined in FIG. 5.

Following step (b), successful transformation of the entire receptor construct (including the COOH-terminal flag polypeptide) is analyzed in step (c). This can be achieved by lysing the cells (using techniques for lysing cells disclosed herein) and immunoprecipitating the membrane extract with an antibody against the receptor of interest. This immunoprecipitated membrane extract is then subjected to Western blot analysis with antibodies specific for the flag polypeptide. Alternatively, rPTK-specific ELISA analysis of anti-flag polypeptide captured membrane lysate can be carried out. Briefly, this involves coating ELISA wells with appropriate flag specific capture agent. The wells are blocked, washed, and the lysate is then incubated in the wells. Unbound receptor construct is removed by washing. The wells are then reacted with receptor-specific antibody or antibodies, either directly or indirectly conjugated to HRPO. The wells are washed and the HRPO is then exposed to the chromogenic substrate (e.g., TMB).

Steps (d) and (e), i.e., detecting receptor activation and KIRA ELISA test run, are essentially the same as those steps described above.

Once useful cells are identified, they are subjected to the KIRA stage of the instantly claimed assay.

C. Coating the first solid phase with the cells

The first solid phase (e.g. a well of a first assay plate) is coated with cells having the endogenous receptor or cells which have been transformed pursuant to the preceding sections.

Preferably, an adherent cell line is chosen, so that the cells naturally adhere to the first solid phase. However, use of an adherent cell line is not essential. For example, non-adherent cells (e.g. red blood cells) can be added to round bottomed wells of an assay plate such as that sold by Becton Dickinson Labware, Lincoln Park, N.J., for example. The assay plate is then placed in a plate carrier and centrifuged so as to create a pellet of cells adhering to the base of the wells. The cell culture supernatants are removed using a pipette. Thus, use of an adherent cell is clearly advantageous over non-adherent cells since it reduces variability in the assay (i.e, the cells in the pellet of the round bottom wells may be taken up with the supernatant when the alternative method is used).

The cells to be added to the wells of the first assay plate may be maintained in tissue culture flasks and utilized when cells densities of about 70–90% confluency are achieved. Then, generally between about $1\times10^4$ to $3\times10^5$ (and preferably $5\times10^4$ to $1\times10^5$) seeded per flat-bottom well, using a pipette, for example. It has been found that, contrary to expectations, addition of cell concentrations mentioned above is sufficient to enable activation of the rPTK to be measured in the ELISA stage of the assay, without the need to concentrate or clarify the cells or cell lysate prior thereto. Often, the cells are diluted in culture medium prior to seeding them in the wells of the microtiter plate to achieve the desired cell densities.

Usually, the cells are cultured in the microtiter plates for a sufficient period of time to optimize adherence to the wells thereof, but not too long such that the cells begin to deteriorate. Thus, incubation for about 8 to 16 hours at a temperature which is the physiological optimum for the cells (usually about 37° C.) is preferred. Suitable media for culturing the cells are described in Section 1A above. Culturing in 5% $CO_2$ is recommended.

Following incubation overnight, the well supernatants are decanted and excess supernatant may be further removed by lightly tamping the microtiter plates with an absorbent substrate, e.g., a paper towel, but a sponge works equally well. Thus, a substantially homogeneous layer of adhering cells remains on the internal surfaces of the individual wells of the microtiter plate. These adhering cells are then exposed to the analyte.

D. Preparation and addition of the analyte

As mentioned above, the analyte may comprise an agonist ligand (or suspected agonist) or an antagonist (or suspected antagonist) for the rPTK of interest. The ligand may be an endogenous polypeptide, or a synthetic molecule, such as an inorganic or organic molecule. Usually, the ligand is a polypeptide. This assay is useful for screening molecules which activate (or antagonize activation) of the tyrosine kinase receptor of interest. Thus, the assay can be used for developing therapeutically effective molecules.

Where the ligand is an agonist, the molecule can comprise the native growth factor e.g., heregulin (HRG), insulin, insulin-like growth factors I and II (IGF-I and IGF-II), epidermal growth factor (EGF), interleukins (e.g., IL-8), macrophage colony-stimulating factor (M-CSF), erythropoietin (EPO), platelet-derived growth factor (PDGF), transforming growth factors alpha and beta (TGF-α and TGF-β), hepatocyte growth factor (HGF), fibroblast growth factor (FGF) and nerve growth factor (NGF). Many of these growth factors are available commercially. Alternatively, the growth factor can be made by peptide synthesis or recombinant techniques which are described herein. Synthetic small molecule agonists can similarly be generated by those skilled in the art using conventional chemical synthesis techniques.

Where the ligand is present in a biological fluid, the analyte can be prepared using techniques which are well known in the art. Body fluid such as blood or amniotic fluid may be used directly, however concentration may be required. If the analyte to be tested comprises a particular tissue, the cells thereof can be grown in cell culture and the supernatant can be tested for secreted ligand.

Often, the ligand is diluted in an aqueous diluent (such as cell culture media) so that a standard curve can be generated. However, the ligand may be present in a cell or a cell component (e.g., the cell membrane). In particular, it has been found that the assay can be used to detect the presence of a ligand in the cell membrane of a selected cell line. This is clearly useful for discovering a novel endogenous ligand for a known rPTK.

The ligand composition is added to each well which contains the adhering cells using a pipette, for example. At least one control well (e.g. to which the aqueous diluent for the ligand is added) is included in the assay.

The adhering cells are usually stimulated for a sufficient period of time to optimize the signal, but not too long such that the signal decreases as a consequence of dephosphorylation of the rPTK by endogenous phosphatases. A suitable stimulation period is between about 10 to 60 minutes, preferably about 30 minutes at a physiologically optimal temperature for the cells (usually about 37° C.).

Following activation, well supernatants are decanted and the plates can then be lightly tamped with an absorbent substrate to remove excess supernatant.

The assay can be used to detect antagonist ligands for the rPTK of interest. Antagonists generally fall into two categories (a) ones which bind to the rPTK and thereby block binding and/or activation of the rPTK by an agonist thereto (the antagonist may bind to the ECD, but this is not necessarily the case) and (b) those which bind to the agonist and thus prevent activation of the rPTK by the agonist.

In order to detect antagonist molecules from category (a) above, the cells are exposed to the suspected antagonist ligand substantially as mentioned above. Following exposure to the antagonist, the well supernatants are decanted and the plates are lightly tamped. Then, a known agonist (e.g., the endogenous growth factor) is added to the washed cells essentially as discussed in the preceding paragraphs, following which, the well supernatants are decanted and plates are lightly tamped. Alternatively, a composition comprising both the antagonist and agonist can be added to the adhering cells substantially as discussed above. Ability of the suspected antagonist to block binding and/or activation of the rPTK can subsequently be measured by ELISA as discussed below.

To detect antagonist molecules from category (b) above, a known agonist is pre-incubated with the suspected antagonist prior to the KIRA stage of the assay. This incubation is carried out for a sufficient period of time to enable a complex of the antagonist-agonist to form; from 30 min. to 12 hours, for example. This complex is then subjected to the assay with the non-complexed agonist and antagonist used as controls.

Following exposure to the agonist (and optionally the antagonist) ligand, the cells are lysed, as discussed below.

E. Solubilizing the cells

In this step of the assay, the cells are lysed so as to solubilize the rPTK such that it remains activated (i.e., the tyrosine residues remain phosphorylated) for the ELISA stage of the assay. Thus, the cells are lysed using a lysis buffer as described above which serves to solubilize the rPTK or receptor construct, yet does not dephosphorylate or denature the rPTK.

Where microtiter plates are used as mentioned above, about 75 to 200 $\mu$l of lysis buffer is added to each well. The plates can then be agitated gently using a plate shaker (e.g., such as that sold by Bellco Instruments, Vineland, N.J.) for about 1 to 2 hours. Shaking can be carried out at room temperature.

2. Enzyme-Linked Immunosorbent Assay—ELISA

The second stage of the assay involves a sandwich ELISA performed in the second assay plate. In order to carry out the ELISA, a capture agent is prepared.

A. Preparation of the capture agent

As mentioned above, the capture agent often comprises a polyclonal antibody (usually an affinity purified polyclonal antibody) or monoclonal antibody. Other capture agents are envisaged and are discussed in the definitions section above. The capture agent either binds specifically to the kinase receptor, or to the flag polypeptide (i.e. the antigen).

Polyclonal antibodies to the antigen (either the receptor or the flag polypeptide) generally are raised in animals by multiple subcutaneous (sc) or intraperitoneal (ip) injections of the antigen or an antigenic fragment thereof (often the ECD of the rPTK) and an adjuvant. It may be useful to conjugate the antigen or a fragment containing the target amino acid sequence to a protein that is immunogenic in the species to be immunized (e.g., keyhole limpet hemocyanin), using a bifunctional or derivatizing agent.

The route and schedule for administration of immunogen to the host animal or cultured antibody-producing cells therefrom are generally in keeping with established and conventional techniques for antibody stimulation and production. While mice are frequently employed as the test model, it is contemplated that any mammalian subject including human subjects or antibody-producing cells obtained therefrom can be manipulated according to the processes of this invention to serve as the basis for production of mammalian, including human, hybrid cell lines.

Animals are typically immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with ⅕ to ⅒ the original amount of conjugate in Freund's complete adjuvant (or other suitable adjuvant) by subcutaneous injection at multiple sites. 7 to 14 days later animals are bled and the serum is assayed for anti-antigen titer. Animals are boosted until the titer plateaus. Preferably, the animal is boosted with the conjugate of the same antigen, but conjugated to a different protein and/or through a different cross-linking agent. Conjugates also can be made in recombinant cell culture as protein fusions. Also, aggregating agents such as alum are used to enhance the immune response.

After immunization, monoclonal antibodies can be prepared by recovering immune cells (typically spleen cells or lymphocytes from lymph node tissue) from immunized animals and immortalizing the cells in conventional fashion, e.g., by fusion with myeloma cells or by Epstein-Barr (EB)-virus transformation and screening for clones producing the desired antibody. The hybridoma technique described originally by Kohler and Milstein, *Eur. J. Immunol.* 6:511 (1976), and also described by Hammerling et al., In: *Monoclonal Antibodies and T-Cell Hybridomas*, Elsevier, N.Y., pp. 563–681 (1981) has been widely applied to produce hybrid cell lines that secrete high levels of monoclonal antibodies against many specific antigens.

It is possible to fuse cells of one species with another. However, it is preferable that the source of the immunized antibody producing cells and the myeloma be from the same species.

The hybrid cell lines can be maintained in culture in cell culture media. The cell lines of this invention can be selected and/or maintained in a composition comprising the continuous cell line in hypoxanthine-aminopterin-thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant by conventional methods such as precipitation, ion exchange chromatography, affinity chromatography, or the like. The antibodies described herein are also recovered from hybridoma cell cultures by conventional methods for purification of IgG or IgM, as the case may be, that heretofore have been used to purify these immunoglobulins from pooled plasma, e.g., ethanol or polyethylene glycol precipitation procedures. The purified antibodies are then sterile filtered. Where the antibody is a polyclonal antibody, it is generally affinity purified using an affinity column generated from the antigen of interest so as to provide a substantially specific capture antibody. Affinity chromatography is usually preceded by other purification techniques, such as liquid chromatography.

In a further embodiment, antibodies or antibody fragments can be isolated from antibody phage libraries generated via the techniques described in McCafferty et a., *Nature*, 348:552–554 (1990), using the flag polypeptide, rPTK, or a fragment thereof, to select for a suitable antibody or antibody fragment. Clackson et al., *Nature*, 352:624–628 (1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Mark et al., *Bio/Technol.* 10:779–783 [1992]), as well as combinatorial infection and in vivo recombination as a strategy for constructing very large phage libraries (Waterhouse et al., *Nuc. Acids Res.*, 21:2265–2266 [1993]). Thus, these techniques are viable alternatives to traditional monoclonal antibody hybridoma techniques for isolation of "monoclonal" antibodies which are encompassed by the present invention.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-rPTK or anti-flag polypeptide monoclonal antibody herein. Thus, the antibody may be made by recombinant DNA methods (Cabilly et al., U.S. Pat. No. 4,816,567).

Binding of the capture agent is not affected by the presence or absence of a ligand bound to the receptor and the capture agent does not sterically block access to the phosphorylated tyrosine(s) by the anti-phosphotyrosine antibody. Furthermore, the capture agent does not, of course, activate the receptor of interest. In order to screen for an antibody having these characteristics, the procedure outlined in FIG. 3 can be carried out.

First, once the capture agent (e.g. an antibody or streptavidin) has been chosen, binding to either the receptor or the flag polypeptide (where a receptor construct is to be used in the assay) is confirmed. This can be determined by flow cytometric analysis, immunoprecipitation or antigen-coat ELISA, for example. Flow cytometric analysis has been described above. Immunoprecipitation usually involves lysing the cells (having the receptor or receptor construct) in non-ionic detergent (e.g. 0.5% Triton X-100) in a suitable buffer (e.g. PBS) and the cell lysates thus obtained are then incubated with the potential anti-receptor or anti-flag polypeptide capture agent. The immune complexes are precipitated with either (a) anti-capture agent antibodies in the presence of polyethylene glycol (PEG) which enhances precipitation of the immune complex or with (b) insoluble (e.g. agarose bound) protein A or protein G. The immunoprecipitated material is then analyzed by polyacrylamide gel electrophoresis (PAGE). For antigen-coat ELISA, ELISA wells are coated overnight with either the purified receptor, purified flag polypeptide or purified receptor construct. The coated wells are then exposed to the potential capture agent and screened with HRPO-conjugated species specific anti-capture agent antibody.

The ability of the capture agent to bind to the receptor or flag polypeptide in the presence of a ligand to the receptor is also confirmed. This can be analyzed by incubating the receptor or receptor construct with a known ligand for the receptor (e.g. the endogenous growth factor or an agonist antibody thereto). Flow cytometric analysis, immunoprecipitation or antigen-coat ELISA can then be performed substantially as described above to investigate binding of the capture agent.

Assuming the capture agent is suitable as determined by the preceding two steps, it is then shown that the capture agent does not induce receptor activation (i.e. autophosphorylation) either before or after cell lysis. Thus, the cell-bound receptor or receptor construct is exposed to either the potential capture agent or a negative control (e.g. a control antibody which does not activate the receptor). Following cell lysis, the receptor or receptor construct can be subjected to Western blot analysis using labeled anti-phosphotyrosine antibodies. See, e.g., Glenney et al, *Journal of Immunological Methods* 109:277–285 (1988); Kamps, *Methods in Enzymology* 201:101–110(1991);Kozma et al., *Methods in Enzymology* 201:28–43 (1991); or Holmes et al., *Science* 256:1205–10 (1992). To establish whether the capture agent induces receptor activation following cell lysis, a trial run of the KIRA ELISA (with both the capture agent and a negative control as discussed above) can be performed.

Finally, the ability of an anti-phosphotyrosine antibody (e.g. biotinylated anti-phosphotyrosine antibody) to bind the activated receptor in the presence of the potential capture agent is confirmed by a trial run in the KIRA ELISA disclosed herein.

Assuming the capture agent meets all the criteria specified above, it has good potential for use in the KIRA ELISA.

Once a suitable capture agent has been prepared, the second solid phase is coated therewith. Between about 0.1 to 10 µg/ml of capture agent can be added to each well of the second assay plate using a pipette, for example. The capture agent is often provided in a buffer at a high pH (e.g., between about 7.5 to 9.6) so that it has an increased overall charge and therefore displays enhanced binding to the second assay plate. Usually, the capture agent will be incubated in the wells for between about 8 to 72 hours to enable a sufficient coating of the capture agent to form on the inside walls of the wells. This incubation is generally carried out at low temperatures (e.g., between about 3°–8° C.) to avoid or reduce degradation of the capture agent.

Following incubation, the wells of the plate are decanted and tamped lightly with an absorbent substrate. Non-specific binding is then blocked. In order to achieve this, a block buffer, is added to the wells. For example, a block buffer containing bovine serum albumin (BSA) such as that sold by Intergen Company, Purchase, N.Y., is suitable. It has been found that addition of between about 100 to 200 µl of block buffer to each well followed by gentle agitation at room temperature for between about 1–2 hours is sufficient to block non-specific binding. It is also possible to add the block buffer directly to the cell lysate obtained in the previous step rather than to the second assay plate.

Following this, the capture agent-coated plates are washed several times (usually between about 3–8 times) with a wash buffer. The wash buffer can comprise phosphate buffered saline (PBS) at pH 7.0 to 7.5, for example. However, other wash buffers are available which can also be used. Conveniently, an automated plate washer, such as the ScanWasher 300 (Skatron Instruments, Inc., Sterling, Va.) can be used for this, and other, washing steps of the assay.

B. Measuring tyrosine phosphorylation

The activated, solubilized rPTK (or receptor construct) is then added to the wells having the capture agent adhering thereto. As a general proposition, about 80% of cell lysate obtained as mentioned under Section 1E above can be added to each well (i.e., about 60 to 160 µl depending on the original volume of the wells). The lysate is incubated with the capture agent for an adequate period of time to enable the rPTK to be captured in the wells, e.g., from 1 to 3 hours. Incubation can be carried out at room temperature.

Unbound cell lysate is then removed by washing with wash buffer. Following this washing step, an amount of the anti-phosphotyrosine antibody which is equal to, or less than, the amount of block buffer added previously, is added to each well. For example, about 50 to 200 µl of an anti-phosphotyrosine antibody preparation having between about 0.3 to 0.5 µg/ml of antibody in a suitable buffer (e.g., PBS with a detergent such as those included in the lysis buffer) is added to the well. This is followed by a washing step to remove unbound anti-phosphotyrosine antibody.

Tyrosine phosphorylation is then quantified by the amount of anti-phosphotyrosine antibody binding to the second solid phase. Many systems for detecting the presence of an antibody are available to those skilled in the art. Some examples follow.

Generally, the anti-phosphotyrosine antibody will be labelled either directly or indirectly with a detectable label. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, supra, for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter (Dynatech).

(c) Various enzyme-substrate labels are available and U.S. Pat. No. 4,275,149 provides a review of some of these. The enzyme generally catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a Dynatech ML3000 chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.*(ed J. Langone & H. Van Vunakis), Academic press, New York, 73:147–166 (1981) and *Current Protocols in Immunology*, supra.

Examples of enzyme-substrate combinations include, for example:

(i) Horseradish peroxidase (HRPO) with hydrogen peroxidase as a substrate, wherein the hydrogen peroxidase oxidizes a dye precursor (e.g. orthophenylene diamine [OPD] or 3,3',5,5'-tetramethyl benzidine hydrochloride [TMB]).

(ii) alkaline phosphatase (AP) with para-Nitrophenyl phosphate as chromogenic substrate.

(iii) β-D-galactosidase (β-D-Gal) with a chromogenic substrate (e.g. p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. See, *Current Protocols in Immunology*, supra, for a review of techniques involving biotin-avidin conjugation. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

In another embodiment of the invention, the anti-phosphotyrosine antibody need not be labeled, and the presence thereof can be detected using a labeled anti-antiphosphotyrosine antibody (e.g. anti-mouse anti-phosphotyrosine antibody conjugated with HRPO).

In the preferred embodiment, the anti-phosphotyrosine antibody is labeled with an enzymatic label which catalyzes a color change of a substrate (such as tetramethyl benzimidine [TMB], or orthaphenylene diamine [OPD]). Thus, the use of radioactive materials is avoided. A color change of the reagent can be determined spectrophotometrically at a suitable wavelength (e.g. 450 nm for TMB and 490 nm for OPD, with a reference wavelength of 650 nm).

3. Kits

As a matter of convenience, the reagents can be provided in a kit, i.e., a packaged combination of reagents, for combination with the analyte in assaying the ability of the analyte to activate or prevent activation of a rPTK of interest. The components of the kit will be provided in predetermined ratios. Thus, a kit will comprise the specific second solid phase for the assay as well as the anti-flag polypeptide capture agent either packaged separately or captured to the second solid phase (e.g. a microtiter plate). Usually, other reagents, such as the anti-phosphotyrosine antibody labelled directly or indirectly with an enzymatic label will also be provided in the kit. Where the detectable label is an enzyme, the kit will include substrates and cofactors required by the enzyme (e.g. a substrate precursor which provides the detectable chromophore or fluorophore). In addition, other additives may be included such as stabilizers, buffers (e.g. a block buffer and a lysis buffer) and the like. Conveniently, the kit can also supply the homogeneous population of cells which have been transformed with the receptor construct. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration. The kit also suitably includes instructions for carrying out the KIRA ELISA.

4. Uses for the Assay

This application provides two assays which are useful for reliable, sensitive and quantitative detection of kinase activation. The first assay can be used where a kinase receptor-specific capture antibody having the desired characteristics herein described is available or has been prepared. The second assay is a generic assay which enables activation of any kinase receptor to be measured via the use of a flag polypeptide and a capture agent which binds specificity thereto.

These assays are useful for identifying novel agonists/antagonists for a selected kinase receptor. Also, the assay provides a means for studying ligand-receptor interactions (i.e., mechanism studies). Also the presence of an endogenous receptor in a selected cell line can be quantified using the assay. The assays are further useful for identifying the presence of a ligand for a selected kinase receptor in a biological sample and, e.g., establishing whether a growth factor has been isolated following a purification procedure. It is desirable to have an assay for measuring the ability of these growth factors to activate their respective receptors.

The assay also has clinical applications for detecting the presence of a ligand for a selected rPTK (e.g. the insulin receptor) in a biological sample taken from a human and thus patients having elevated or depressed levels of the ligand can be identified. This is particularly desirable where elevated or depressed levels of the ligand cause a pathological condition. Accordingly, candidates for administration of the selected ligand (e.g. insulin) can be identified through this diagnostic method. It is possible, using the assay disclosed herein, to assay the pK of agonists or antagonists administered to a patient. This assay also facilitates the detection of shed receptor in a biological sample.

Below are examples of specific embodiments for carrying out the present invention. The examples are offered for illustrative purposes only, and are not intended to limit the scope of the present invention in any way.

All publications, patents and patent applications cited herein, whether supra or infra, are hereby incorporated by reference in their entirety.

EXAMPLE 1

KIRA ELISA of the HER2 Receptor

The assay system described in this example was developed to measure the extent of autophosphorylation as a result of the interactions between the HER2 receptor and its specific activator, heregulin (HRG). The overexpression of p185$^{HER2}$ has been correlated with poor clinical outcome in a number of epithelia-derived cancers. Heregulin and its rodent homologue, neu differentiation factor (NDF), were originally purified based on their ability to stimulate the autophosphorylation of a 185 kDa protein in the breast carcinoma cell lines MCF-7 and MDA-453, respectively. In this embodiment of the invention, the cell line expressing the tyrosine kinase receptor DNA (either endogenous or transformed) is adhere(e.g. there is an antibody (e.g. monoclonal or affinity purified polyclonal) capable of specifically binding the receptor such that it neither stimulates autophosphorylation in the absence of ligand nor suffers impaired binding due to the presence of bound ligand. Standard curve preparations and many samples may easily be run simultaneously in replicate and at several dilutions using this assay, readily allowing quantitation of ligand activity in a large number of unknown samples.

(i) Capture agent preparation

Polyclonal anti-HER2 antibody was isolated from pooled immune sera from New Zealand White rabbits immunized with the extracellular domain of the HER2 molecule (Fendly et al., *Journal of Biological Response Modifiers* 9:449–455 [1990]). The rHER2 ECD specific antibodies were affinity purified using an FPLC (Pharmacia Biotech, Inc, Piscataway, N.J.) with an affinity column generated from rHER2 ECD conjugated to Avidgel F (Bioprobe International, Inc, Tustin, Calif.). The resulting purified antibody stock was 0.829 mg/ml in phosphate buffered saline (PBS), pH 7.4, and was stored as 0.5 ml aliquots at −20° C.

(ii) Anti-phosphotyrosine antibody preparation

Monoclonal anti-phosphotyrosine, clone 4G10, was purchased from Upstate Biologicals, Inc (UBI, Lake Placid, N.Y.) and biotinylated using long-arm biotin-N-hydroxysuccinamide (Biotin-X-NHS, Research Organics, Cleveland, Ohio).

(iii) Ligand

The recombinant truncated form of β1heregulin (MW=7.88 Kd) corresponding to residues 177–244 (HRGβ1$_{177-244}$) was produced in *E. coli* and purified to homogeneity as described in Holmes et al., *Science*, 256: 1205–1210(1992) and was stored at 4° C. as an 89.7 μM stock solution in 50 mM Tris/HCl, pH 7.5.

(iv) Adherent Cells

MCF-7 (ATCC-HTB 22), an adherent cell line isolated from a human breast adenocarcinoma, was obtained from American Type Culture Collection (ATCC, Rockville, Md.). MCF-7 cells have been shown to produce measurable levels of surface p185$^{HER2}$ by both FACS and ELISA analysis. The cells were maintained in 150 cm$^2$ tissue culture flasks (Corning Inc, Corning, N.Y.) and utilized when at cell densities of 60% to 75% confluency. For the assay, 2×10$^5$ cells were seeded per well in flat-bottom microtiter plates (Falcon 3072, Becton Dickinson Labware, Lincoln Park, N.J.) cultured overnight at 37° C. in 5% CO$_2$. Cells were grown in F12/DMEM 50:50 Gibco as a custom formulation (Gibco/BRL, Life Technologies, Grand Island, N.Y.). The medium was supplemented with 10% FBS (HyClone, Logan, Utah), 25 mM HEPES (Gibco) and 2 mM L-glutamine (Gibco).

(v) KIRA ELISA

MCF-7 cells (2×10$^5$) in 100 μl media were added to each well in a flat-bottom-96 well culture plate and cultured overnight at 37° C. in 5% CO$_2$. The following morning the well supernatants were decanted, and the plates were lightly tamped on a paper towel. 50 μl of media containing either experimental samples or the recombinant HRGβ1$_{177-244}$ standards (3000, 1000, 333, 111, 37, 12, 4, and 0 pM) was then added to each well. The cells were stimulated at 37° C. for 30 min., the well supernatants were decanted, and the plates were once again lightly tamped on a paper towel. To lyse the cells and solubilize the receptors, 100 μl of lysis buffer was added to each well. Lysis buffer consisted of 150 mM NaCl containing 50 mM HEPES (Gibco), 0.5% Triton-X 100 (Gibco), 0.01% thimerosal, 30 KIU/ml aprotinin (ICN Biochemicals, Aurora, Ohio), 1 mM 4-(2-aminoethyl)-benzenesulfonylfluoride hydrochloride (AEBSF; ICN Biochemicals), 50 μM leupeptin (ICN Biochemicals), and 2 mM sodium orthovanadate (Na$_3$VO$_4$, Sigma Chemical Co, St. Louis, Mo.), pH 7.5. The plate was then agitated gently on a plate shaker (Bellco Instruments, Vineland, N.J.) for 60 min. at room temperature.

While the cells were being solubilized, an ELISA microtiter plate (Nunc Maxisorp, Inter Med, Denmark) coated overnight at 4° C. with the affinity-purified polyclonal anti-HER2 ECD (1.0 μg/ml in 50 mM carbonate buffer, pH 9.6, 100 μl/well) was decanted, tamped on a paper towel and blocked with 150 μl/well of Block Buffer [PBS containing 0.5% BSA (Intergen Company, Purchase, N.Y.) and 0.01% thimerosal] for 60 min. at room temperature with gentle agitation. After 60 minutes, the anti-HER2 ECD coated plate was washed 6 times with wash buffer (PBS containing 0.05% Tween-20 and 0.01% thimerosal) using an automated plate washer (ScanWasher 300, Skatron Instruments, Inc, Sterling, Va.).

The lysate containing solubilized p185$^{HER2}$ from the cell-culture microtiter well was transferred (85 μl/well) to anti-rHER2 ECD coated and blocked ELISA well and was incubated for 2 h at room temperature with gentle agitation. The unbound receptor was removed by washing with wash buffer and 100 μl of biotinylated 4G 10 (anti-phosphotyrosine) diluted 1:2000 in dilution buffer (PBS containing 0.5% BSA, 0.05% Tween-20, 5 mM EDTA, and 0.01% thimerosal), i.e. 400 pg/ml, was added to each well. After incubation for 2 h at room temperature the plate was washed and 100 μl of HRPO-conjugated streptavidin (Zymed Laboratories, S. San Francisco, Calif.) diluted 1:10000 in dilution buffer was added to each well. The plate was incubated for 30 minutes at room temperature with gentle agitation. The free avidin-conjugate was washed away and 100 μl freshly prepared substrate solution (tetramethyl benzidine [TMB]; 2-component substrate kit; Kirkegaard and Perry, Gaithersburg, Md.) was added to each well. The reaction was allowed to proceed for 10 minutes, after which the color development was stopped by the addition of 100 μl/well 1.0M H$_3$P$_4$. The absorbance at 450 nm was read with a reference wavelength of 650 nm (ABS$_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

The standard curve shown in FIG. 7 was generated by stimulating MCF-7 cells with 3000, 1000, 333, 111, 37, 12, 4, or 0 pM HRGβ1$_{177-244}$ and presented as pM HRGβ1$_{177-244}$ vs. mean ABS$_{450/650}$±sd using the DeltaSoft program. Sample concentrations were obtained by interpolation of their absorbance on the standard curve and are expressed in terms of pM HRGβ1$_{177-244}$ activity.

When the data were fitted to a 4-parameter nonlinear least squares equation, they resulted in a correlation coefficient of 0.9998. For the data shown in FIG. 7, the $EC_{50}$ of receptor activation by $HRG\beta1_{177-244}$ was 373 pM. To demonstrate the highly reproducible nature of the $p185^{HER2}$ KIRA ELISA, seven standard curves were generated over the period of one month and the $EC_{50}$'s are averaged. This gives an $EC_{50}$ave for $HRG\beta1_{177-244}$ of 360±40 pM (average±SD).

(vi) Intra- and inter-assay precision and assay specificity

The intra-assay variability was determined by performing the $p185^{HER2}$ KIRA ELISA on three separate days. For each test, the standard curve is run in triplicate. Controls with $HRG\beta1_{177-244}$ corresponding to high (1000 pM), mid (200 pM) and low (40 pM) were assayed in 24 replicates. The $ABS_{450/650}$ of the individual test samples were converted to pM $HRG\beta1_{177-244}$ activity and the 24 converted values for each test concentration were averaged. The data are expressed as averaged value and % coefficient of variation (% cv; [(intra-assay standard deviation/intra-assay averaged calculated value)×100]. See Table 1A below.

TABLE 1

Intra- and Inter-assay Variation

A. Intra-assay Precision (n-24 per test)

| | High Value[a] | | Mid Value | | Low Value | |
|---|---|---|---|---|---|---|
| | Average Value (pM) | % cv[b] | Average Value (pM) | % cv | Average Value (pM) | % cv |
| Test #1 | 1256 | 19.5% | 209 | 10.8% | 33 | 12.3% |
| Test #2 | 1078 | 10.0% | 196 | 5.1% | 38 | 7.5% |
| Test #3 | 999 | 14.3% | 196 | 6.3% | 35 | 11.3% |

B. Inter-assay Precision (n = 3)

| Average Value (pM) | % cv[c] | Average Value (pM) | % cv | Average Value (pM) | % cv |
|---|---|---|---|---|---|
| 1100 | 4.3% | 200 | 6.3% | 34 | 9.0% |

[a]Expected high value: 1000 pM; mid value: 200 pM; low value: 40 pM
[b]Intra-assay % cv determined as intra-assay sd/intra-assay average × 100
[c]Inter-assay % cv determined as inter-assay sd/inter-assay average × 100

The intra-assay variability of the KIRA ELISA was within acceptable limits despite the fact that the assay actually consists of both bioassay and ELISA components. The coefficients of variance (%) for the highest values were under 20% and for the mid and low values were at or under 10%.

The inter-assay variability was determined by averaging the values from upper-most three adjacent wells (of the 24 wells run) for a given sample concentration from each run. The three separate averages for each test concentration were then averaged. The data were expressed as averaged value and % cv [(inter-assay standard deviation/inter-assay averaged value)×100]. See Table 1B. above. The inter-assay variability of the KIRA ELISA was within acceptable limits.

In order to confirm the specificity of the assay, MCF-7 cells were stimulated with either $HRG\beta1_{177-244}$ at 3000, 1000, 333, 111, 37, 12, 4 or 0 pM or insulin-like growth factor-1 (IGF-1), epidermal growth factor (EGF), vascular endothelial growth factor (VEGF), or insulin at 30000, 10000, 3333, 1111, 370, 120, 40 or 0 pM. The $p185^{HER2}$ KIRA ELISA was then performed as described above. The results are depicted in FIG. 8.

The $p185^{HER2}$ KIRA ELISA was clearly specific for heregulin. While $HRG\beta1_{177-244}$ induced normal receptor stimulation and autophosphorylation, the closely related EGF gives only a slight stimulation ($OD_{450/650}$=0.239) at the highest concentration tested (100 nM). Since EGF-R is produced in MCF-7 cells, this signal is likely due to EGF receptor transphosphorylation of $p185^{HER2}$. Neither insulin-like growth factor-1 (IGF-1), vascular endothelial growth factor (VEGF) nor insulin have any detectable effect on the MCF-7 $p185^{HER2}$ KIRA ELISA, the latter despite the fact that MCF-7 cells produce active insulin receptors.

The results presented in this example demonstrate that the KIRA ELISA is a useful method for assaying ligand activation of a kinase receptor, e.g., heregulin activation of the $p185^{HER2}$ receptor. Levels of receptor activation in terms of tyrosine phosphorylation are easily quantified and an $EC_{50}$ for a given ligand is readily determined. One potential use for this assay would be to screen compounds for receptor agonist or antagonist activities. The potential throughput for this assay greatly surpasses that of Western blot analysis. Since the cell-culture portion of the assay is conducted in 96-well plates, many samples may be run in replicate at different dilutions at one time in a one-day assay.

EXAMPLE 2

KIRA ELISA of the Rse Receptor

Mark et al., *Journal of Biological Chemistry* 269(14): 10720–10728 (1994) describe isolation of the Rse receptor protein tyrosine kinase from human and murine tissues. This Rse receptor with a carboxyl-terminal flag polypeptide (i.e. Rse.gD) was subjected to the KIRA ELISA described herein. The experimental procedure is outlined below.

(i) Capture agent preparation

Monoclonal anti-gD (clone 5B6) was produced against a peptide from Herpes simples virus glycoprotein D (Paborsky et al, *Protein Engineering* 3(6):547–553 [1990]). The purified stock preparation was adjusted to 3.0 mg/ml in phosphate buffered saline (PBS), pH 7.4 and 1.0 ml aliquots were stored at −20° C.

(ii) Anti-phosphotyrosine antibody preparation

Monoclonal anti-phosphotyrosine, clone 4G10, was purchased from Upstate Biologicals, Inc (UBI, Lake Placid, N.Y.) and biotinylated using long-arm biotin-N-hydroxysuccinamide (Biotin-X-NHS, Research Organics, Cleveland, Ohio).

(iii) Ligand

Since the endogenous ligand for the Rse receptor was not available, an agonist antibody for the Rse receptor was prepared which forms the ligand for the KIRA ELISA described in this Example. To generate the agonist antibody, a Rse.IgG chimera was generated. Briefly, the coding sequence of the ECD of Rse was fused to that of the human IgG-γ1 heavy chain in a multi-step process. PCR was used to generate a fragment with a unique BstEII site 3' to the coding sequences of the Rse amino acid 428. The PCR product was joined to the human IgG-$\gamma_1$ heavy chain cDNA through a unique BstEII site in that construct (Mark et al., *J. Cell. Biol.*, 267:26166–26171 [1992]). The resulting construct (termed pRK.bpTK3.IgG.fusion) contained the coding sequences for amino acids 375–428 of Rse joined to those encoding human IgG-$\gamma_1$ heavy chain. The remaining portion of the Rse ECD (amino acids 1–374) was then added by linkage through the Bam HI site in pRK.bpTK3.IgG.fusion to yield pRK.Rse.IgG.

To generate stable cell populations expressing Rse.IgG, the cDNA encoding Rse.IgG was subcloned into the episomal CMV-driven expression plasmid pCIS.EBON, a pRK5 derivative disclosed in Cachianes et al., *Bio. Techniques*, 15:225–259 (1993). Human fetal kidney 293 cells (obtained from ATCC, 12301 Parklawn Drive, Rockville, Md., USA) were transfected by the calcium phosphate technique. Cell monolayers were incubated for four hours in the presence of the DNA precipitate, glycerol shocked, and cultured in F12:DMEM (1:1) containing 2 mM glutamine, 10% fetal bovine serum, penicillin and streptomycin. After 48 hours, populations were replated in media containing G418to select for a stable population of cells. Conditioned media was collected from cells expressing Rse.IgG nucleic acid that have been cultured in serum-free media for 72 hours in the absence of G418.

Rse.IgG was purified by affinity chromatography on a protein A column using procedures as described by Chamow, S. M., et at, *Biochemistry*, 29:9885–9891 (1990) with the following minor modifications. Conditioned media collected from cells expressing the Rse.IgG was adjusted to 0.1M citrate pH 6.0 and loaded directly onto a protein A column (Repligen). The column was washed with 0.1M citrate, pH 6.0, and was eluted with 3M $MgCl_2$ with 10% glycerol. Fractions were pooled and concentrated a PD-10 column, dialyzed and concentrated against PBS. Protein concentrations were determined by an ELISA against human IgG (Fc). The protein was analyzed for purity by Coomassie staining of PAGE gels.

Polyclonal antibodies were generated in New Zealand white rabbits against the Rse.IgG formed as described above. 4 μg of Rse.IgG in 100 μl PBS was emulsified with 100 μl Freund's adjuvant (complete adjuvant for the primary injection and incomplete adjuvant for all boosts). For the primary immunization and the first boost, the protein was injected directly into the popliteal lymph nodes (Sigel et al., *Methods Enzymol.*, 93, 3–12 [1983]). For subsequent boosts, the protein was injected into subcutaneous and intramuscular sites. 1.3 μg protein/kg body weight was injected every 3 weeks with bleeds taken and 2 weeks following each boost. The polyclonal antisera generated was then precipitated in 50% ammonium sulphate.

The resultant, purified polyclonal antisera is called "19B" herein. To confirm the ability of the 19B antisera to induce autophosphorylation of the Rse receptor, serum starved 3T3.gD.R11 cells (transformed with nucleic acid encoding the Rse receptor with an amino terminal gD flag polypeptide [i.e. gD.Rse] using the techniques described in Mark et al., *Journal of Biological Chemistry* 269(14):10720–10728 [1994]) or NIH3T3 cells were exposed to pre-immune serum or 19B polyclonal antisera at a 1:200 dilution for 10 minutes. The gD.Rse protein was immunoprecipitated from extracts using the anti-gD monoclonal antibody 5B6. Proteins were fractionated on 7% SDS-PAGE under reducing conditions and transferred to nitrocellulose. Phosphorylation of Rse was detected with labelled anti-phosphotyrosine antibody. Treatment of the 3T3.gD.R 11 cells with 19B antisera stimulated the phosphorylation of the 140 kD gD.Rse protein. This increase was not observed in cells treated with pre-immune sera.

The purified 19B polyclonal antisera was stored at 4° C. as an 2.8 mg/ml stock solution in PBS, pH 7.5.

(iv) Preparation of Rse.gD nucleic acid

Synthetic double stranded oligonucleotides were used to reconstitute the coding sequence for the C-terminal 10 amino acids (880–890) of human Rse and add an additional 21 amino acids containing an epitope for the antibody 5B6 and a stop codon. The final sequence of the synthetic portion of the fusion gene was: coding strand:
5'-TGCAGCAAGGGCTACTGCCACACTCGAGCTGC-
G C A G AT G C TA G C C T C A A G AT G G C T G
ATCCAAATCGATTCCGCGGCAAAGATCTTCCGG-
TCCTGTAGAAGCT-3' (SEQ ID NO: 10) noncoding (anti-sense) strand:
5'-AGCTTCTACAGGACCGGAAGATCTTTGCCGC-
G G A AT C G AT T T G G AT C A G C C AT C T T G
AGGCTAGCATCTGCGCAGCTCGAGTGTGGCAGT-
AGCCCTTGCTGCA-3' (SEQ ID NO: 11).

The synthetic DNA was ligated with the cDNA encoding amino acids 1–880 of human Rse at the PstI site beginning at nucleotide 2644 of the published human Rse cDNA sequence (Mark et al, *Journal of Biological Chemistry* 269(14):10720–10728 [1994]) and HindIII sites in the polylinker of the expression vector pSVI7.ID.LL (See FIG. 16; SEQ ID NO: 9) to create the expression plasmid pSV.ID.Rse.gD. Briefly, the expression plasmid comprises a dicistronic primary transcript which contains sequence encoding DHFR bounded by 5' splice donor and 3' splice acceptor intron splice sites, followed by sequence that encodes the Rse.gD. The full length (non-spliced) message contains DHFR as the first open reading frame and therefore generates DHFR protein to allow selection of stable transformants.

(v) Cell transformation dp12.CHO cells (EP 307,247 published 15 Mar. 1989) were electroporated with 20 μgs of pSV.ID.Rse.gD which had been linearized at a unique NotI site in the plasmid backbone. The DNA was ethanol precipitated after phenol/chloroform extraction and was resuspended in 20 μl 1/10 Tris EDTA. Then, 10 μg of DNA was incubated with $10^7$ CHO.dp12 cells in 1 ml of PBS on ice for 10 min. before electroporation at 400 volts and 330 μf. Cells were returned to ice for 10 min. before being plated into non-selective medium. After 24 hours cells were fed nucleoside-free medium to select for stable DHFR+clones.

(vi) Selection of transformed cells for use in the KIRA ELISA

To identify a cell line that expresses Rse.gD nucleic acid, candidate clones were screened by fluorescence activated cell sorting (FACS) analysis using the polyclonal antiserum 19B generated as described above, which recognizes epitopes in the extracellular domain of Rse. See FIG. 5, step (b).

To confirm that clones that scored positive in the FACS assay express full-length Rse.gD nucleic acid, cell lysates were prepared (Lokker et al., *EMBO J*, 11:2503–2510 [1992]) and solubilized Rse.gD was immunoprecipitated with the 19B antisera. The immunoprecipitated proteins were fractionated under reducing conditions using 7% PAGE, blotted onto nitrocellulose and then probed with the anti-gD 5B6 antibody which was detected with a horseradish peroxidase conjugated anti-mouse IgG antibody. See FIG. 5, step (c). The ability of Rse.gD in cell clones to be activated to undergo autophosphorylation in response to the 19B agonistic antibody was determined. Briefly, serum starved dp.CHO cells transformed with Rse.gD nucleic acid as described above were exposed to pre-immune or 19B antisera at a 1:200 dilution for 10 min. The Rse.gD protein was immunoprecipitated from extracts using the anti-gD 5B6 monoclonal antibody. Proteins were fractionated on 7% SDS-PAGE under reducing conditions and transferred to nitrocellulose. Phosphorylation of Rse was detected with labelled antiphosphotyrosine antibody. See FIG. 5, step (d).

(vii) Media

Cells were grown in F12/DMEM 50:50 (Gibco/BRL, Life Technologies, Grand Island, N.Y.). The media was supplemented with 10% diafiltered FBS (HyClone, Logan, Utah), 25 mM HEPES and 2 mM L-glutamine.

(viii) KIRA ELISA

Rse.gD transformed dpi2.CHO cells (EP 307,247 published 15 Mar. 1989) were seeded ($5 \times 10^4$ per well) in the wells of a flat-bottom-96 well culture plate in 100 μl media and cultured overnight at 37° C. in 5% $CO_2$. The following morning the well supernatants were decanted, and the plates were lightly tamped on a paper towel. 100 μl of media containing either experimental samples or 1:100, 1:200, 1:400, 1:800, 1:1600, 1:3200 or 0 diluted, anti-Rse agonist polyclonal antibody (19B pAb) was then added to each well. The cells were stimulated at 37° C. for 30 min., the well supernatants were decanted, and the plates were once again lightly tamped on a paper towel. To lyse the cells and solubilize the receptors, 100 μl of lysis buffer was added to each well. Lysis buffer consisted of 150 mM NaCl containing 50 mM HEPES (Gibco), 0.5% Triton-X 100 (Gibco), 0.01% thimerosal, 30 KIU/ml aprotinin (ICN Biochemicals, Aurora, Ohio), 1 mM 4-(2-aminoethyl)-benzenesulfonyl fluoride hydrochloride (AEBSF; ICN Biochemicals), 50 μM leupeptin (ICN Biochemicals), and 2 mM sodium orthovanadate ($Na_3VO_4$; Sigma Chemical Co, St. Louis, Mo.), pH 7.5. The plate was then agitated gently on a plate shaker (Bellco Instruments, Vineland, N.J.) for 60 min. at room temperature.

While the cells were being solubilized, an ELISA microtiter plate (Nunc Maxisorp, Inter Med, Denmark) coated overnight at 4° C. with the 5B6 monoclonal anti-gD antibody (0.5 μg/ml in 50 mM carbonate buffer, pH 9.6, 100 μl/well) was decanted, tamped on a paper towel and blocked with 150 μl/well of Block Buffer [PBS containing 0.5% BSA (Intergen Company, Purchase, N.Y.) and 0.01% thimerosal] for 60 min. at room temperature with gentle agitation. After 60 minutes, the anti-gD 5B6 coated plate was washed 6 times with wash buffer (PBS containing 0.05% Tween-20 and 0.01% thimerosal) using an automated plate washer (ScanWasher 300, Skatron Instruments, Inc, Sterling, Va.).

The lysate containing solubilized Rse.gD from the cell-culture microtiter well was transferred (85 μl/well) to anti-gD 5B6 coated and blocked ELISA well and was incubated for 2 h at room temperature with gentle agitation. The unbound Rse.gD was removed by washing with wash buffer and 100 μl of biotinylated 4G10 (anti-phosphotyrosine) diluted 1:2000 in dilution buffer (PBS containing 0.5% BSA, 0.05% Tween-20, 5 mM EDTA, and 0.01% thimerosal), i.e. 400 pg/ml was added to each well. After incubation for 2 h at room temperature the plate was washed and 100 μl of HRPO-conjugated streptavidin (Zymed Laboratories, S. San Francisco, Calif.) diluted 1:10000in dilution buffer was added to each well. The plate was incubated for 30 minutes at room temperature with gentle agitation. The free avidin-conjugate was washed away and 100 μl freshly prepared substrate solution (tetramethyl benzidine [TMB]; 2-component substrate kit; Kirkegaard and Perry, Gaithersburg, Md.) was added to each well. The reaction was allowed to proceed for 10 minutes, after which the color development was stopped by the addition of 100 μl/well 1.0M $H_3P_4$. The absorbance at 450 nm was read with a reference wavelength of 650 nm ($ABS_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

The standard curve shown in FIG. 10 was generated by stimulating Rse.gD transformed CHO cells with 1:100, 1:200, 1:400, 1:800, 1:1600, 1:3200 or 0 diluted, anti-Rse agonist antibody (19B) and presented as 1/dilution anti-Rse agonist antibody (19B) vs. mean $ABS_{450/650}$±sd using the DeltaSoft program.

The results presented in this example demonstrate that the KIRA ELISA is a useful method for assaying ligand activation of a receptor construct having a carboxyl terminal flag polypeptide, e.g., activation of Rse.gD. Levels of receptor activation in terms of tyrosine phosphorylation are easily quantified and an $EC_{50}$ for a given ligand (e.g. an agonist antibody for the receptor) is readily determined.

EXAMPLE 3

KIRA ELISA of the trk A, B and C Receptors

Neurotrophins belong to a family of small, basic proteins which play a crucial role in the development and maintenance of the nervous system. The first identified and probably best understood member of this family is nerve growth factor (NGF). See U.S. Pat. No. 5,169,762, issued Dec. 8, 1992. Recently, sequentially related but distinct polypeptides with similar functions to NGF have been identified. For example, brain-derived neurotrophic factor (BDNF), now also referred to as neurotrophin-2 (NT2), was cloned and sequenced by Leibrock et al. (*Nature*, 341:149–152 [1989]). Several groups identified a neurotrophic factor originally called neuronal factor (NF), and now referred to as neurotrophin-3 (NT3). (Ernfors et al., *Proc. Natl. Acad. Sci. USA*, 87: 5454–5458 [1990]; Höhn et al., *Nature*, 344:339 [1990]; Maisonpierre et al., *Science*, 247:1446 [1990]; Rosenthal et al., *Neuron*, 4:767 [1990]; Jones and Reichardt, *Proc. Natl. Acad. Sci. USA*, 87:8060–8064 [1990]; Kaisho et al., *FEBS Lett.*, 266:187 [1990]). Neurotrophins-4 and -5 (NT4 and NT5) have been recently added to the family (Hallbook et al., *Neuron*, 6: 845–858 [1991]; Berkmeier et al., *Neuron*, 7: 857–866 [1991]; Ip et al., *Proc. Natl. Acad. Sci. USA*, 89:3060–3064 [1992]).

Neurotrophins, similarly to other polypeptide growth factors, affect their target cells through interactions with cell surface rPTKs (called Trk receptors). The first member of the trk receptor family, trkA, was initially identified as the result of an oncogenic transformation caused by the translocation of tropomyosin sequences onto its catalytic domain. Later work identified trkA as a signal transducing receptor for NGF. Subsequently, two other related receptors, mouse and rat trkB (Klein et al., *EMBO J.*, 8: 3701–3709 [1989]; Middlemas et al., *Mol. Cell. Biol.*, 11:143–153 [1991]; EP455,460 published 6 Nov. 1991) and porcine, mouse and rat trkC (Lamballe et al., *Cell*, 66:967–979 [1991]; EP522, 530 published 13 Jan. 1993), were identified as members of the trk receptor family. The structures of the trk receptors are quite similar, but alternate splicing increases the complexity of the family by giving rise to two known forms of trkA, three known forms of trkB (two without functional tyrosine kinase domains) and at least four forms of trkC (several without functional tyrosine kinase domain, and two with small inserts in the tyrosine kinase domain). Human trk A, B and C receptor sequences are disclosed in U.S. patent application Ser. No. 08/215,139, filed Mar. 18, 1994, specifically incorporated herein by reference.

The following KIRA ELISA was performed using trk A, B and C receptor constructs having amino-terminal flag polypeptides.

(i) Capture agent preparation

Monoclonal anti-gD (clone 5B6) was produced against a peptide from Herpes simples virus glycoprotein D as discussed above in Example 2. The purified stock preparation was adjusted to 3.0 mg/ml in phosphate buffered saline (PBS), pH 7.4 and 1.0 ml aliquots were stored at −20° C.

(ii) Anti-phosphotyrosine antibody preparation

Monoclonal anti-phosphotyrosine, clone 4G10, was purchased from Upstate Biologicals, Inc (UBI, Lake Placid, N.Y.) and biotinylated using long-arm biotin-N-hydroxysuccinamide (Biotin-X-NHS, Research Organics, Cleveland, Ohio).

(iii) Ligands

Nerve growth factor (NGF), neurotrophin 3 (NT3), and neurotrophin 5 (NT5) were prepared by recombinant techniques using the sequence data provided for each of these proteins in the above-mentioned references. The purified NGF, NT3 and NT5 were stored at 4° C. as stock solutions (180 μM, 8.8 μM and 26.9 μM, respectively) in PBS, pH 7.5.

(iv) Preparation of gD.trk nucleic acid

In order to express the various trk receptors with gD flags (i.e. gD.trk constructs), DNA constructs were made which encoded the signal and epitope of gD (see Paborsky et al., supra) fused to the amino terminus of the various trk receptors. These were made by inserting the trk receptor and gD sequences into pRK5 or pRK7 (Suva et al., Science, 237:893–896[1987]) using standard molecular biology techniques, to generate the constructs shown in FIGS. 12–14. In addition to the gD.trk constructs, constructs were also made to express gD tagged trk.lgG fusion proteins (i.e., gD.trk.lgG). DNA constructs encoding the chimeras of trk extracellular domain and IgG-1Fc domains were made with the Fc region clones of human IgG-1 (Ashkenazi et al., Immunoadhesins Intern. Rev. Immunol., 10:219–227 [1993]). More specifically, the source of the IgG-1 encoding sequence was the CD4-lgG-1 expression plasmid pRKCD4$_2$Fc$_1$ (Capon et al., Nature, 334:525 [1989 ]; Byrn et al., Nature, 344:667 [1990]) containing a cDNA sequence encoding a hybrid polypeptide consisting of residues 1–180 of the mature human CD4 protein fused to human IgG-1 sequences beginning at aspartic acid 216 (taking amino acid 114 as the first residue of the heavy chain constant region; Kabat et al., Sequences of Proteins of Immunological Interest 4th ed. [1987]), which is the first residue of the IgG-1 hinge after the cysteine residue involved in heavy-light chain bonding, and ending with residues 441 to include the CH2 and CH3 Fc domains of IgG-1. The CD4-encoding sequence was deleted from the expression plasmid pRKCD4$_2$Fc$_1$ and the vector was fused to DNA encoding the trk receptors, with the splice between aspartate 216 of the IgG-1 and valine 402 of trkA, threonine 422 of trkB, or threonine 413 of trkC. The gD tag was added to the amino terminus of each trk.IgG in the same way as for the gD.trk constructs.

(v) Cell transformation

Human embryonic kidney 293 cells (obtained from ATCC, Rockville, Md.) were transiently transfected with the nucleic acid encoding gD.trk.IgG using a calcium phosphate protocol (Gorman, DNA Cloning: A Practical Approach [Glover, D., ed.] Vol II: 143–190, IRL Press, Washington D.C.). After twelve hours, the transformed cells were rinsed three times with serum free F12/DMEM50:50 media (Gibco) and then serum free media was added for a 48 hour collection.

Cell lines stably expressing each of the gD.trk constructs were made by co-transfecting dp12.CHO cells (EP 307,247 published 15 Mar. 1989) with the pRK plasmids encoding the gD tagged trk receptors and a plasmid encoding DHFR, again using calcium phosphate mediated transfection.

The media mentioned above (having the gD.trk.lgG) was used without further purification in binding assays to assess the effects of the presence of the gD flag polypeptide on neurotrophin binding to the gD.trk.lgG polypeptides. DNA encoding untagged trk.IgG polypeptide was run in parallel as a control. trk.IgG and gD tagged trk.lgG containing cell supernatants were prepared as described and used in competitive displacement assays with the appropriate iodinated neurotrophin. NGF is used as ligand for trkA, NT5 is used as ligand for trkB, and NT3 is used as a ligand for trkC. A summary of the results obtained is shown in the following table.

TABLE 2

| Binding of Neurotrophins to trk.IgG | | |
|---|---|---|
| | IC50 without gD | IC50 with gD |
| trkA | 68.4 +/- 11.9 pM | 68.8 +/- 3.0 pM |
| trkB | 31.1 +/- 15.6 pM | 12.1 +/- 18 pM |
| trkC | 31.1 +/- 1.1 pM | 30.2 +/- 0.7 pM |

(vi) Selection of transformed cells for use in the KIRA ELISA

It was apparent from the preceding experiment that there was no observable change in the affinity of interaction of neurotrophins with their receptor due to the presence of the gD flag polypeptide on the amino terminus. Based on this result, cells were transformed with the gD.trk constructs for use in the KIRA ELISA using the techniques described in the previous section.

After two days, dp12.CHO cells (EP 307,247 published 15 Mar. 1989) transformed with gD.trk constructs were selected for by growth in media without GHT, and after two weeks, growing cells were sorted by FACS analysis using the 5B6 monoclonal to select cells expressing the gD flag polypeptide on their surface. gD positive cells were cloned by plating at limiting dilution and resultant colonies were then rescreened by FACS analysis (using the anti-gD 5B6 monoclonal antibody), neurotrophin binding (as discussed above), tyrosine phosphorylation indicated by Western blot using an anti-phosphotyrosine antibody, gD expression by Western blot using th anti-gD 5B6 antibody, and immunocytochemistry using the 5B6 antibody. Clones which were positive were then recloned by limiting dilution and were subjected to the KIRA ELISA as described below.

(vii) Media

Cells were grown in F12/DMEM50:50 (Gibco/BRL, Life Technologies, Grand Island, N.Y.). The media was supplemented with 10% diafiltered FBS (HyClone, Logan, Utah), 25 mM HEPES and 2 mM L-glutamine.

(viii) KIRA ELISA gD.trk transformed dp12.CHO cells (EP 307,247 published 15 Mar. 1989) were seeded ($5 \times 10^4$ per well) in a flat-bottom-96 well culture plate in 100 μl media and cultured overnight at 37° C. in 5% $CO_2$. The following morning the well supernatants were decanted, and the plates were lightly tamped on a paper towel. 100 μl of media containing either experimental samples or the recombinant purified NGF, NT3, or NT5 standards (3000, 1000, 333, 111, 37, 12, 4, and 0 pM) was then added to each well. The cells were stimulated at 37 ° C. for 30 min., the well supernatants were decanted, and the plates were once again lightly tamped on a paper towel. To lyse the cells and solubilize the receptors, 100 μl of lysis buffer was added to each well. Lysis buffer consisted of 150 mM NaCl containing 50 mM HEPES (Gibco), 0.5% Triton-X 100 (Gibco), 0.01% thimerosal, 30 KIU/ml aprotinin (ICN Biochemicals, Aurora, Ohio ), 1 mM 4-(2-aminoethyl)-benzenesulfonyl fluoride hydrochloride (AEBSF; ICN Biochemicals), 50 μM leupeptin (ICN Biochemicals), and 2 mM sodium orthovanadate (Na$_3$VO$_4$; Sigma Chemical Co, St. Louis, Mo.). pH 7.5. The plate was then agitated gently on a plate shaker (Bellco Instruments, Vineland, N.J.) for 60 min. at room temperature.

While the cells were being solubilized, an ELISA microtiter plate (Nunc Maxisorp, Inter Med, Denmark) coated overnight at 4° C. with the 5B6 monoclonal anti-gD antibody (0.5 μg/ml in 50 mM carbonate buffer, pH 9.6, 100 μl/well) was decanted, tamped on a paper towel and blocked with 150 μl/well of Block Buffer [PBS containing 0.5% BSA (Intergen Company, Purchase, N.Y.) and 0.01% thimerosal] for 60 min. at room temperature with gentle agitation. After 60 minutes, the anti-gD 5B6 coated plate was washed 6 times with wash buffer (PBS containing 0.05% Tween-20 and 0.01% thimerosal) using an automated plate washer (ScanWasher 300, Skatron Instruments, Inc, Sterling, Va.).

The lysate containing solubilized gD.trk from the cell-culture microtiter well was transferred (85 μl/well) to anti-gD 5B6 coated and blocked ELISA well and was incubated for 2 h at room temperature with gentle agitation. The unbound gD.trk was removed by washing with wash buffer and 100 μl of biotinylated 4G10 (anti-phosphotyrosine) diluted 1:2000 in dilution buffer (PBS containing 0.5% BSA, 0.05% Tween-20, 5 mM EDTA, and 0.01% thimerosal), i.e., 400 pg/ml, was added to each well. After incubation for 2 h at room temperature the plate was washed and 100 μl of HRPO-conjugated streptavidin (Zymed Laboratories, S. San Francisco, Calif.) diluted 1:10000 in dilution buffer was added to each well. The plate was incubated for 30 minutes at room temperature with gentle agitation. The free avidin-conjugate was washed away and 100 μl freshly prepared substrate solution (tetramethyl benzidine; 2-component substrate kit; Kirkegaard and Perry, Gaithersburg, Md.) was added to each well. The reaction was allowed to proceed for 10 minutes, after which the color development was stopped by the addition of 100 μl/well 1.0M H$_3$PO$_4$. The absorbance at 450 nm was read with a reference wavelength of 650 nm (ABS$_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

The standard curves shown in FIGS. 15A–15C were generated by stimulating gD.trk transformed CHO cells with 3000, 1000, 333, 111, 37, 12, 4, and 0 pM NGF, NT3 or NT5 and were presented as pM neurotrophin vs. mean ABS$_{450/650}$±sd using the DeltaSoft program. Sample concentrations were obtained by interpolation of their absorbance on the standard curve and are expressed in terms of pM neurotrophin activity.

The results presented in this example demonstrate that the KIRA ELISA is a useful method for assaying ligand activation of a receptor construct having an amino terminal flag polypeptide, e.g., activation of gD.trk receptor constructs. Levels of receptor activation in terms of tyrosine phosphorylation are easily quantified and an EC$_{50}$ for a given ligand is readily determined.

---

We claim:

1. An assay for measuring autophosphorylation of a tyrosine kinase receptor comprising the steps of:
   (a) coating a first solid phase with a homogeneous population of eukaryotic cells so that the cells adhere to the first solid phase, wherein, positioned in their membranes, the cells have a receptor construct comprising a flag polypeptide and the tyrosine kinase receptor, wherein said tyrosin kinase receptor is selected from the group consisting of trk A receptor (SEQ ID NO:3), trk B receptor (SEQ ID NO:5) and trk C receptor (SEQ ID NO:7);
   (b) exposing the adhering cells to an analyte which is known contain or is suspected of containing a ligand for the tyrosin kinase receptor;
   (c) solubilizing the adhering cells, thereby releasing cell lysate therefrom;
   (d) coating a second solid phase with a capture agent which binds specifically to the flag polypeptide so that the capture agent adheres to the second solid phase;
   (e) exposing the adhering capture agent to the cell lysate obtained in step (c) so that the receptor construct adheres to the second solid phase;
   (f) washing the second solid phase so as to remove unbound cell lysate;
   (g) exposing the adhering receptor construct to an anti-phosphotyrosine antibody which identifies phosphorylated tyrosine residues in the tyrosine kinase receptor; and
   (h) measuring binding of the anti-phosphotyrosine antibody to the adhering receptor construct, wherein the amount of anti-phosphotyrosine antibody binding to the adhering receptor construct is proportional to the amount of autophosphorylation of said tyrosine kinase receptor.

2. The method of claim 1 wherein the cells are transformed with nucleic acid encoding the receptor construct prior to step (a).

3. The method of claim 1 wherein the cells comprise a mammalian cell line.

4. The method of claim 1 wherein the capture agent comprises a capture antibody.

5. The method of claim 4 wherein the capture antibody comprises an affinity purified polyclonal antibody.

6. The method of claim 4 wherein the capture antibody comprises a monoclonal antibody.

7. The method of claim 1 wherein the first solid phase comprises a well of a first assay plate.

8. The method of claim 7 wherein the first assay plate is a microtiter plate.

9. The method of claim 7 wherein between about $1 \times 10^4$ to $3 \times 10^5$ cells are added to the well in step (a).

10. The method of claim 1 wherein the second solid phase comprises a well of a second assay plate.

11. The method of claim 10 wherein the second assay plate comprises a microtiter plate.

12. The method of claim 1 wherein the cell lysate is not concentrated or clarified prior to step (e).

13. The method of claim 7 wherein step (c) comprises adding a lysis buffer to the well of the first assay plate and gently agitating the first assay plate.

14. The method of claim 13 wherein the lysis buffer comprises a solubilizing detergent.

15. The method of claim 1 wherein the anti-phosphotyrosine antibody is labelled.

16. The method of claim 15 wherein the label is added to the anti-phosphotyrosine antibody after step (g).

17. The method of claim 15 wherein the label is added to the anti-phosphotyrosine antibody prior to step (g).

18. The method of claim 15 wherein the label comprises a non-radioactive label.

19. The method of claim 18 wherein the label comprises an enzyme.

20. The method of claim 19 comprising exposing the enzyme to a color reagent and determining the color change of the color reagent in step (h).

21. The method of claim 1 wherein the flag polypeptide is fused to the amino terminus of the tyrosine kinase receptor.

22. The method of claim 1 wherein the flag polypeptide is fused to the carboxyl terminus of the tyrosine kinase receptor.

23. The method of claim 1 wherein the analyte comprises a ligand for the tyrosine kinase receptor.

24. The method of claim 23 wherein the ligand comprises an agonist for the tyrosine kinase receptor.

25. The method of claim 23 wherein the ligand comprises an antagonist for the tyrosine kinase receptor.

26. The method of claim 25 wherein the antagonist competitively inhibits binding or activation of the tyrosine kinase receptor by an agonist thereto and step (b) is followed by a step wherein the adhering cells are exposed to the agonist.

27. The method of claim 1 wherein the analyte is a composition which comprises an antagonist and an agonist for the receptor and wherein the amount of anti-phosphotyrosine antibody binding to the adhering receptor construct directly correlates with the ability of the antagonist to bind to the agonist and thereby reduce activation of the tyrosine kinase receptor by the agonist.

28. The method of claim 1 wherein a block buffer is added to the second solid phase following step (d).

29. An assay for measuring autophosphorylation of a tyrosine kinase receptor comprising the steps of:
- (a) coating a well of a first assay plate with a homogeneous population of adherent cells so that the cells adhere to the well, wherein the cells have a tyrosine kinase receptor positioned in the cell membrane thereof, wherein said tyrosine kinase receptor is selected from the group consisting of trk A receptor (SEQ ID NO:3), trk B receptor (SEQ ID NO:5) and trk C receptor (SEQ ID NO:7);
- (b) exposing the adhering cells to an analyte which is known to contain or is suspected of containing a ligand for the tyrosine kinase receptor;
- (c) solubilizing the adhering cells thereby releasing cell lysate therefrom;
- (d) coating a well of a second assay plate with a capture agent which binds specifically to the tyrosine kinase receptor so that the capture agent adheres to the well;
- (e) exposing the cell lysate obtained in step (c) to the adhering capture agent so that the tyrosine kinase receptor adheres to the well;
- (f) washing the well so as to remove unbound cell lysate;
- (g) exposing the adhering tyrosine kinase receptor to an anti-phosphotyrosine antibody which binds selectively to phosphorylated tyrosine residues in the tyrosine kinase receptor; and
- (h) measuring binding of the anti-phosphotyrosine antibody to the adhering tyrosine kinase receptor, wherein the amount of anti-phosphotyrosine antibody binding to the adhering tyrosine kinase receptor is proportional to the amount of autophosphorylation of said tyrosine kinase receptor.

* * * * *

UNITED STATES PATENT AND TRADEMARK OFFICE
CERTIFICATE OF CORRECTION

PATENT NO. : 5,891,650

DATED : April 6, 1999

INVENTOR(S) : Godowski et al.

It is certified that error appears in the above-identified patent and that said Letters Patent is hereby corrected as shown below:

In column 81, claim 1, line 25, please delete "tyrosin" and insert therefor --tyrosine--.

In column 81, claim 1, line 30, insert --to-- before "contain".

In column 81, claim 1, line 31, please delete "tyrosin" and insert therefor --tyrosine--.

Signed and Sealed this

Fourteenth Day of December, 1999

Attest:

Q. TODD DICKINSON

*Attesting Officer*          *Acting Commissioner of Patents and Trademarks*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 911 amino acids
        ( B ) TYPE: amino acid
        ( D ) TOPOLOGY: linear ( x i ) SEQUENCE DESCRIPTION: SEQ ID NO:1:

```
Met Ala Leu Arg Arg Ser Met Gly Arg Pro Gly Leu Pro Pro Leu
 1               5                  10                  15

Pro Leu Pro Pro Pro Pro Arg Leu Gly Leu Leu Leu Ala Ala Leu
                20                  25                  30

Ala Ser Leu Leu Leu Pro Glu Ser Ala Ala Ala Gly Leu Lys Leu
                35                  40                  45

Met Gly Ala Pro Val Lys Leu Thr Val Ser Gln Gly Gln Pro Val
                50                  55                  60

Lys Leu Asn Cys Ser Val Glu Gly Met Glu Glu Pro Asp Ile Gln
                65                  70                  75

Trp Val Lys Asp Gly Ala Val Val Gln Asn Leu Asp Gln Leu Tyr
                80                  85                  90

Ile Pro Val Ser Glu Gln His Trp Ile Gly Phe Leu Ser Leu Lys
                95                  100                 105

Ser Val Glu Arg Ser Asp Ala Gly Arg Tyr Trp Cys Gln Val Glu
                110                 115                 120

Asp Gly Gly Glu Thr Glu Ile Ser Gln Pro Val Trp Leu Thr Val
```

-continued

|     |     |     |     | 125 |     |     |     |     | 130 |     |     |     |     | 135 |
| --- | --- | --- | --- | --- | --- | --- | --- | --- | --- | --- | --- | --- | --- | --- |
| Glu | Gly | Val | Pro | Phe | Phe | Thr | Val | Glu | Pro | Lys | Asp | Leu | Ala | Val |
|     |     |     |     | 140 |     |     |     |     | 145 |     |     |     |     | 150 |
| Pro | Pro | Asn | Ala | Pro | Phe | Gln | Leu | Ser | Cys | Glu | Ala | Val | Gly | Pro |
|     |     |     |     | 155 |     |     |     |     | 160 |     |     |     |     | 165 |
| Pro | Glu | Pro | Val | Thr | Ile | Val | Trp | Trp | Arg | Gly | Thr | Thr | Lys | Ile |
|     |     |     |     | 170 |     |     |     |     | 175 |     |     |     |     | 180 |
| Gly | Gly | Pro | Ala | Pro | Ser | Pro | Ser | Val | Leu | Asn | Val | Thr | Gly | Val |
|     |     |     |     | 185 |     |     |     |     | 190 |     |     |     |     | 195 |
| Thr | Gln | Ser | Thr | Met | Phe | Ser | Cys | Glu | Ala | His | Asn | Leu | Lys | Gly |
|     |     |     |     | 200 |     |     |     |     | 205 |     |     |     |     | 210 |
| Leu | Ala | Ser | Ser | Arg | Thr | Ala | Thr | Val | His | Leu | Gln | Ala | Leu | Pro |
|     |     |     |     | 215 |     |     |     |     | 220 |     |     |     |     | 225 |
| Ala | Ala | Pro | Phe | Asn | Ile | Thr | Val | Thr | Lys | Leu | Ser | Ser | Ser | Asn |
|     |     |     |     | 230 |     |     |     |     | 235 |     |     |     |     | 240 |
| Ala | Ser | Val | Ala | Trp | Met | Pro | Gly | Ala | Asp | Gly | Arg | Ala | Leu | Leu |
|     |     |     |     | 245 |     |     |     |     | 250 |     |     |     |     | 255 |
| Gln | Ser | Cys | Thr | Val | Gln | Val | Thr | Gln | Ala | Pro | Gly | Gly | Trp | Glu |
|     |     |     |     | 260 |     |     |     |     | 265 |     |     |     |     | 270 |
| Val | Leu | Ala | Val | Val | Val | Pro | Val | Pro | Phe | Thr | Cys | Leu | Leu |     |
|     |     |     |     | 275 |     |     |     |     | 280 |     |     |     |     | 285 |
| Arg | Asp | Leu | Val | Pro | Ala | Thr | Asn | Tyr | Ser | Leu | Arg | Val | Arg | Cys |
|     |     |     |     | 290 |     |     |     |     | 295 |     |     |     |     | 300 |
| Ala | Asn | Ala | Leu | Gly | Pro | Ser | Pro | Tyr | Ala | Asp | Trp | Val | Pro | Phe |
|     |     |     |     | 305 |     |     |     |     | 310 |     |     |     |     | 315 |
| Gln | Thr | Lys | Gly | Leu | Ala | Pro | Ala | Ser | Ala | Pro | Gln | Asn | Leu | His |
|     |     |     |     | 320 |     |     |     |     | 325 |     |     |     |     | 330 |
| Ala | Ile | Arg | Thr | Asp | Ser | Gly | Leu | Ile | Leu | Glu | Trp | Glu | Glu | Val |
|     |     |     |     | 335 |     |     |     |     | 340 |     |     |     |     | 345 |
| Ile | Pro | Glu | Ala | Pro | Leu | Glu | Gly | Pro | Leu | Gly | Pro | Tyr | Lys | Leu |
|     |     |     |     | 350 |     |     |     |     | 355 |     |     |     |     | 360 |
| Ser | Trp | Val | Gln | Asp | Asn | Gly | Thr | Gln | Asp | Glu | Leu | Thr | Val | Glu |
|     |     |     |     | 365 |     |     |     |     | 370 |     |     |     |     | 375 |
| Gly | Thr | Arg | Ala | Asn | Leu | Thr | Gly | Trp | Asp | Pro | Gln | Lys | Asp | Leu |
|     |     |     |     | 380 |     |     |     |     | 385 |     |     |     |     | 390 |
| Ile | Val | Arg | Val | Cys | Val | Ser | Asn | Ala | Val | Gly | Cys | Gly | Pro | Trp |
|     |     |     |     | 395 |     |     |     |     | 400 |     |     |     |     | 405 |
| Ser | Gln | Pro | Leu | Val | Val | Ser | Ser | His | Asp | Arg | Ala | Gly | Gln | Gln |
|     |     |     |     | 410 |     |     |     |     | 415 |     |     |     |     | 420 |
| Gly | Pro | Pro | His | Ser | Arg | Thr | Ser | Trp | Val | Pro | Val | Val | Leu | Gly |
|     |     |     |     | 425 |     |     |     |     | 430 |     |     |     |     | 435 |
| Val | Leu | Thr | Ala | Leu | Val | Thr | Ala | Ala | Leu | Ala | Leu | Ile | Leu |     |
|     |     |     |     | 440 |     |     |     |     | 445 |     |     |     |     | 450 |
| Leu | Arg | Lys | Arg | Arg | Lys | Glu | Thr | Arg | Phe | Gly | Gln | Ala | Phe | Asp |
|     |     |     |     | 455 |     |     |     |     | 460 |     |     |     |     | 465 |
| Ser | Val | Met | Ala | Arg | Gly | Glu | Pro | Ala | Val | His | Phe | Arg | Ala | Ala |
|     |     |     |     | 470 |     |     |     |     | 475 |     |     |     |     | 480 |
| Arg | Ser | Phe | Asn | Arg | Glu | Arg | Pro | Glu | Arg | Ile | Glu | Ala | Thr | Leu |
|     |     |     |     | 485 |     |     |     |     | 490 |     |     |     |     | 495 |
| Asp | Ser | Leu | Gly | Ile | Ser | Asp | Glu | Leu | Lys | Glu | Lys | Leu | Glu | Asp |
|     |     |     |     | 500 |     |     |     |     | 505 |     |     |     |     | 510 |
| Val | Leu | Ile | Pro | Glu | Gln | Gln | Phe | Thr | Leu | Gly | Arg | Met | Leu | Gly |
|     |     |     |     | 515 |     |     |     |     | 520 |     |     |     |     | 525 |

Lys Gly Glu Phe Gly Ser Val Arg Glu Ala Gln Leu Lys Gln Glu
            530                     535                 540

Asp Gly Ser Phe Val Lys Val Ala Val Lys Met Leu Lys Ala Asp
            545                     550                 555

Ile Ile Ala Ser Ser Asp Ile Glu Glu Phe Leu Arg Glu Ala Ala
            560                     565                 570

Cys Met Lys Glu Phe Asp His Pro His Val Ala Lys Leu Val Gly
            575                     580                 585

Val Ser Leu Arg Ser Arg Ala Lys Gly Arg Leu Pro Ile Pro Met
            590                     595                 600

Val Ile Leu Pro Phe Met Lys His Gly Asp Leu His Ala Phe Leu
            605                     610                 615

Leu Ala Ser Arg Ile Gly Glu Asn Pro Phe Asn Leu Pro Leu Gln
            620                     625                 630

Thr Leu Ile Arg Phe Met Val Asp Ile Ala Cys Gly Met Glu Tyr
            635                     640                 645

Leu Ser Ser Arg Asn Phe Ile His Arg Asp Leu Ala Ala Arg Asn
            650                     655                 660

Cys Met Leu Ala Glu Asp Met Thr Val Cys Val Ala Asp Phe Gly
            665                     670                 675

Leu Ser Arg Lys Ile Tyr Ser Gly Asp Tyr Tyr Arg Gln Gly Cys
            680                     685                 690

Ala Ser Lys Leu Pro Val Lys Trp Leu Ala Leu Glu Ser Leu Ala
            695                     700                 705

Asp Asn Leu Tyr Thr Val Gln Ser Asp Val Trp Ala Phe Gly Val
            710                     715                 720

Thr Met Trp Glu Ile Met Thr Arg Gly Gln Thr Pro Tyr Ala Gly
            725                     730                 735

Ile Glu Asn Ala Glu Ile Tyr Asn Tyr Leu Ile Gly Gly Asn Arg
            740                     745                 750

Leu Lys Gln Pro Pro Glu Cys Met Glu Asp Val Tyr Asp Leu Met
            755                     760                 765

Tyr Gln Cys Trp Ser Ala Asp Pro Lys Gln Arg Pro Ser Phe Thr
            770                     775                 780

Cys Leu Arg Met Glu Leu Glu Asn Ile Leu Gly Gln Leu Ser Val
            785                     790                 795

Leu Ser Ala Ser Gln Asp Pro Leu Tyr Ile Asn Ile Glu Arg Ala
            800                     805                 810

Glu Glu Pro Thr Ala Gly Gly Ser Leu Glu Leu Pro Gly Arg Asp
            815                     820                 825

Gln Pro Tyr Ser Gly Ala Gly Asp Gly Ser Gly Met Gly Ala Val
            830                     835                 840

Gly Gly Thr Pro Ser Asp Cys Arg Tyr Ile Leu Thr Pro Gly Gly
            845                     850                 855

Leu Ala Glu Gln Pro Gly Gln Ala Glu His Gln Pro Glu Ser Pro
            860                     865                 870

Leu Asn Glu Thr Gln Arg Leu Leu Leu Leu Gln Gln Gly Leu Leu
            875                     880                 885

Pro His Ser Ser Cys Ala Asp Ala Ser Leu Lys Met Ala Asp Pro
            890                     895                 900

Asn Arg Phe Arg Gly Lys Asp Leu Pro Val Leu
            905                     910 911

( 2 ) INFORMATION FOR SEQ ID NO:2:

( i ) SEQUENCE CHARACTERISTICS:
  ( A ) LENGTH: 2742 bases
  ( B ) TYPE: nucleic acid
  ( C ) STRANDEDNESS: single
  ( D ) TOPOLOGY: linear ( x i ) SEQUENCE DESCRIPTION: SEQ ID NO:2:

| | | | | | |
|---|---|---|---|---|---|
| ATGGCGCTGA | GGCGGAGCAT | GGGGCGGCCG | GGGCTCCCGC | CGCTGCCGCT | 50 |
| GCCGCCGCCA | CCGCGGCTCG | GGCTGCTGCT | GGCGGCTCTG | GCTTCTCTGC | 100 |
| TGCTCCCGGA | GTCCGCCGCC | GCAGGTCTGA | AGCTCATGGG | AGCCCCGGTG | 150 |
| AAGCTGACAG | TGTCTCAGGG | GCAGCCGGTG | AAGCTCAACT | GCAGTGTGGA | 200 |
| GGGGATGGAG | GAGCCTGACA | TCCAGTGGGT | GAAGGATGGG | CTGTGGTCC | 250 |
| AGAACTTGGA | CCAGTTGTAC | ATCCAGTCA | GCGAGCAGCA | CTGGATCGGC | 300 |
| TTCCTCAGCC | TGAAGTCAGT | GGAGCGCTCT | GACGCCGGCC | GGTACTGGTG | 350 |
| CCAGGTGGAG | GATGGGGGTG | AAACCGAGAT | CTCCCAGCCA | GTGTGGCTCA | 400 |
| CGGTAGAAGG | TGTGCCATTT | TTCACAGTGG | AGCCAAAAGA | TCTGGCAGTG | 450 |
| CCACCCAATG | CCCCTTTCCA | ACTGTCTTGT | GAGGCTGTGG | GTCCCCCTGA | 500 |
| ACCTGTTACC | ATTGTCTGGT | GGAGAGGAAC | TACGAAGATC | GGGGGACCCG | 550 |
| CTCCCTCTCC | ATCTGTTTTA | AATGTAACAG | GGGTGACCCA | GAGCACCATG | 600 |
| TTTTCCTGTG | AAGCTCACAA | CCTAAAAGGC | CTGGCCTCTT | CTCGCACAGC | 650 |
| CACTGTTCAC | CTTCAAGCAC | TGCCTGCAGC | CCCCTTCAAC | ATCACCGTGA | 700 |
| CAAAGCTTTC | CAGCAGCAAC | GCTAGTGTGG | CCTGGATGCC | AGGTGCTGAT | 750 |
| GGCCGAGCTC | TGCTACAGTC | CTGTACAGTT | CAGGTGACAC | AGGCCCCAGG | 800 |
| AGGCTGGGAA | GTCCTGGCTG | TTGTGGTCCC | TGTGCCCCCC | TTTACCTGCC | 850 |
| TGCTCCGGGA | CCTGGTGCCT | GCCACCAACT | ACAGCCTCAG | GGTGCGCTGT | 900 |
| GCCAATGCCT | GGGGCCCTC | TCCCTATGCT | GACTGGGTGC | CCTTTCAGAC | 950 |
| CAAGGGTCTA | GCCCCAGCCA | GCGCTCCCCA | AAACCTCCAT | GCCATCCGCA | 1000 |
| CAGATTCAGG | CCTCATCTTG | GAGTGGGAAG | AAGTGATCCC | CGAGGCCCCT | 1050 |
| TTGGAAGGCC | CCCTGGGACC | CTACAAACTG | TCCTGGGTTC | AAGACAATGG | 1100 |
| AACCCAGGAT | GAGCTGACAG | TGGAGGGGAC | CAGGGCCAAT | TTGACAGGCT | 1150 |
| GGGATCCCCA | AAAGGACCTG | ATCGTACGTG | TGTGCGTCTC | CAATGCAGTT | 1200 |
| GGCTGTGGAC | CCTGGAGTCA | GCCACTGGTG | GTCTCTTCTC | ATGACCGTGC | 1250 |
| AGGCCAGCAG | GGCCCTCCTC | ACAGCCGCAC | ATCCTGGGTA | CCTGTGGTCC | 1300 |
| TTGGTGTGCT | AACGGCCCTG | GTGACGGCTG | CTGCCCTGGC | CCTCATCCTG | 1350 |
| CTTCGAAAGA | GACGGAAAGA | GACGCGGTTT | GGGCAAGCCT | TTGACAGTGT | 1400 |
| CATGGCCCGG | GGAGAGCCAG | CCGTTCACTT | CCGGGCAGCC | CGGTCCTTCA | 1450 |
| ATCGAGAAAG | GCCCGAGCGC | ATCGAGGCCA | CATTGGACAG | CTTGGGCATC | 1500 |
| AGCGATGAAC | TAAAGGAAAA | ACTGGAGGAT | GTGCTCATCC | AGAGCAGCA | 1550 |
| GTTCACCCTG | GGCCGGATGT | TGGGCAAAGG | AGAGTTTGGT | TCAGTGCGGG | 1600 |
| AGGCCCAGCT | GAAGCAAGAG | GATGGCTCCT | TTGTGAAAGT | GGCTGTGAAG | 1650 |
| ATGCTGAAAG | CTGACATCAT | TGCCTCAAGC | GACATTGAAG | AGTTCCTCAG | 1700 |
| GGAAGCAGCT | TGCATGAAGG | AGTTTGACCA | TCCACACGTG | GCCAAACTTG | 1750 |
| TTGGGGTAAG | CCTCCGGAGC | AGGGCTAAAG | GCCGTCTCCC | CATCCCCATG | 1800 |

```
GTCATCTTGC  CCTTCATGAA  GCATGGGGAC  CTGCATGCCT  TCCTGCTCGC            1850

CTCCCGGATT  GGGGAGAACC  CCTTTAACCT  ACCCCTCCAG  ACCCTGATCC            1900

GGTTCATGGT  GGACATTGCC  TGCGGCATGG  AGTACCTGAG  CTCTCGGAAC            1950

TTCATCCACC  GAGACCTGGC  TGCTCGGAAT  TGCATGCTGG  CAGAGGACAT            2000

GACAGTGTGT  GTGGCTGACT  TCGGACTCTC  CCGGAAGATC  TACAGTGGGG            2050

ACTACTATCG  TCAAGGCTGT  GCCTCCAAAC  TGCCTGTCAA  GTGGCTGGCC            2100

CTGGAGAGCC  TGGCCGACAA  CCTGTATACT  GTGCAGAGTG  ACGTGTGGGC            2150

GTTCGGGGTG  ACCATGTGGG  AGATCATGAC  ACGTGGGCAG  ACGCCATATG            2200

CTGGCATCGA  AAACGCTGAG  ATTTACAACT  ACCTCATTGG  CGGGAACCGC            2250

CTGAAACAGC  CTCCGGAGTG  TATGGAGGAC  GTGTATGATC  TCATGTACCA            2300

GTGCTGGAGT  GCTGACCCCA  AGCAGCGCCC  GAGCTTTACT  TGTCTGCGAA            2350

TGGAACTGGA  GAACATCTTG  GGCCAGCTGT  CTGTGCTATC  TGCCAGCCAG            2400

GACCCCTTAT  ACATCAACAT  CGAGAGAGCT  GAGGAGCCCA  CTGCGGGAGG            2450

CAGCCTGGAG  CTACCTGGCA  GGGATCAGCC  CTACAGTGGG  GCTGGGGATG            2500

GCAGTGGCAT  GGGGGCAGTG  GGTGGCACTC  CCAGTGACTG  TCGGTACATA            2550

CTCACCCCCG  GAGGGCTGGC  TGAGCAGCCA  GGGCAGGCAG  AGCACCAGCC            2600

AGAGAGTCCC  CTCAATGAGA  CACAGAGGCT  TTTGCTGCTG  CAGCAAGGGC            2650

TACTGCCACA  CTCGAGCTGC  GCAGATGCTA  GCCTCAAGAT  GGCTGATCCA            2700

AATCGATTCC  GCGGCAAAGA  TCTTCCGGTC  CTGTAGAAGC  TT                    2742
```

(2) INFORMATION FOR SEQ ID NO:3:

(i) SEQUENCE CHARACTERISTICS:
    (A) LENGTH: 814 amino acids
    (B) TYPE: amino acid
    (D) TOPOLOGY: linear (xi) SEQUENCE DESCRIPTION: SEQ ID NO:3:

```
Met  Gly  Gly  Thr  Ala  Ala  Arg  Leu  Gly  Ala  Val  Ile  Leu  Phe  Val
 1                  5                   10                      15

Val  Ile  Val  Gly  Leu  His  Gly  Val  Arg  Gly  Lys  Tyr  Ala  Leu  Ala
                    20                  25                      30

Asp  Ala  Ser  Leu  Lys  Met  Ala  Asp  Pro  Asn  Arg  Phe  Arg  Gly  Lys
                    35                  40                      45

Asp  Leu  Pro  Val  Leu  Asp  Gln  Leu  Leu  Glu  Val  Ala  Ala  Pro  Cys
                    50                  55                      60

Pro  Asp  Ala  Cys  Cys  Pro  His  Gly  Ser  Ser  Gly  Leu  Arg  Cys  Thr
                    65                  70                      75

Arg  Asp  Gly  Ala  Leu  Asp  Ser  Leu  His  His  Leu  Pro  Gly  Ala  Glu
                    80                  85                      90

Asn  Leu  Thr  Glu  Leu  Tyr  Ile  Glu  Asn  Gln  Gln  His  Leu  Gln  His
                    95                  100                     105

Leu  Glu  Leu  Arg  Asp  Leu  Arg  Gly  Leu  Gly  Glu  Leu  Arg  Asn  Leu
                    110                 115                     120

Thr  Ile  Val  Lys  Ser  Gly  Leu  Arg  Phe  Val  Ala  Pro  Asp  Ala  Phe
                    125                 130                     135

His  Phe  Thr  Pro  Arg  Leu  Ser  Arg  Leu  Asn  Leu  Ser  Phe  Asn  Ala
                    140                 145                     150

Leu  Glu  Ser  Leu  Ser  Trp  Lys  Thr  Val  Gln  Gly  Leu  Ser  Leu  Gln
```

|     |     |     |     | 155 |     |     |     |     | 160 |     |     |     |     | 165 |
| --- | --- | --- | --- | --- | --- | --- | --- | --- | --- | --- | --- | --- | --- | --- |
| Glu | Leu | Val | Leu | Ser | Gly | Asn | Pro | Leu | His | Cys | Ser | Cys | Ala | Leu |
|     |     |     |     | 170 |     |     |     |     | 175 |     |     |     |     | 180 |
| Arg | Trp | Leu | Gln | Arg | Trp | Glu | Glu | Gly | Leu | Gly | Gly | Val | Pro |     |
|     |     |     |     | 185 |     |     |     |     | 190 |     |     |     |     | 195 |
| Glu | Gln | Lys | Leu | Gln | Cys | His | Gly | Gln | Gly | Pro | Leu | Ala | His | Met |
|     |     |     |     | 200 |     |     |     |     | 205 |     |     |     |     | 210 |
| Pro | Asn | Ala | Ser | Cys | Gly | Val | Pro | Thr | Leu | Lys | Val | Gln | Val | Pro |
|     |     |     |     | 215 |     |     |     |     | 220 |     |     |     |     | 225 |
| Asn | Ala | Ser | Val | Asp | Val | Gly | Asp | Val | Leu | Leu | Arg | Cys | Gln |     |
|     |     |     |     | 230 |     |     |     |     | 235 |     |     |     |     | 240 |
| Val | Glu | Gly | Arg | Gly | Leu | Glu | Gln | Ala | Gly | Trp | Ile | Leu | Thr | Glu |
|     |     |     |     | 245 |     |     |     |     | 250 |     |     |     |     | 255 |
| Leu | Glu | Gln | Ser | Ala | Thr | Val | Met | Lys | Ser | Gly | Gly | Leu | Pro | Ser |
|     |     |     |     | 260 |     |     |     |     | 265 |     |     |     |     | 270 |
| Leu | Gly | Leu | Thr | Leu | Ala | Asn | Val | Thr | Ser | Asp | Leu | Asn | Arg | Lys |
|     |     |     |     | 275 |     |     |     |     | 280 |     |     |     |     | 285 |
| Asn | Leu | Thr | Cys | Trp | Ala | Glu | Asn | Asp | Val | Gly | Arg | Ala | Glu | Val |
|     |     |     |     | 290 |     |     |     |     | 295 |     |     |     |     | 300 |
| Ser | Val | Gln | Val | Asn | Val | Ser | Phe | Pro | Ala | Ser | Val | Gln | Leu | His |
|     |     |     |     | 305 |     |     |     |     | 310 |     |     |     |     | 315 |
| Thr | Ala | Val | Glu | Met | His | His | Trp | Cys | Ile | Pro | Phe | Ser | Val | Asp |
|     |     |     |     | 320 |     |     |     |     | 325 |     |     |     |     | 330 |
| Gly | Gln | Pro | Ala | Pro | Ser | Leu | Arg | Trp | Leu | Phe | Asn | Gly | Ser | Val |
|     |     |     |     | 335 |     |     |     |     | 340 |     |     |     |     | 345 |
| Leu | Asn | Glu | Thr | Ser | Phe | Ile | Phe | Thr | Glu | Phe | Leu | Glu | Pro | Ala |
|     |     |     |     | 350 |     |     |     |     | 355 |     |     |     |     | 360 |
| Ala | Asn | Glu | Thr | Val | Arg | His | Gly | Cys | Leu | Arg | Leu | Asn | Gln | Pro |
|     |     |     |     | 365 |     |     |     |     | 370 |     |     |     |     | 375 |
| Thr | His | Val | Asn | Asn | Gly | Asn | Tyr | Thr | Leu | Leu | Ala | Ala | Asn | Pro |
|     |     |     |     | 380 |     |     |     |     | 385 |     |     |     |     | 390 |
| Phe | Gly | Gln | Ala | Ser | Ala | Ser | Ile | Met | Ala | Ala | Phe | Met | Asp | Asn |
|     |     |     |     | 395 |     |     |     |     | 400 |     |     |     |     | 405 |
| Pro | Phe | Glu | Phe | Asn | Pro | Glu | Asp | Pro | Ile | Pro | Asp | Thr | Asn | Ser |
|     |     |     |     | 410 |     |     |     |     | 415 |     |     |     |     | 420 |
| Thr | Ser | Gly | Asp | Pro | Val | Glu | Lys | Lys | Asp | Glu | Thr | Pro | Phe | Gly |
|     |     |     |     | 425 |     |     |     |     | 430 |     |     |     |     | 435 |
| Val | Ser | Val | Ala | Val | Gly | Leu | Ala | Val | Phe | Ala | Cys | Leu | Phe | Leu |
|     |     |     |     | 440 |     |     |     |     | 445 |     |     |     |     | 450 |
| Ser | Thr | Leu | Leu | Leu | Val | Leu | Asn | Lys | Cys | Gly | Arg | Arg | Asn | Lys |
|     |     |     |     | 455 |     |     |     |     | 460 |     |     |     |     | 465 |
| Phe | Gly | Ile | Asn | Arg | Pro | Ala | Val | Leu | Ala | Pro | Glu | Asp | Gly | Leu |
|     |     |     |     | 470 |     |     |     |     | 475 |     |     |     |     | 480 |
| Ala | Met | Ser | Leu | His | Phe | Met | Thr | Leu | Gly | Gly | Ser | Ser | Leu | Ser |
|     |     |     |     | 485 |     |     |     |     | 490 |     |     |     |     | 495 |
| Pro | Thr | Glu | Gly | Lys | Gly | Ser | Gly | Leu | Gln | Gly | His | Ile | Ile | Glu |
|     |     |     |     | 500 |     |     |     |     | 505 |     |     |     |     | 510 |
| Asn | Pro | Gln | Tyr | Phe | Ser | Asp | Ala | Cys | Val | His | His | Ile | Lys | Arg |
|     |     |     |     | 515 |     |     |     |     | 520 |     |     |     |     | 525 |
| Arg | Asp | Ile | Val | Leu | Lys | Trp | Glu | Leu | Gly | Glu | Gly | Ala | Phe | Gly |
|     |     |     |     | 530 |     |     |     |     | 535 |     |     |     |     | 540 |
| Lys | Val | Phe | Leu | Ala | Glu | Cys | His | Asn | Leu | Leu | Pro | Glu | Gln | Asp |
|     |     |     |     | 545 |     |     |     |     | 550 |     |     |     |     | 555 |

| | | | | | | | | | | | | | | |
|---|---|---|---|---|---|---|---|---|---|---|---|---|---|---|
| Lys | Met | Leu | Val | Ala 560 | Val | Lys | Ala | Leu | Lys 565 | Glu | Ala | Ser | Glu | Ser 570 |
| Ala | Arg | Gln | Asp | Phe 575 | Gln | Arg | Glu | Ala | Glu 580 | Leu | Leu | Thr | Met | Leu 585 |
| Gln | His | Gln | His | Ile 590 | Val | Arg | Phe | Phe | Gly 595 | Val | Cys | Thr | Glu | Gly 600 |
| Arg | Pro | Leu | Leu | Met 605 | Val | Phe | Glu | Tyr | Met 610 | Arg | His | Gly | Asp | Leu 615 |
| Asn | Arg | Phe | Leu | Arg 620 | Ser | His | Gly | Pro | Asp 625 | Ala | Lys | Leu | Leu | Ala 630 |
| Gly | Gly | Glu | Asp | Val 635 | Ala | Pro | Gly | Pro | Leu 640 | Gly | Leu | Gly | Gln | Leu 645 |
| Leu | Ala | Val | Ala | Ser 650 | Gln | Val | Ala | Ala | Gly 655 | Met | Val | Tyr | Leu | Ala 660 |
| Gly | Leu | His | Phe | Val 665 | His | Arg | Asp | Leu | Ala 670 | Thr | Arg | Asn | Cys | Leu 675 |
| Val | Gly | Gln | Gly | Leu 680 | Val | Val | Lys | Ile | Gly 685 | Asp | Phe | Gly | Met | Ser 690 |
| Arg | Asp | Ile | Tyr | Ser 695 | Thr | Asp | Tyr | Tyr | Arg 700 | Val | Gly | Gly | Arg | Thr 705 |
| Met | Leu | Pro | Ile | Arg 710 | Trp | Met | Pro | Pro | Glu 715 | Ser | Ile | Leu | Tyr | Arg 720 |
| Lys | Phe | Thr | Thr | Glu 725 | Ser | Asp | Val | Trp | Ser 730 | Phe | Gly | Val | Val | Leu 735 |
| Trp | Glu | Ile | Phe | Thr 740 | Tyr | Gly | Lys | Gln | Pro 745 | Trp | Tyr | Gln | Leu | Ser 750 |
| Asn | Thr | Glu | Ala | Ile 755 | Asp | Cys | Ile | Thr | Gln 760 | Gly | Arg | Glu | Leu | Glu 765 |
| Arg | Pro | Arg | Ala | Cys 770 | Pro | Pro | Glu | Val | Tyr 775 | Ala | Ile | Met | Arg | Gly 780 |
| Cys | Trp | Gln | Arg | Glu 785 | Pro | Gln | Gln | Arg | His 790 | Ser | Ile | Lys | Asp | Val 795 |
| His | Ala | Arg | Leu | Gln 800 | Ala | Leu | Ala | Gln | Ala 805 | Pro | Pro | Val | Tyr | Leu 810 |
| Asp | Val | Leu | Gly 814 | | | | | | | | | | | |

( 2 ) INFORMATION FOR SEQ ID NO:4:

( i ) SEQUENCE CHARACTERISTICS:
        ( A ) LENGTH: 2820 bases
        ( B ) TYPE: nucleic acid
        ( C ) STRANDEDNESS: double
        ( D ) TOPOLOGY: linear ( x i ) SEQUENCE DESCRIPTION: SEQ ID NO:4:

```
TATAGAATAA   CATCCACTTT   GCCTTTCTCT   CCACAGGTGT   CCACTCCCAG                50
GTCCAACTGC   ACCTGAATTC   CACTGCCTTC   CACCAAGCTC   TGCAGGATCC               100
CAGAGTCAGG   GGTCTGTATC   TTCCTGCTGG   TGGCTCCAGT   TCAGGAACAG               150
TAAACCCTGC   TCCGAATATT   GCCTCTCACA   TCTCGTCAAT   CTCCGCGAGG               200
ACTGGGGACC   CTGTGACAAG   CTTCAGCGCG   AACGACCAAC   TACCCCGATC               250
ATCAGTTATC   CTTAAGGTCT   CTTTTGTGTG   GTGCGTTCCG   GTATGGGGGG               300
GACTGCCGCC   AGGTTGGGGG   CCGTGATTTT   GTTTGTCGTC   ATAGTGGGCC               350
TCCATGGGGT   CCGCGGCAAA   TATGCCTTGG   CGGATGCCTC   TCTCAAGATG               400
```

| | | | | | |
|---|---|---|---|---|---|
| GCCGACCCCA | ATCGATTTCG | CGGCAAAGAC | CTTCCGGTCC | TGGACCAGCT | 450 |
| GCTCGAGGTA | GCCGCACCCT | GCCCCGATGC | CTGCTGCCCC | CACGGCTCCT | 500 |
| CGGGACTGCG | ATGCACCCGG | GATGGGCCC | TGGATAGCCT | CCACCACCTG | 550 |
| CCCGGCGCAG | AGAACCTGAC | TGAGCTCTAC | ATCGAGAACC | AGCAGCATCT | 600 |
| GCAGCATCTG | GAGCTCCGTG | ATCTGAGGGG | CCTGGGGGAG | CTGAGAAACC | 650 |
| TCACCATCGT | GAAGAGTGGT | CTCCGTTTCG | TGGCGCCAGA | TGCCTTCCAT | 700 |
| TTCACTCCTC | GGCTCAGTCG | CCTGAATCTC | TCCTTCAACG | CTCTGGAGTC | 750 |
| TCTCTCCTGG | AAAACTGTGC | AGGGCCTCTC | CTTACAGGAA | CTGGTCCTGT | 800 |
| CGGGGAACCC | TCTGCACTGT | TCTTGTGCCC | TGCGCTGGCT | ACAGCGCTGG | 850 |
| GAGGAGGAGG | GACTGGGCGG | AGTGCCTGAA | CAGAAGCTGC | AGTGTCATGG | 900 |
| GCAAGGGCCC | CTGGCCCACA | TGCCCAATGC | CAGCTGTGGT | GTGCCCACGC | 950 |
| TGAAGGTCCA | GGTGCCCAAT | GCCTCGGTGG | ATGTGGGGGA | CGACGTGCTG | 1000 |
| CTGCGGTGCC | AGGTGGAGGG | GCGGGGCCTG | GAGCAGGCCG | GCTGGATCCT | 1050 |
| CACAGAGCTG | GAGCAGTCAG | CCACGGTGAT | GAAATCTGGG | GGTCTGCCAT | 1100 |
| CCCTGGGGCT | GACCCTGGCC | AATGTCACCA | GTGACCTCAA | CAGGAAGAAC | 1150 |
| TTGACGTGCT | GGGCAGAGAA | CGATGTGGGC | CGGGCAGAGG | TCTCTGTTCA | 1200 |
| GGTCAACGTC | TCCTTCCCGG | CCAGTGTGCA | GCTGCACACG | GCGGTGGAGA | 1250 |
| TGCACCACTG | GTGCATCCCC | TTCTCTGTGG | ATGGGCAGCC | GGCACCGTCT | 1300 |
| CTGCGCTGGC | TCTTCAATGG | CTCCGTGCTC | AATGAGACCA | GCTTCATCTT | 1350 |
| CACTGAGTTC | CTGGAGCCGG | CAGCCAATGA | GACCGTGCGG | CACGGGTGTC | 1400 |
| TGCGCCTCAA | CCAGCCCACC | CACGTCAACA | ACGGCAACTA | CACGCTGCTG | 1450 |
| GCTGCCAACC | CCTTCGGCCA | GGCCTCCGCC | TCCATCATGG | CTGCCTTCAT | 1500 |
| GGACAACCCT | TTCGAGTTCA | ACCCCGAGGA | CCCCATCCCT | GACACTAACA | 1550 |
| GCACATCTGG | AGACCCGGTG | GAGAAGAAGG | ACGAAACACC | TTTTGGGGTC | 1600 |
| TCGGTGGCTG | TGGGCCTGGC | CGTCTTTGCC | TGCCTCTTCC | TTTCTACGCT | 1650 |
| GCTCCTTGTG | CTCAACAAAT | GTGGACGGAG | AAACAAGTTT | GGGATCAACC | 1700 |
| GCCCGGCTGT | GCTGGCTCCA | GAGGATGGGC | TGGCCATGTC | CCTGCATTTC | 1750 |
| ATGACATTGG | GTGGCAGCTC | CCTGTCCCCC | ACCGAGGGCA | AAGGCTCTGG | 1800 |
| GCTCCAAGGC | CACATCATCG | AGAACCCACA | ATACTTCAGT | GATGCCTGTG | 1850 |
| TTCACCACAT | CAAGCGCCGG | GACATCGTGC | TCAAGTGGGA | GCTGGGGGAG | 1900 |
| GGCGCCTTTG | GGAAGGTCTT | CCTTGCTGAG | TGCCACAACC | TCCTGCCTGA | 1950 |
| GCAGGACAAG | ATGCTGGTGG | CTGTCAAGGC | ACTGAAGGAG | GCGTCCGAGA | 2000 |
| GTGCTCGGCA | GGACTTCCAA | CGTGAGGCTG | AGCTGCTCAC | CATGCTGCAG | 2050 |
| CACCAGCACA | TCGTGCGCTT | CTTCGGCGTC | TGCACCGAGG | CCGCCCCCT | 2100 |
| GCTCATGGTC | TTTGAGTATA | TGCGGCACGG | GGACCTCAAC | CGCTTCCTCC | 2150 |
| GATCCCATGG | ACCTGATGCC | AAGCTGCTGG | CTGGTGGGGA | GGATGTGGCT | 2200 |
| CCAGGCCCCC | TGGGTCTGGG | GCAGCTGCTG | GCCGTGGCTA | GCCAGGTCGC | 2250 |
| TGCGGGGATG | GTGTACCTGG | CGGGTCTGCA | TTTTGTGCAC | CGGGACCTGG | 2300 |
| CCACACGCAA | CTGTCTAGTG | GGCCAGGGAC | TGGTGGTCAA | GATTGGTGAT | 2350 |
| TTTGGCATGA | GCAGGGATAT | CTACAGCACC | GACTATTACC | GTGTGGGAGG | 2400 |

| | | | | |
|---|---|---|---|---|
| CCGCACCATG | CTGCCCATTC | GCTGGATGCC | GCCCGAGAGC | ATCCTGTACC | 2450 |
| GTAAGTTCAC | CACCGAGAGC | GACGTGTGGA | GCTTCGGCGT | GGTGCTCTGG | 2500 |
| GAGATCTTCA | CCTACGGCAA | GCAGCCCTGG | TACCAGCTCT | CCAACACGGA | 2550 |
| GGCAATCGAC | TGCATCACGC | AGGGACGTGA | GTTGGAGCGG | CCACGTGCCT | 2600 |
| GCCCACCAGA | GGTCTACGCC | ATCATGCGGG | CTGCTGGCA | GCGGGAGCCC | 2650 |
| CAGCAACGCC | ACAGCATCAA | GGATGTGCAC | GCCCGGCTGC | AAGCCCTGGC | 2700 |
| CCAGGCACCT | CCTGTCTACC | TGGATGTCCT | GGGCTAGAAT | TAATTCAATC | 2750 |
| GATGGCCGCC | ATGGCCCAAC | TTGTTTATTG | CAGCTTATAA | TGGTTACAAA | 2800 |
| TAAAGCAATA | GCATCACAAA | | | | 2820 |

( 2 ) INFORMATION FOR SEQ ID NO:5:

( i ) SEQUENCE CHARACTERISTICS:
      ( A ) LENGTH: 847 amino acids
      ( B ) TYPE: amino acid
      ( D ) TOPOLOGY: linear ( x i ) SEQUENCE DESCRIPTION: SEQ ID NO:5:

```
Met  Gly  Gly  Thr  Ala  Ala  Arg  Leu  Gly  Ala  Val  Ile  Leu  Phe  Val
 1                  5                   10                      15

Val  Ile  Val  Gly  Leu  His  Gly  Val  Arg  Gly  Lys  Tyr  Ala  Leu  Ala
                    20                  25                      30

Asp  Ala  Ser  Leu  Lys  Met  Ala  Asp  Pro  Asn  Arg  Phe  Arg  Gly  Lys
                    35                  40                      45

Asp  Leu  Pro  Val  Leu  Asp  Gln  Leu  Leu  Glu  Val  Cys  Pro  Thr  Ser
                    50                  55                      60

Cys  Lys  Cys  Ser  Ala  Ser  Arg  Ile  Trp  Cys  Ser  Asp  Pro  Ser  Pro
                    65                  70                      75

Gly  Ile  Val  Ala  Phe  Pro  Arg  Leu  Glu  Pro  Asn  Ser  Val  Asp  Pro
                    80                  85                      90

Glu  Asn  Ile  Thr  Glu  Ile  Phe  Ile  Ala  Asn  Gln  Lys  Arg  Leu  Glu
                    95                  100                     105

Ile  Ile  Asn  Glu  Asp  Asp  Val  Glu  Ala  Tyr  Val  Gly  Leu  Arg  Asn
                    110                 115                     120

Leu  Thr  Ile  Val  Asp  Ser  Gly  Leu  Lys  Phe  Val  Ala  His  Lys  Ala
                    125                 130                     135

Phe  Leu  Lys  Asn  Ser  Asn  Leu  Gln  His  Ile  Asn  Phe  Thr  Arg  Asn
                    140                 145                     150

Lys  Leu  Thr  Ser  Leu  Ser  Arg  Lys  His  Phe  Arg  His  Leu  Asp  Leu
                    155                 160                     165

Ser  Glu  Leu  Ile  Leu  Val  Gly  Asn  Pro  Phe  Thr  Cys  Ser  Cys  Asp
                    170                 175                     180

Ile  Met  Trp  Ile  Lys  Thr  Leu  Gln  Glu  Ala  Lys  Ser  Ser  Pro  Asp
                    185                 190                     195

Thr  Gln  Asp  Leu  Tyr  Cys  Leu  Asn  Glu  Ser  Ser  Lys  Asn  Ile  Pro
                    200                 205                     210

Leu  Ala  Asn  Leu  Gln  Ile  Pro  Asn  Cys  Gly  Leu  Pro  Ser  Ala  Asn
                    215                 220                     225

Leu  Ala  Ala  Pro  Asn  Leu  Thr  Val  Glu  Glu  Gly  Lys  Ser  Ile  Thr
                    230                 235                     240

Leu  Ser  Cys  Ser  Val  Ala  Gly  Asp  Pro  Val  Pro  Asn  Met  Tyr  Trp
                    245                 250                     255
```

```
Asp Val Gly Asn Leu Val Ser Lys His Met Asn Glu Thr Ser His
                260                 265                 270

Thr Gln Gly Ser Leu Arg Ile Thr Asn Ile Ser Ser Asp Asp Ser
                275                 280                 285

Gly Lys Gln Ile Ser Cys Val Ala Glu Asn Leu Val Gly Glu Asp
                290                 295                 300

Gln Asp Ser Val Asn Leu Thr Val His Phe Ala Pro Thr Ile Thr
                305                 310                 315

Phe Leu Glu Ser Pro Thr Ser Asp His His Trp Cys Ile Pro Phe
                320                 325                 330

Thr Val Lys Gly Asn Pro Lys Pro Ala Leu Gln Trp Phe Tyr Asn
                335                 340                 345

Gly Ala Ile Leu Asn Glu Ser Lys Tyr Ile Cys Thr Lys Ile His
                350                 355                 360

Val Thr Asn His Thr Glu Tyr His Gly Cys Leu Gln Leu Asp Asn
                365                 370                 375

Pro Thr His Met Asn Asn Gly Asp Tyr Thr Leu Ile Ala Lys Asn
                380                 385                 390

Glu Tyr Gly Lys Asp Glu Lys Gln Ile Ser Ala His Phe Met Gly
                395                 400                 405

Trp Pro Gly Ile Asp Asp Gly Ala Asn Pro Asn Tyr Pro Asp Val
                410                 415                 420

Ile Tyr Glu Asp Tyr Gly Thr Ala Ala Asn Asp Ile Gly Asp Thr
                425                 430                 435

Thr Asn Arg Ser Asn Glu Ile Pro Ser Thr Asp Val Thr Asp Lys
                440                 445                 450

Thr Gly Arg Glu His Leu Ser Val Tyr Ala Val Val Val Ile Ala
                455                 460                 465

Ser Val Val Gly Phe Cys Leu Leu Val Met Leu Phe Leu Leu Lys
                470                 475                 480

Leu Ala Arg His Ser Lys Phe Gly Met Lys Gly Pro Ala Ser Val
                485                 490                 495

Ile Ser Asn Asp Asp Asp Ser Ala Ser Pro Leu His His Ile Ser
                500                 505                 510

Asn Gly Ser Asn Thr Pro Ser Ser Ser Glu Gly Gly Pro Asp Ala
                515                 520                 525

Val Ile Ile Gly Met Thr Lys Ile Pro Val Ile Glu Asn Pro Gln
                530                 535                 540

Tyr Phe Gly Ile Thr Asn Ser Gln Leu Lys Pro Asp Thr Phe Val
                545                 550                 555

Gln His Ile Lys Arg His Asn Ile Val Leu Lys Arg Glu Leu Gly
                560                 565                 570

Glu Gly Ala Phe Gly Lys Val Phe Leu Ala Glu Cys Tyr Asn Leu
                575                 580                 585

Cys Pro Glu Gln Asp Lys Ile Leu Val Ala Val Lys Thr Leu Lys
                590                 595                 600

Asp Ala Ser Asp Asn Ala Arg Lys Asp Phe His Arg Glu Ala Glu
                605                 610                 615

Leu Leu Thr Asn Leu Gln His Glu His Ile Val Lys Phe Tyr Gly
                620                 625                 630

Val Cys Val Glu Gly Asp Pro Leu Ile Met Val Phe Glu Tyr Met
                635                 640                 645

Lys His Gly Asp Leu Asn Lys Phe Leu Arg Ala His Gly Pro Asp
                650                 655                 660
```

| | | | | | | | | | | | | | | |
|---|---|---|---|---|---|---|---|---|---|---|---|---|---|---|
|Ala|Val|Leu|Met|Ala 665|Glu|Gly|Asn|Pro|Pro 670|Thr|Glu|Leu|Thr|Gln 675|
|Ser|Gln|Met|Leu|His 680|Ile|Ala|Gln|Gln|Ile 685|Ala|Ala|Gly|Met|Val 690|
|Tyr|Leu|Ala|Ser|Gln 695|His|Phe|Val|His|Arg 700|Asp|Leu|Ala|Thr|Arg 705|
|Asn|Cys|Leu|Val|Gly 710|Glu|Asn|Leu|Leu|Val 715|Lys|Ile|Gly|Asp|Phe 720|
|Gly|Met|Ser|Arg|Asp 725|Val|Tyr|Ser|Thr|Asp 730|Tyr|Tyr|Arg|Val|Gly 735|
|Gly|His|Thr|Met|Leu 740|Pro|Ile|Arg|Trp|Met 745|Pro|Pro|Glu|Ser|Ile 750|
|Met|Tyr|Arg|Lys|Phe 755|Thr|Thr|Glu|Ser|Asp 760|Val|Trp|Ser|Leu|Gly 765|
|Val|Val|Leu|Trp|Glu 770|Ile|Phe|Thr|Tyr|Gly 775|Lys|Gln|Pro|Trp|Tyr 780|
|Gln|Leu|Ser|Asn|Asn 785|Glu|Val|Ile|Glu|Cys 790|Ile|Thr|Gln|Gly|Arg 795|
|Val|Leu|Gln|Arg|Pro 800|Arg|Thr|Cys|Pro|Gln 805|Glu|Val|Tyr|Glu|Leu 810|
|Met|Leu|Gly|Cys|Trp 815|Gln|Arg|Glu|Pro|His 820|Met|Arg|Lys|Asn|Ile 825|
|Lys|Gly|Ile|His|Thr 830|Leu|Leu|Gln|Asn|Leu 835|Ala|Lys|Ala|Ser|Pro 840|
|Val|Tyr|Leu|Asp|Ile 845|Leu|Gly 847| | | | | | | | |

( 2 ) INFORMATION FOR SEQ ID NO:6:

( i ) SEQUENCE CHARACTERISTICS:
        ( A ) LENGTH: 3060 bases
        ( B ) TYPE: nucleic acid
        ( C ) STRANDEDNESS: double
        ( D ) TOPOLOGY: linear ( x i ) SEQUENCE DESCRIPTION: SEQ ID NO:6:

```
TATAGAATAA   CATCCACTTT   GCCTTTCTCT   CCACAGGTGT   CCACTCCCAG        50

GTCCAACTGC   ACCTCGGTTC   TATCGATTGA   ATTCCACTGC   CTTCCACCAA       100

GCTCTGCAGG   ATCCAGAGT    CAGGGGTCTG   TATCTTCCTG   CTGGTGGCTC       150

CAGTTCAGGA   ACAGTAAACC   CTGCTCCGAA   TATTGCCTCT   CACATCTCGT       200

CAATCTCCGC   GAGGACTGGG   GACCCTGTGA   CAAGCTTCAG   CGCGAACGAC       250

CAACTACCCC   GATCATCAGT   TATCCTTAAG   GTCTCTTTTG   TGTGGTGCGT       300

TCCGGTATGG   GGGGGACTGC   CGCCAGGTTG   GGGGCCGTGA   TTTTGTTTGT       350

CGTCATAGTG   GGCCTCCATG   GGGTCCGCGG   CAAATATGCC   TTGGCGGATG       400

CCTCTCTCAA   GATGGCCGAC   CCCAATCGAT   TTCGCGGCAA   AGACCTTCCG       450

GTCCTGGACC   AGCTGCTCGA   GGTATGTCCC   ACGTCCTGCA   AATGCAGTGC       500

CTCTCGGATC   TGGTGCAGCG   ACCCTTCTCC   TGGCATCGTG   GCATTTCCGA       550

GATTGGAGCC   TAACAGTGTA   GATCCTGAGA   ACATCACCGA   AATTTTCATC       600

GCAAACCAGA   AAAGGTTAGA   AATCATCAAC   GAAGATGATG   TTGAAGCTTA       650

TGTGGGACTG   AGAAATCTGA   CAATTGTGGA   TTCTGGATTA   AAATTTGTGG       700

CTCATAAAGC   ATTTCTGAAA   AACAGCAACC   TGCAGCACAT   CAATTTTACC       750
```

| | | | | | |
|---|---|---|---|---|---|
| CGAAACAAAC | TGACGAGTTT | GTCTAGGAAA | CATTTCCGTC | ACCTTGACTT | 800 |
| GTCTGAACTG | ATCCTGGTGG | GCAATCCATT | TACATGCTCC | TGTGACATTA | 850 |
| TGTGGATCAA | GACTCTCCAA | GAGGCTAAAT | CCAGTCCAGA | CACTCAGGAT | 900 |
| TTGTACTGCC | TGAATGAAAG | CAGCAAGAAT | ATTCCCCTGG | CAAACCTGCA | 950 |
| GATACCCAAT | TGTGGTTTGC | CATCTGCAAA | TCTGGCCGCA | CCTAACCTCA | 1000 |
| CTGTGGAGGA | AGGAAAGTCT | ATCACATTAT | CCTGTAGTGT | GGCAGGTGAT | 1050 |
| CCGGTTCCTA | ATATGTATTG | GGATGTTGGT | AACCTGGTTT | CCAAACATAT | 1100 |
| GAATGAAACA | AGCCACACAC | AGGGCTCCTT | AAGGATAACT | AACATTTCAT | 1150 |
| CCGATGACAG | TGGGAAGCAG | ATCTCTTGTG | TGGCGGAAAA | TCTTGTAGGA | 1200 |
| GAAGATCAAG | ATTCTGTCAA | CCTCACTGTG | CATTTTGCAC | CAACTATCAC | 1250 |
| ATTTCTCGAA | TCTCCAACCT | CAGACCACCA | CTGGTGCATT | CCATTCACTG | 1300 |
| TGAAAGGCAA | CCCAAAACCA | GCGCTTCAGT | GGTTCTATAA | CGGGGCAATA | 1350 |
| TTGAATGAGT | CCAAATACAT | CTGTACTAAA | ATACATGTTA | CCAATCACAC | 1400 |
| GGAGTACCAC | GGCTGCCTCC | AGCTGGATAA | TCCCACTCAC | ATGAACAATG | 1450 |
| GGGACTACAC | TCTAATAGCC | AAGAATGAGT | ATGGGAAGGA | TGAGAAACAG | 1500 |
| ATTTCTGCTC | ACTTCATGGG | CTGGCCTGGA | ATTGACGATG | GTGCAAACCC | 1550 |
| AAATTATCCT | GATGTAATTT | ATGAAGATTA | TGGAACTGCA | GCGAATGACA | 1600 |
| TCGGGGACAC | CACGAACAGA | AGTAATGAAA | TCCCTTCCAC | AGACGTCACT | 1650 |
| GATAAACCG | GTCGGGAACA | TCTCTCGGTC | TATGCTGTGG | TGGTGATTGC | 1700 |
| GTCTGTGGTG | GGATTTTGCC | TTTTGGTAAT | GCTGTTTCTG | CTTAAGTTGG | 1750 |
| CAAGACACTC | CAAGTTTGGC | ATGAAAGGCC | CAGCCTCCGT | TATCAGCAAT | 1800 |
| GATGATGACT | CTGCCAGCCC | ACTCCATCAC | ATCTCCAATG | GGAGTAACAC | 1850 |
| TCCATCTTCT | TCGGAAGGTG | GCCCAGATGC | TGTCATTATT | GGAATGACCA | 1900 |
| AGATCCCTGT | CATTGAAAAT | CCCCAGTACT | TTGGCATCAC | CAACAGTCAG | 1950 |
| CTCAAGCCAG | ACACATTTGT | TCAGCACATC | AAGCGACATA | ACATTGTTCT | 2000 |
| GAAAAGGGAG | CTAGGCGAAG | GAGCCTTTGG | AAAAGTGTTC | CTAGCTGAAT | 2050 |
| GCTATAACCT | CTGTCCTGAG | CAGGACAAGA | TCTTGGTGGC | AGTGAAGACC | 2100 |
| CTGAAGGATG | CCAGTGACAA | TGCACGCAAG | GACTTCCACC | GTGAGGCCGA | 2150 |
| GCTCCTGACC | AACCTCCAGC | ATGAGCACAT | CGTCAAGTTC | TATGGCGTCT | 2200 |
| GCGTGGAGGG | CGACCCCCTC | ATCATGGTCT | TTGAGTACAT | GAAGCATGGG | 2250 |
| GACCTCAACA | AGTTCCTCAG | GGCACACGGC | CCTGATGCCG | TGCTGATGGC | 2300 |
| TGAGGGCAAC | CCGCCCACGG | AACTGACGCA | GTCGCAGATG | CTGCATATAG | 2350 |
| CCCAGCAGAT | CGCCGCGGGC | ATGGTCTACC | TGGCGTCCCA | GCACTTCGTG | 2400 |
| CACCGCGATT | TGGCCACCAG | GAACTGCCTG | GTCGGGGAGA | ACTTGCTGGT | 2450 |
| GAAAATCGGG | GACTTTGGGA | TGTCCCGGGA | CGTGTACAGC | ACTGACTACT | 2500 |
| ACAGGGTCGG | TGGCCACACA | ATGCTGCCCA | TTCGCTGGAT | GCCTCCAGAG | 2550 |
| AGCATCATGT | ACAGGAAATT | CACGACGGAA | AGCGACGTCT | GGAGCCTGGG | 2600 |
| GGTCGTGTTG | TGGGAGATTT | TCACCTATGG | CAAACAGCCC | TGGTACCAGC | 2650 |
| TGTCAAACAA | TGAGGTGATA | GAGTGTATCA | CTCAGGGCCG | AGTCCTGCAG | 2700 |
| CGACCCCGCA | CGTGCCCCCA | GGAGGTGTAT | GAGCTGATGC | TGGGGTGCTG | 2750 |

| GCAGCGAGAG | CCCCACATGA | GGAAGAACAT | CAAGGGCATC | CATACCCTCC | 2800 |
| TTCAGAACTT | GGCCAAGGCA | TCTCCGGTCT | ACCTGGACAT | TCTAGGCTAG | 2850 |
| GGCCCTTTTC | CCCAGACCGA | TCCTTCCCAA | CGTACTCCTC | AGACGGGCTG | 2900 |
| AGAGGATGAA | CATCTTTTAA | CTGCCGCTGG | AGGCCACCAA | GCTGCTCTCC | 2950 |
| TTCACTCTGA | CAGTATTAAC | ATCAAAGACT | CCGAGAAGCT | CTCGACCTGC | 3000 |
| AGAAGCTTGG | CCGCCATGGC | CCAACTTGTT | TATTGCAGCT | TATAATGGTT | 3050 |
| ACAAATAAAG | | | | | 3060 |

( 2 ) INFORMATION FOR SEQ ID NO:7:

( i ) SEQUENCE CHARACTERISTICS:
        ( A ) LENGTH: 850 amino acids
        ( B ) TYPE: amino acid
        ( D ) TOPOLOGY: linear ( x i ) SEQUENCE DESCRIPTION: SEQ ID NO:7:

```
Met Gly Gly Thr Ala Ala Arg Leu Gly Ala Val Ile Leu Phe Val
  1               5                  10                  15

Val Ile Val Gly Leu His Gly Val Arg Gly Lys Tyr Ala Leu Ala
                 20                  25                  30

Asp Ala Ser Leu Lys Met Ala Asp Pro Asn Arg Phe Arg Gly Lys
                 35                  40                  45

Asp Leu Pro Val Leu Asp Gln Leu Leu Glu Val Cys Pro Ala Asn
                 50                  55                  60

Cys Val Cys Ser Lys Thr Glu Ile Asn Cys Arg Arg Pro Asp Asp
                 65                  70                  75

Gly Asn Leu Phe Pro Leu Leu Glu Gly Gln Asp Ser Gly Asn Ser
                 80                  85                  90

Asn Gly Asn Ala Asn Ile Asn Ile Thr Asp Ile Ser Arg Asn Ile
                 95                 100                 105

Thr Ser Ile His Ile Glu Asn Trp Arg Ser Leu His Thr Leu Asn
                110                 115                 120

Ala Val Asp Met Glu Leu Tyr Thr Gly Leu Gln Lys Leu Thr Ile
                125                 130                 135

Lys Asn Ser Gly Leu Arg Ser Ile Gln Pro Arg Ala Phe Ala Lys
                140                 145                 150

Asn Pro His Leu Arg Tyr Ile Asn Leu Ser Ser Asn Arg Leu Thr
                155                 160                 165

Thr Leu Ser Trp Gln Leu Phe Gln Thr Leu Ser Leu Arg Glu Leu
                170                 175                 180

Gln Leu Glu Gln Asn Phe Phe Asn Cys Ser Cys Asp Ile Arg Trp
                185                 190                 195

Met Gln Leu Trp Gln Glu Gln Gly Glu Ala Lys Leu Asn Ser Gln
                200                 205                 210

Asn Leu Tyr Cys Ile Asn Ala Asp Gly Ser Gln Leu Pro Leu Phe
                215                 220                 225

Arg Met Asn Ile Ser Gln Cys Asp Leu Pro Glu Ile Ser Val Ser
                230                 235                 240

His Val Asn Leu Thr Val Arg Glu Gly Asp Asn Ala Val Ile Thr
                245                 250                 255

Cys Asn Gly Ser Gly Ser Pro Leu Pro Asp Val Asp Trp Ile Val
                260                 265                 270

Thr Gly Leu Gln Ser Ile Asn Thr His Gln Thr Asn Leu Asn Trp
```

|     |     |     |     | 275 |     |     |     | 280 |     |     |     | 285 |
| --- | --- | --- | --- | --- | --- | --- | --- | --- | --- | --- | --- | --- |
| Thr | Asn | Val | His | Ala | Ile | Asn | Leu | Thr | Leu | Val | Asn | Val | Thr | Ser |
|     |     |     |     | 290 |     |     |     | 295 |     |     |     | 300 |
| Glu | Asp | Asn | Gly | Phe | Thr | Leu | Thr | Cys | Ile | Ala | Glu | Asn | Val | Val |
|     |     |     |     | 305 |     |     |     | 310 |     |     |     | 315 |
| Gly | Met | Ser | Asn | Ala | Ser | Val | Ala | Leu | Thr | Val | Tyr | Tyr | Pro | Pro |
|     |     |     |     | 320 |     |     |     | 325 |     |     |     | 330 |
| Arg | Val | Val | Ser | Leu | Glu | Glu | Pro | Glu | Leu | Arg | Leu | Glu | His | Cys |
|     |     |     |     | 335 |     |     |     | 340 |     |     |     | 345 |
| Ile | Glu | Phe | Val | Val | Arg | Gly | Asn | Pro | Pro | Pro | Thr | Leu | His | Trp |
|     |     |     |     | 350 |     |     |     | 355 |     |     |     | 360 |
| Leu | His | Asn | Gly | Gln | Pro | Leu | Arg | Glu | Ser | Lys | Ile | Ile | His | Val |
|     |     |     |     | 365 |     |     |     | 370 |     |     |     | 375 |
| Glu | Tyr | Tyr | Gln | Glu | Gly | Glu | Ile | Ser | Glu | Gly | Cys | Leu | Leu | Phe |
|     |     |     |     | 380 |     |     |     | 385 |     |     |     | 390 |
| Asn | Lys | Pro | Thr | His | Tyr | Asn | Asn | Gly | Asn | Tyr | Thr | Leu | Ile | Ala |
|     |     |     |     | 395 |     |     |     | 400 |     |     |     | 405 |
| Lys | Asn | Pro | Leu | Gly | Thr | Ala | Asn | Gln | Thr | Ile | Asn | Gly | His | Phe |
|     |     |     |     | 410 |     |     |     | 415 |     |     |     | 420 |
| Leu | Lys | Glu | Pro | Phe | Pro | Glu | Ser | Thr | Asp | Asn | Phe | Ile | Leu | Phe |
|     |     |     |     | 425 |     |     |     | 430 |     |     |     | 435 |
| Asp | Glu | Val | Ser | Pro | Thr | Pro | Pro | Ile | Thr | Val | Thr | His | Lys | Pro |
|     |     |     |     | 440 |     |     |     | 445 |     |     |     | 450 |
| Glu | Glu | Asp | Thr | Phe | Gly | Val | Ser | Ile | Ala | Val | Gly | Leu | Ala | Ala |
|     |     |     |     | 455 |     |     |     | 460 |     |     |     | 465 |
| Phe | Ala | Cys | Val | Leu | Leu | Val | Val | Leu | Phe | Val | Met | Ile | Asn | Lys |
|     |     |     |     | 470 |     |     |     | 475 |     |     |     | 480 |
| Tyr | Gly | Arg | Arg | Ser | Lys | Phe | Gly | Met | Lys | Gly | Pro | Val | Ala | Val |
|     |     |     |     | 485 |     |     |     | 490 |     |     |     | 495 |
| Ile | Ser | Gly | Glu | Glu | Asp | Ser | Ala | Ser | Pro | Leu | His | His | Ile | Asn |
|     |     |     |     | 500 |     |     |     | 505 |     |     |     | 510 |
| His | Gly | Ile | Thr | Thr | Pro | Ser | Ser | Leu | Asp | Ala | Gly | Pro | Asp | Thr |
|     |     |     |     | 515 |     |     |     | 520 |     |     |     | 525 |
| Val | Val | Ile | Gly | Met | Thr | Arg | Ile | Pro | Val | Ile | Glu | Asn | Pro | Gln |
|     |     |     |     | 530 |     |     |     | 535 |     |     |     | 540 |
| Tyr | Phe | Arg | Gln | Gly | His | Asn | Cys | His | Lys | Pro | Asp | Thr | Tyr | Val |
|     |     |     |     | 545 |     |     |     | 550 |     |     |     | 555 |
| Gln | His | Ile | Lys | Arg | Arg | Asp | Ile | Val | Leu | Lys | Arg | Glu | Leu | Gly |
|     |     |     |     | 560 |     |     |     | 565 |     |     |     | 570 |
| Glu | Gly | Ala | Phe | Gly | Lys | Val | Phe | Leu | Ala | Glu | Cys | Tyr | Asn | Leu |
|     |     |     |     | 575 |     |     |     | 580 |     |     |     | 585 |
| Ser | Pro | Thr | Lys | Asp | Lys | Met | Leu | Val | Ala | Val | Lys | Ala | Leu | Lys |
|     |     |     |     | 590 |     |     |     | 595 |     |     |     | 600 |
| Asp | Pro | Thr | Leu | Ala | Ala | Arg | Lys | Asp | Phe | Gln | Arg | Glu | Ala | Glu |
|     |     |     |     | 605 |     |     |     | 610 |     |     |     | 615 |
| Leu | Leu | Thr | Asn | Leu | Gln | His | Glu | His | Ile | Val | Lys | Phe | Tyr | Gly |
|     |     |     |     | 620 |     |     |     | 625 |     |     |     | 630 |
| Val | Cys | Gly | Asp | Gly | Asp | Pro | Leu | Ile | Met | Val | Phe | Glu | Tyr | Met |
|     |     |     |     | 635 |     |     |     | 640 |     |     |     | 645 |
| Lys | His | Gly | Asp | Leu | Asn | Lys | Phe | Leu | Arg | Ala | His | Gly | Pro | Asp |
|     |     |     |     | 650 |     |     |     | 655 |     |     |     | 660 |
| Ala | Met | Ile | Leu | Val | Asp | Gly | Gln | Pro | Arg | Gln | Ala | Lys | Gly | Glu |
|     |     |     |     | 665 |     |     |     | 670 |     |     |     | 675 |

| | | | | | | | | | | | | | | |
|---|---|---|---|---|---|---|---|---|---|---|---|---|---|---|
|Leu|Gly|Leu|Ser|Gln<br>680|Met|Leu|His|Ile|Ala<br>685|Ser|Gln|Ile|Ala|Ser<br>690|
|Gly|Met|Val|Tyr|Leu<br>695|Ala|Ser|Gln|His|Phe<br>700|Val|His|Arg|Asp|Leu<br>705|
|Ala|Thr|Arg|Asn|Cys<br>710|Leu|Val|Gly|Ala|Asn<br>715|Leu|Leu|Val|Lys|Ile<br>720|
|Gly|Asp|Phe|Gly|Met<br>725|Ser|Arg|Asp|Val|Tyr<br>730|Ser|Thr|Asp|Tyr|Tyr<br>735|
|Arg|Val|Gly|Gly|His<br>740|Thr|Met|Leu|Pro|Ile<br>745|Arg|Trp|Met|Pro|Pro<br>750|
|Glu|Ser|Ile|Met|Tyr<br>755|Arg|Lys|Phe|Thr|Thr<br>760|Glu|Ser|Asp|Val|Trp<br>765|
|Ser|Phe|Gly|Val|Ile<br>770|Leu|Trp|Glu|Ile|Phe<br>775|Thr|Tyr|Gly|Lys|Gln<br>780|
|Pro|Trp|Phe|Gln|Leu<br>785|Ser|Asn|Thr|Glu|Val<br>790|Ile|Glu|Cys|Ile|Thr<br>795|
|Gln|Gly|Arg|Val|Leu<br>800|Glu|Arg|Pro|Arg|Val<br>805|Cys|Pro|Lys|Glu|Val<br>810|
|Tyr|Asp|Val|Met|Leu<br>815|Gly|Cys|Trp|Gln|Arg<br>820|Glu|Pro|Gln|Gln|Arg<br>825|
|Leu|Asn|Ile|Lys|Glu<br>830|Ile|Tyr|Lys|Ile|Leu<br>835|His|Ala|Leu|Gly|Lys<br>840|
|Ala|Thr|Pro|Ile|Tyr<br>845|Leu|Asp|Ile|Leu|Gly<br>850| | | | | |

(2) INFORMATION FOR SEQ ID NO:8:

(i) SEQUENCE CHARACTERISTICS:
        (A) LENGTH: 2940 bases
        (B) TYPE: nucleic acid
        (C) STRANDEDNESS: double
        (D) TOPOLOGY: linear (xi) SEQUENCE DESCRIPTION: SEQ ID NO:8:

```
TATAGAATAA  CATCCACTTT  GCCTTTCTCT  CCACAGGTGT  CCACTCCCAG           50
GTCCAACTGC  ACCTGAATTC  CACTGCCTTC  CACCAAGCTC  TGCAGGATCC          100
CAGAGTCAGG  GGTCTGTATC  TTCCTGCTGG  TGGCTCCAGT  TCAGGAACAG          150
TAAACCCTGC  TCCGAATATT  GCCTCTCACA  TCTCGTCAAT  CTCCGCGAGG          200
ACTGGGGACC  CTGTGACAAG  CTTCAGCGCG  AACGACCAAC  TACCCCGATC          250
ATCAGTTATC  CTTAAGGTCT  CTTTTGTGTG  GTGCGTTCCG  GTATGGGGGG          300
GACTGCCGCC  AGGTTGGGGG  CCGTGATTTT  GTTTGTCGTC  ATAGTGGGCC          350
TCCATGGGGT  CCGCGGCAAA  TATGCCTTGG  CGGATGCCTC  TCTCAAGATG          400
GCCGACCCCA  ATCGATTTCG  CGGCAAAGAC  CTTCCGGTCC  TGGACCAGCT          450
GCTCGAGGTA  TGCCCTGCAA  ATTGTGTCTG  CAGCAAGACT  GAGATCAATT          500
GCCGGCGGCC  GGACGATGGG  AACCTCTTCC  CCCTCCTGGA  AGGGCAGGAT          550
TCAGGGAACA  GCAATGGGAA  CGCCAATATC  AACATCACGG  ACATCTCAAG          600
GAATATCACT  TCCATACACA  TAGAGAACTG  GCGCAGTCTT  CACACGCTCA          650
ACGCCGTGGA  CATGGAGCTC  TACACCGGAC  TTCAAAAGCT  GACCATCAAG          700
AACTCAGGAC  TTCGGAGCAT  TCAGCCAGA  GCCTTTGCCA  AGAACCCCCA           750
TTTGCGTTAT  ATAAACCTGT  CAAGTAACCG  GCTCACCACA  CTCTCGTGGC          800
AGCTCTTCCA  GACGCTGAGT  CTTCGGGAAT  TGCAGTTGGA  GCAGAACTTT          850
```

| | | | | | |
|---|---|---|---|---|---|
| TTCAACTGCA | GCTGTGACAT | CCGCTGGATG | CAGCTCTGGC | AGGAGCAGGG | 900 |
| GGAGGCCAAG | CTCAACAGCC | AGAACCTCTA | CTGCATCAAT | GCTGATGGCT | 950 |
| CCCAGCTTCC | TCTCTTCCGC | ATGAACATCA | GTCAGTGTGA | CCTTCCTGAG | 1000 |
| ATCAGCGTGA | GCCACGTCAA | CCTGACCGTA | CGAGAGGGTG | ACAATGCTGT | 1050 |
| TATCACTTGC | AATGGCTCTG | GATCACCCCT | TCCTGATGTG | GACTGGATAG | 1100 |
| TCACTGGGCT | GCAGTCCATC | AACACTCACC | AGACCAATCT | GAACTGGACC | 1150 |
| AATGTTCATG | CCATCAACTT | GACGCTGGTG | AATGTGACGA | GTGAGGACAA | 1200 |
| TGGCTTCACC | CTGACGTGCA | TTGCAGAGAA | CGTGGTGGGC | ATGAGCAATG | 1250 |
| CCAGTGTTGC | CCTCACTGTC | TACTATCCCC | CACGTGTGGT | GAGCCTGGAG | 1300 |
| GAGCCTGAGC | TGCGCCTGGA | GCACTGCATC | GAGTTTGTGG | TGCGTGGCAA | 1350 |
| CCCCCCACCA | ACGCTGCACT | GGCTGCACAA | TGGGCAGCCT | CTGCGGGAGT | 1400 |
| CCAAGATCAT | CCATGTGGAA | TACTACCAAG | AGGGAGAGAT | TTCCGAGGGC | 1450 |
| TGCCTGCTCT | TCAACAAGCC | CACCCACTAC | AACAATGGCA | ACTATACCCT | 1500 |
| CATTGCCAAA | AACCCACTGG | GCACAGCCAA | CCAGACCATC | AATGGCCACT | 1550 |
| TCCTCAAGGA | GCCCTTTCCA | GAGAGCACGG | ATAACTTTAT | CTTGTTTGAC | 1600 |
| GAAGTGAGTC | CCACACCTCC | TATCACTGTG | ACCCACAAAC | CAGAAGAAGA | 1650 |
| CACTTTTGGG | GTATCCATAG | CAGTTGGACT | TGCTGCTTTT | GCCTGTGTCC | 1700 |
| TGTTGGTGGT | TCTCTTCGTC | ATGATCAACA | AATATGGTCG | ACGGTCCAAA | 1750 |
| TTTGGAATGA | AGGGTCCCGT | GGCTGTCATC | AGTGGTGAGG | AGGACTCAGC | 1800 |
| CAGCCCACTG | CACCACATCA | ACCACGGCAT | CACCACGCCC | TCGTCACTGG | 1850 |
| ATGCCGGGCC | CGACACTGTG | GTCATTGGCA | TGACTCGCAT | CCCTGTCATT | 1900 |
| GAGAACCCCC | AGTACTTCCG | TCAGGGACAC | AACTGCCACA | AGCCGGACAC | 1950 |
| GTATGTGCAG | CACATTAAGA | GGAGAGACAT | CGTGCTGAAG | CGAGAACTGG | 2000 |
| GTGAGGGAGC | CTTTGGAAAG | GTCTTCCTGG | CCGAGTGCTA | CAACCTCAGC | 2050 |
| CCGACCAAGG | ACAAGATGCT | TGTGGCTGTG | AAGGCCCTGA | AGGATCCCAC | 2100 |
| CCTGGCTGCC | CGGAAGGATT | TCCAGAGGGA | GGCCGAGCTG | CTCACCAACC | 2150 |
| TGCAGCATGA | GCACATTGTC | AAGTTCTATG | GAGTGTGCGG | CGATGGGGAC | 2200 |
| CCCCTCATCA | TGGTCTTTGA | ATACATGAAG | CATGGAGACC | TGAATAAGTT | 2250 |
| CCTCAGGGCC | CATGGGCCAG | ATGCAATGAT | CCTTGTGGAT | GGACAGCCAC | 2300 |
| GCCAGGCCAA | GGGTGAGCTG | GGGCTCTCCC | AAATGCTCCA | CATTGCCAGT | 2350 |
| CAGATCGCCT | CGGGTATGGT | GTACCTGGCC | TCCCAGCACT | TTGTGCACCG | 2400 |
| AGACCTGGCC | ACCAGGAACT | GCCTGGTTGG | AGCGAATCTG | CTAGTGAAGA | 2450 |
| TTGGGGACTT | CGGCATGTCC | AGAGATGTCT | ACAGCACGGA | TTATTACAGG | 2500 |
| GTGGAGGAC | ACACCATGCT | CCCCATTCGC | TGGATGCCTC | CTGAAAGCAT | 2550 |
| CATGTACCGG | AAGTTCACTA | CAGAGAGTGA | TGTATGGAGC | TTCGGGGTGA | 2600 |
| TCCTCTGGGA | GATCTTCACC | TATGGAAAGC | AGCCATGGTT | CCAACTCTCA | 2650 |
| AACACGGAGG | TCATTGAGTG | CATTACCCAA | GGTCGTGTTT | TGGAGCGGCC | 2700 |
| CCGAGTCTGC | CCCAAAGAGG | TGTACGATGT | CATGCTGGGG | TGCTGGCAGA | 2750 |
| GGGAACCACA | GCAGCGGTTG | AACATCAAGG | AGATCTACAA | AATCCTCCAT | 2800 |
| GCTTTGGGGA | AGGCCACCCC | AATCTACCTG | GACATTCTTG | GCTAGTGGTG | 2850 |

| | | | | | |
|---|---|---|---|---|---|
| GCTGGTGGTC | ATGAATTAAT | TCAATCGATG | GCCGCCATGG | CCCAACTTGT | 2900 |
| TTATTGCAGC | TTATAATGGT | TACAAATAAA | GCAATAGCAT | | 2940 |

( 2 ) INFORMATION FOR SEQ ID NO:9:

( i ) SEQUENCE CHARACTERISTICS:
    ( A ) LENGTH: 5141 bases
    ( B ) TYPE: nucleic acid
    ( C ) STRANDEDNESS: double
    ( D ) TOPOLOGY: linear ( x i ) SEQUENCE DESCRIPTION: SEQ ID NO:9:

| | | | | | |
|---|---|---|---|---|---|
| TTCGAGCTCG | CCCGACATTG | ATTATTGACT | AGAGTCGATC | GACAGCTGTG | 50 |
| GAATGTGTGT | CAGTTAGGGT | GTGGAAAGTC | CCCAGGCTCC | CCAGCAGGCA | 100 |
| GAAGTATGCA | AAGCATGCAT | CTCAATTAGT | CAGCAACCAG | GTGTGGAAAG | 150 |
| TCCCCAGGCT | CCCCAGCAGG | CAGAAGTATG | CAAAGCATGC | ATCTCAATTA | 200 |
| GTCAGCAACC | ATAGTCCCGC | CCCTAACTCC | GCCCATCCCG | CCCCTAACTC | 250 |
| CGCCCAGTTC | CGCCCATTCT | CCGCCCCATG | GCTGACTAAT | TTTTTTTATT | 300 |
| TATGCAGAGG | CCGAGGCCGC | CTCGGCCTCT | GAGCTATTCC | AGAAGTAGTG | 350 |
| AGGAGGCTTT | TTTGGAGGCC | TAGGCTTTTG | CAAAAAGCTA | GCTTATCCGG | 400 |
| CCGGGAACGG | TGCATTGGAA | CGCGGATTCC | CCGTGCCAAG | AGTGACGTAA | 450 |
| GTACCGCCTA | TAGAGCGATA | AGAGGATTTT | ATCCCCGCTG | CCATCATGGT | 500 |
| TCGACCATTG | AACTGCATCG | TCGCCGTGTC | CCAAAATATG | GGGATTGGCA | 550 |
| AGAACGGAGA | CCTACCCTGG | CCTCCGCTCA | GGAACGAGTT | CAAGTACTTC | 600 |
| CAAAGAATGA | CCACAACCTC | TTCAGTGGAA | GGTAAACAGA | ATCTGGTGAT | 650 |
| TATGGGTAGG | AAAACCTGGT | TCTCCATTCC | TGAGAAGAAT | CGACCTTTAA | 700 |
| AGGACAGAAT | TAATATAGTT | CTCAGTAGAG | AACTCAAAGA | ACCACCACGA | 750 |
| GGAGCTCATT | TTCTTGCCAA | AAGTTTGGAT | GATGCCTTAA | GACTTATTGA | 800 |
| ACAACCGGAA | TTGGCAAGTA | AAGTAGACAT | GGTTTGGATA | GTCGGAGGCA | 850 |
| GTTCTGTTTA | CCAGGAAGCC | ATGAATCAAC | CAGGCCACCT | TAGACTCTTT | 900 |
| GTGACAAGGA | TCATGCAGGA | ATTTGAAAGT | GACACGTTTT | TCCCAGAAAT | 950 |
| TGATTTGGGG | AAATATAAAC | CTCTCCCAGA | ATACCCAGGC | GTCCTCTCTG | 1000 |
| AGGTCCAGGA | GGAAAAAGGC | ATCAAGTATA | AGTTTGAAGT | CTACGAGAAG | 1050 |
| AAAGACTAAC | AGGAAGATGC | TTTCAAGTTC | TCTGCTCCCC | TCCTAAAGCT | 1100 |
| ATGCATTTTT | ATAAGACCAT | GGGACTTTTG | CTGGCTTTAG | ATCCCCTTGG | 1150 |
| CTTCGTTAGA | ACGCGGCTAC | AATTAATACA | TAACCTTATG | TATCATACAC | 1200 |
| ATACGATTTA | GGTGACACTA | TAGATAACAT | CCACTTTGCC | TTTCTCTCCA | 1250 |
| CAGGTGTCCA | CTCCCAGGTC | CAACTGCACC | TCGGTTCTAA | GCTTCTGCAG | 1300 |
| GTCGACTCTA | GAGGATCCCC | GGGGAATTCA | ATCGATGGCC | GCCATGGCCC | 1350 |
| AACTTGTTTA | TTGCAGCTTA | TAATGGTTAC | AAATAAAGCA | ATAGCATCAC | 1400 |
| AAATTTCACA | AATAAAGCAT | TTTTTCACT | GCATTCTAGT | TGTGGTTTGT | 1450 |
| CCAAACTCAT | CAATGTATCT | TATCATGTCT | GGATCGATCG | GGAATTAATT | 1500 |
| CGGCGCAGCA | CCATGGCCTG | AAATAACCTC | TGAAAGAGGA | ACTTGGTTAG | 1550 |
| GTACCTTCTG | AGGCGGAAAG | AACCAGCTGT | GGAATGTGTG | TCAGTTAGGG | 1600 |

```
TGTGGAAAGT  CCCCAGGCTC  CCCAGCAGGC  AGAAGTATGC  AAAGCATGCA      1650
TCTCAATTAG  TCAGCAACCA  GGTGTGGAAA  GTCCCCAGGC  TCCCCAGCAG      1700
GCAGAAGTAT  GCAAAGCATG  CATCTCAATT  AGTCAGCAAC  CATAGTCCCG      1750
CCCCTAACTC  CGCCCATCCC  GCCCCTAACT  CCGCCCAGTT  CCGCCCATTC      1800
TCCGCCCCAT  GGCTGACTAA  TTTTTTTTAT  TTATGCAGAG  GCCGAGGCCG      1850
CCTCGGCCTC  TGAGCTATTC  CAGAAGTAGT  GAGGAGGCTT  TTTTGGAGGC      1900
CTAGGCTTTT  GCAAAAAGCT  GTTACCTCGA  GCGGCCGCTT  AATTAAGGCG      1950
CGCCATTTAA  ATCCTGCAGG  TAACAGCTTG  GCACTGGCCG  TCGTTTTACA      2000
ACGTCGTGAC  TGGGAAAACC  CTGGCGTTAC  CCAACTTAAT  CGCCTTGCAG      2050
CACATCCCCC  CTTCGCCAGC  TGGCGTAATA  GCGAAGAGGC  CCGCACCGAT      2100
CGCCCTTCCC  AACAGTTGCG  TAGCCTGAAT  GGCGAATGGC  GCCTGATGCG      2150
GTATTTTCTC  CTTACGCATC  TGTGCGGTAT  TTCACACCGC  ATACGTCAAA      2200
GCAACCATAG  TACGCGCCCT  GTAGCGGCGC  ATTAAGCGCG  GCGGGTGTGG      2250
TGGTTACGCG  CAGCGTGACC  GCTACACTTG  CCAGCGCCCT  AGCGCCCGCT      2300
CCTTTCGCTT  TCTTCCCTTC  CTTTCTCGCC  ACGTTCGCCG  GCTTTCCCCG      2350
TCAAGCTCTA  AATCGGGGGC  TCCCTTTAGG  GTTCCGATTT  AGTGCTTTAC      2400
GGCACCTCGA  CCCCAAAAAA  CTTGATTTGG  GTGATGGTTC  ACGTAGTGGG      2450
CCATCGCCCT  GATAGACGGT  TTTTCGCCCT  TTGACGTTGG  AGTCCACGTT      2500
CTTTAATAGT  GGACTCTTGT  TCCAAACTGG  AACAACACTC  AACCCTATCT      2550
CGGGCTATTC  TTTTGATTTA  TAAGGGATTT  TGCCGATTTC  GGCCTATTGG      2600
TTAAAAAATG  AGCTGATTTA  ACAAAAATTT  AACGCGAATT  TTAACAAAAT      2650
ATTAACGTTT  ACAATTTTAT  GGTGCACTCT  CAGTACAATC  TGCTCTGATG      2700
CCGCATAGTT  AAGCCAACTC  CGCTATCGCT  ACGTGACTGG  GTCATGGCTG      2750
CGCCCCGACA  CCCGCCAACA  CCCGCTGACG  CGCCCTGACG  GGCTTGTCTG      2800
CTCCCGGCAT  CCGCTTACAG  ACAAGCTGTG  ACCGTCTCCG  GGAGCTGCAT      2850
GTGTCAGAGG  TTTTCACCGT  CATCACCGAA  ACGCGCGAGG  CAGTATTCTT      2900
GAAGACGAAA  GGGCCTCGTG  ATACGCCTAT  TTTTATAGGT  TAATGTCATG      2950
ATAATAATGG  TTTCTTAGAC  GTCAGGTGGC  ACTTTTCGGG  GAAATGTGCG      3000
CGGAACCCCT  ATTTGTTTAT  TTTTCTAAAT  ACATTCAAAT  ATGTATCCGC      3050
TCATGAGACA  ATAACCCTGA  TAAATGCTTC  AATAATATTG  AAAAAGGAAG      3100
AGTATGAGTA  TTCAACATTT  CCGTGTCGCC  CTTATTCCCT  TTTTTGCGGC      3150
ATTTTGCCTT  CCTGTTTTTG  CTCACCCAGA  AACGCTGGTG  AAAGTAAAAG      3200
ATGCTGAAGA  TCAGTTGGGT  GCACGAGTGG  GTTACATCGA  ACTGGATCTC      3250
AACAGCGGTA  AGATCCTTGA  GAGTTTTCGC  CCCGAAGAAC  GTTTTCCAAT      3300
GATGAGCACT  TTTAAAGTTC  TGCTATGTGG  CGCGGTATTA  TCCCGTGATG      3350
ACGCCGGGCA  AGAGCAACTC  GGTCGCCGCA  TACACTATTC  TCAGAATGAC      3400
TTGGTTGAGT  ACTCACCAGT  CACAGAAAAG  CATCTTACGG  ATGGCATGAC      3450
AGTAAGAGAA  TTATGCAGTG  CTGCCATAAC  CATGAGTGAT  AACACTGCGG      3500
CCAACTTACT  TCTGACAACG  ATCGGAGGAC  CGAAGGAGCT  AACCGCTTTT      3550
TTGCACAACA  TGGGGGATCA  TGTAACTCGC  CTTGATCGTT  GGGAACCGGA      3600
```

```
GCTGAATGAA   GCCATACCAA   ACGACGAGCG   TGACACCACG   ATGCCAGCAG         3650

CAATGGCAAC   AACGTTGCGC   AAACTATTAA   CTGGCGAACT   ACTTACTCTA         3700

GCTTCCCGGC   AACAATTAAT   AGACTGGATG   GAGGCGGATA   AAGTTGCAGG         3750

ACCACTTCTG   CGCTCGGCCC   TTCCGGCTGG   CTGGTTTATT   GCTGATAAAT         3800

CTGGAGCCGG   TGAGCGTGGG   TCTCGCGGTA   TCATTGCAGC   ACTGGGGCCA         3850

GATGGTAAGC   CCTCCCGTAT   CGTAGTTATC   TACACGACGG   GGAGTCAGGC         3900

AACTATGGAT   GAACGAAATA   GACAGATCGC   TGAGATAGGT   GCCTCACTGA         3950

TTAAGCATTG   GTAACTGTCA   GACCAAGTTT   ACTCATATAT   ACTTTAGATT         4000

GATTTAAAAC   TTCATTTTTA   ATTTAAAAGG   ATCTAGGTGA   AGATCCTTTT         4050

TGATAATCTC   ATGACCAAAA   TCCCTTAACG   TGAGTTTTCG   TTCCACTGAG         4100

CGTCAGACCC   CGTAGAAAAG   ATCAAAGGAT   CTTCTTGAGA   TCCTTTTTTT         4150

CTGCGCGTAA   TCTGCTGCTT   GCAAACAAAA   AAACCACCGC   TACCAGCGGT         4200

GGTTTGTTTG   CCGGATCAAG   AGCTACCAAC   TCTTTTTCCG   AAGGTAACTG         4250

GCTTCAGCAG   AGCGCAGATA   CCAAATACTG   TCCTTCTAGT   GTAGCCGTAG         4300

TTAGGCCACC   ACTTCAAGAA   CTCTGTAGCA   CCGCCTACAT   ACCTCGCTCT         4350

GCTAATCCTG   TTACCAGTGG   CTGCTGCCAG   TGGCGATAAG   TCGTGTCTTA         4400

CCGGGTTGGA   CTCAAGACGA   TAGTTACCGG   ATAAGGCGCA   GCGGTCGGGC         4450

TGAACGGGGG   GTTCGTGCAC   ACAGCCCAGC   TTGGAGCGAA   CGACCTACAC         4500

CGAACTGAGA   TACCTACAGC   GTGAGCATTG   AGAAAGCGCC   ACGCTTCCCG         4550

AAGGGAGAAA   GGCGGACAGG   TATCCGGTAA   GCGGCAGGGT   CGGAACAGGA         4600

GAGCGCACGA   GGGAGCTTCC   AGGGGGAAAC   GCCTGGTATC   TTTATAGTCC         4650

TGTCGGGTTT   CGCCACCTCT   GACTTGAGCG   TCGATTTTTG   TGATGCTCGT         4700

CAGGGGGGCG   GAGCCTATGG   AAAAACGCCA   GCAACGCGGC   CTTTTTACGG         4750

TTCCTGGCCT   TTTGCTGGCC   TTTTGCTCAC   ATGTTCTTTC   CTGCGTTATC         4800

CCCTGATTCT   GTGGATAACC   GTATTACCGC   CTTTGAGTGA   GCTGATACCG         4850

CTCGCCGCAG   CCGAACGACC   GAGCGCAGCG   AGTCAGTGAG   CGAGGAAGCG         4900

GAAGAGCGCC   CAATACGCAA   ACCGCCTCTC   CCCGCGCGTT   GGCCGATTCA         4950

TTAATCCAGC   TGGCACGACA   GGTTTCCCGA   CTGGAAAGCG   GGCAGTGAGC         5000

GCAACGCAAT   TAATGTGAGT   TACCTCACTC   ATTAGGCACC   CCAGGCTTTA         5050

CACTTTATGC   TTCCGGCTCG   TATGTTGTGT   GGAATTGTGA   GCGGATAACA         5100

ATTTCACACA   GGAAACAGCT   ATGACCATGA   TTACGAATTA   A                  5141
```

( 2 ) INFORMATION FOR SEQ ID NO:10:

( i ) SEQUENCE CHARACTERISTICS:
        ( A ) LENGTH: 103 bases
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
TGCAGCAAGG   GCTACTGCCA   CACTCGAGCT   GCGCAGATGC   TAGCCTCAAG          50

ATGGCTGATC   CAAATCGATT   CCGCGGCAAA   GATCTTCCGG   TCCTGTAGAA         100

GCT                                                                    103
```

(2) INFORMATION FOR SEQ ID NO:11:

(i) SEQUENCE CHARACTERISTICS:
        (A) LENGTH: 103 bases
        (B) TYPE: nucleic acid
        (C) STRANDEDNESS: single
        (D) TOPOLOGY: linear (xi) SEQUENCE DESCRIPTION: SEQ ID NO:11:

```
AGCTTCTACA  GGACCGGAAG  ATCTTTGCCG  CGGAATCGAT  TTGGATCAGC          50
CATCTTGAGG  CTAGCATCTG  CGCAGCTCGA  GTGTGGCAGT  AGCCCTTGCT         100
GCA                                                                103
```